(12) United States Patent
Foley et al.

(10) Patent No.: US 10,183,112 B2
(45) Date of Patent: Jan. 22, 2019

(54) DEVICE FOR TRANS ANAL IRRIGATION

(71) Applicant: Hollister Incorporated, Libertyville, IL (US)

(72) Inventors: Adam J. Foley, Ballina (IE); Stephen Collum, Castlebar (IE); David Hannon, Ballina (IE)

(73) Assignee: Hollister Incorporated, Libertyville, IL (US)

(*) Notice: Subject to any disclaimer, the term of this patent is extended or adjusted under 35 U.S.C. 154(b) by 231 days.

(21) Appl. No.: 14/902,469

(22) PCT Filed: Aug. 29, 2014

(86) PCT No.: PCT/US2014/053573
§ 371 (c)(1),
(2) Date: Dec. 31, 2015

(87) PCT Pub. No.: WO2015/031851
PCT Pub. Date: Mar. 5, 2015

(65) Prior Publication Data
US 2016/0339166 A1    Nov. 24, 2016

Related U.S. Application Data

(60) Provisional application No. 62/022,051, filed on Jul. 8, 2014, provisional application No. 61/872,155, filed on Aug. 30, 2013.

(51) Int. Cl.
*A61M 3/02* (2006.01)

(52) U.S. Cl.
CPC ........ *A61M 3/0295* (2013.01); *A61M 3/0241* (2013.01); *A61M 3/0258* (2013.01);
(Continued)

(58) Field of Classification Search
CPC .............. A61M 3/0295; A61M 3/0283; A61M 2210/1067; A61M 3/0237; A61M 3/0258;
(Continued)

(56) References Cited

U.S. PATENT DOCUMENTS

| 1,004,103 A | 9/1911 | Tacey |
| 2,691,373 A | 10/1954 | Bried |

(Continued)

FOREIGN PATENT DOCUMENTS

| AT | 369994 B | 2/1983 |
| DE | 4114390 A1 | 11/1992 |

(Continued)

OTHER PUBLICATIONS

International Search Report and Written Opinion for PCT/US2014/053573 dated Feb. 24, 2015.

(Continued)

*Primary Examiner* — Nathan R Price
*Assistant Examiner* — Tasnim Mehjabin Ahmed
(74) *Attorney, Agent, or Firm* — Cook Alex Ltd.

(57) ABSTRACT

A trans-anal irrigation (TAI) system adapted for self-use includes an irrigation head supplied with water from a reservoir by a pump or by gravity feed. The irrigation head has either internal or external structures for releasably retaining the head in a user's rectum during the water flow portion of a TAI process. A guide member arm may be provided for manipulating the irrigation head for both insertion and removal. The irrigation head is reliably attached to the guide member arm. The guide member arm may include an integral manual pump.

18 Claims, 34 Drawing Sheets

(52) U.S. Cl.
CPC ........ *A61M 3/0262* (2013.01); *A61M 3/0279* (2013.01); *A61M 3/0245* (2013.01); *A61M 2210/1067* (2013.01)

(58) Field of Classification Search
CPC ...... A61M 25/10182; A61M 25/10181; A61M 25/1018; A61M 25/1011; A61B 2017/3486
See application file for complete search history.

(56) References Cited

U.S. PATENT DOCUMENTS

| | | | |
|---|---|---|---|
| 3,854,483 | A | 12/1974 | Powers |
| 3,889,676 | A | 6/1975 | Greene |
| 3,894,540 | A | 7/1975 | Bonner, Jr. |
| 3,934,722 | A | 1/1976 | Goldberg |
| 4,043,345 | A | 8/1977 | Kramann et al. |
| 4,109,659 | A | 8/1978 | Sheridan |
| 4,386,607 | A | 6/1983 | Miller |
| 4,956,298 | A | 9/1990 | Diekmann |
| 5,149,326 | A | 9/1992 | Woodgrift et al. |
| 5,217,114 | A | 6/1993 | Gadberry et al. |
| 5,225,165 | A | 7/1993 | Perlman |
| 5,405,319 | A | 4/1995 | Abell et al. |
| 5,413,561 | A | 5/1995 | Fischell et al. |
| 5,417,326 | A | 5/1995 | Winer |
| 5,868,265 | A | 2/1999 | Kobayashi |
| 5,881,774 | A | 3/1999 | Utterberg |
| 6,106,506 | A | 8/2000 | Abell et al. |
| 6,258,078 | B1 | 7/2001 | Thilly |
| 6,468,245 | B2 | 10/2002 | Alexandersen |
| 6,585,721 | B2 | 7/2003 | Fiore |
| 6,822,253 | B1 | 11/2004 | Martin et al. |
| 6,908,013 | B2 | 6/2005 | Thomson et al. |
| 6,984,226 | B1 | 1/2006 | Abell et al. |
| 7,120,487 | B2 | 10/2006 | Nelson |
| 7,438,704 | B1 | 10/2008 | Kawashima et al. |
| 7,546,931 | B2 | 6/2009 | Giusti |
| 7,571,804 | B2 | 8/2009 | Kjellmann Bruun et al. |
| 7,585,294 | B2 | 9/2009 | Jensen et al. |
| 7,614,514 | B2 | 11/2009 | Fuchs |
| 7,625,355 | B2 | 12/2009 | Yu |
| 7,682,353 | B2 | 3/2010 | Tanghoj |
| 7,717,284 | B2 | 5/2010 | Giusti |
| 7,748,550 | B2 | 7/2010 | Cho |
| 7,867,220 | B2 | 1/2011 | Tanghoj |
| 7,886,907 | B2 | 2/2011 | Murray et al. |
| 7,914,505 | B2 | 3/2011 | Moeller-Jensen et al. |
| 7,942,578 | B2 | 5/2011 | Andersen |
| 7,967,744 | B2 | 6/2011 | Kaye et al. |
| 8,137,309 | B2 | 3/2012 | Nishtala et al. |
| 8,172,101 | B2 | 5/2012 | Giusti |
| 8,181,778 | B1 | 5/2012 | van Groningen et al. |
| 8,230,993 | B2 | 7/2012 | Tanghoej |
| 8,231,589 | B2 | 7/2012 | Moeller-Jensen et al. |
| 8,282,624 | B2 | 10/2012 | Tanghoej et al. |
| 8,361,057 | B2 | 1/2013 | Tanghoej et al. |
| 8,398,615 | B2 | 3/2013 | Torstensen et al. |
| 8,434,639 | B2 | 5/2013 | Markert |
| 8,439,213 | B2 | 5/2013 | Goria et al. |
| 8,448,798 | B2 | 5/2013 | Groubert |
| 8,491,568 | B2 | 7/2013 | Schertiger et al. |
| 8,579,115 | B2 | 11/2013 | Murphy et al. |
| 8,752,722 | B2 | 6/2014 | Kuhn et al. |
| 8,863,968 | B2 | 10/2014 | Giusti |
| 9,352,318 | B2 | 5/2016 | Giusti |
| 9,422,089 | B2 | 8/2016 | Wheeler |
| 2002/0019613 | A1* | 2/2002 | Alexandersen ..... A61M 3/0241 604/279 |
| 2003/0073963 | A1 | 4/2003 | Falconer |
| 2003/0073974 | A1 | 4/2003 | Falconer |
| 2004/0097997 | A1* | 5/2004 | Di Cecco ............. A61F 11/006 606/162 |
| 2004/0267198 | A1 | 12/2004 | Torstensen |
| 2006/0009732 | A1 | 1/2006 | Hardy |
| 2006/0142737 | A1 | 6/2006 | Tanghoj |
| 2006/0180585 | A1 | 8/2006 | Cunningham et al. |
| 2008/0033371 | A1 | 2/2008 | Updegraff et al. |
| 2008/0097384 | A1 | 4/2008 | Pacey |
| 2008/0289984 | A1 | 11/2008 | Raven |
| 2009/0054876 | A1 | 2/2009 | Borodulin |
| 2009/0166361 | A1 | 7/2009 | Lourenco |
| 2010/0106236 | A1 | 4/2010 | Nelson |
| 2010/0211050 | A1 | 8/2010 | Luther |
| 2010/0324540 | A1 | 12/2010 | Paulen et al. |
| 2011/0060317 | A1 | 3/2011 | Frojd |
| 2011/0224653 | A1 | 9/2011 | Torstensen |
| 2011/0282311 | A1 | 11/2011 | Nishtala |
| 2011/0302709 | A1 | 12/2011 | Taylor |
| 2012/0016318 | A1 | 1/2012 | Hoang et al. |
| 2012/0143168 | A1* | 6/2012 | Bjerregaard ........ A61M 3/0295 604/514 |
| 2012/0179144 | A1 | 7/2012 | Carleo |
| 2012/0271281 | A1 | 10/2012 | Schertiger |
| 2013/0068767 | A1 | 3/2013 | Fraser et al. |
| 2013/0134123 | A1 | 5/2013 | Fraser |
| 2013/0161344 | A1 | 6/2013 | Park et al. |
| 2013/0218136 | A1 | 8/2013 | Tanghoej et al. |
| 2013/0289537 | A1 | 10/2013 | Schertiger |
| 2013/0292286 | A1 | 11/2013 | Van Groningen |
| 2014/0262860 | A1 | 9/2014 | Hagel |
| 2014/0263436 | A1 | 9/2014 | Gelov et al. |
| 2014/0360896 | A1 | 12/2014 | Torstensen |
| 2016/0016703 | A1 | 1/2016 | Muhlemann |
| 2016/0023818 | A1 | 1/2016 | Gelov et al. |
| 2016/0059999 | A1 | 3/2016 | Fraser et al. |
| 2016/0228872 | A1 | 8/2016 | Giusti |

FOREIGN PATENT DOCUMENTS

| | | |
|---|---|---|
| DE | 20117438 U1 | 3/2002 |
| DE | 10213411 A1 | 10/2003 |
| DE | 20317135 U1 | 1/2004 |
| DE | 202005008071 U1 | 7/2005 |
| DE | 202005009946 U1 | 9/2005 |
| DE | 202006013663 U1 | 11/2006 |
| DE | 202010006267 U1 | 11/2010 |
| DE | 202010007433 U1 | 6/2011 |
| DE | 202011107025 U1 | 1/2013 |
| DE | 202011107059 U1 | 1/2013 |
| DE | 102013014483 A1 | 6/2014 |
| EP | 0041487 A | 12/1981 |
| EP | 0134630 A | 3/1985 |
| EP | 0861639 A2 | 9/1998 |
| EP | 0809520 B1 | 4/1999 |
| EP | 0996542 A1 | 5/2000 |
| EP | 1051984 A2 | 11/2000 |
| EP | 1180373 A2 | 2/2002 |
| EP | 1011754 B1 | 9/2004 |
| EP | 1466645 A2 | 10/2004 |
| EP | 1392575 B1 | 9/2005 |
| EP | 1593710 A1 | 11/2005 |
| EP | 1634554 A2 | 3/2006 |
| EP | 1638856 A1 | 3/2006 |
| EP | 1246655 B1 | 5/2006 |
| EP | 1434611 B1 | 6/2006 |
| EP | 1671663 A1 | 6/2006 |
| EP | 1303243 B1 | 1/2007 |
| EP | 1752175 A2 | 2/2007 |
| EP | 1752176 A1 | 2/2007 |
| EP | 1752177 A1 | 2/2007 |
| EP | 1039858 B1 | 5/2007 |
| EP | 1491223 B1 | 5/2007 |
| EP | 1878461 A1 | 1/2008 |
| EP | 1897579 A1 | 3/2008 |
| EP | 1897580 A1 | 3/2008 |
| EP | 1946785 A1 | 7/2008 |
| EP | 1946786 A1 | 7/2008 |
| EP | 1372755 B1 | 8/2008 |
| EP | 0915715 B1 | 9/2008 |
| EP | 1531885 B1 | 10/2008 |
| EP | 1977778 A1 | 10/2008 |
| EP | 1982741 A2 | 10/2008 |
| EP | 1514572 B1 | 12/2008 |

(56) References Cited

FOREIGN PATENT DOCUMENTS

| | | |
|---|---|---|
| EP | 2027832 A2 | 2/2009 |
| EP | 2042211 A1 | 4/2009 |
| EP | 2044963 A1 | 4/2009 |
| EP | 2060296 A1 | 5/2009 |
| EP | 2072075 A1 | 6/2009 |
| EP | 2106821 A1 | 10/2009 |
| EP | 2035292 B1 | 5/2010 |
| EP | 2251454 A2 | 11/2010 |
| EP | 2468326 A1 | 12/2010 |
| EP | 2211937 B1 | 7/2011 |
| EP | 2125070 B1 | 4/2012 |
| EP | 2452706 A2 | 5/2012 |
| EP | 2468319 A1 | 6/2012 |
| EP | 2005981 B1 | 9/2012 |
| EP | 1909864 B1 | 10/2012 |
| EP | 2504054 A1 | 10/2012 |
| EP | 2515985 A1 | 10/2012 |
| EP | 2158926 B1 | 5/2013 |
| EP | 2596831 A2 | 5/2013 |
| EP | 2242696 B1 | 6/2013 |
| EP | 2617316 A2 | 7/2013 |
| EP | 2638927 A2 | 9/2013 |
| EP | 2671601 A1 | 11/2013 |
| EP | 2671602 A1 | 12/2013 |
| EP | 2679259 A1 | 1/2014 |
| EP | 2679260 A1 | 1/2014 |
| EP | 2679261 A1 | 1/2014 |
| EP | 2682069 A1 | 1/2014 |
| EP | 2686054 A1 | 1/2014 |
| EP | 2703019 A1 | 3/2014 |
| EP | 2416819 B1 | 8/2014 |
| EP | 1752174 B1 | 9/2014 |
| EP | 2774648 A1 | 9/2014 |
| EP | 2576374 B1 | 9/2016 |
| FR | 2717676 A1 | 9/1995 |
| GB | 2031735 A | 4/1980 |
| GB | 2033231 A | 5/1980 |
| GB | 2322079 A | 8/1998 |
| GB | 2496900 A | 5/2013 |
| JP | 2001025473 A | 1/2001 |
| KR | 20110101674 | 7/2012 |
| WO | WO 96-08219 A1 | 3/1996 |
| WO | WO 96-25188 A1 | 8/1996 |
| WO | WO 96-31250 A1 | 10/1996 |
| WO | WO 97-15335 A1 | 5/1997 |
| WO | WO 97-26937 A1 | 7/1997 |
| WO | WO 97-41811 A1 | 11/1997 |
| WO | WO 97-49441 A1 | 12/1997 |
| WO | WO 98-11932 A1 | 3/1998 |
| WO | WO 98-19729 A1 | 5/1998 |
| WO | WO 98-20722 A2 | 5/1998 |
| WO | WO 98-23312 A1 | 6/1998 |
| WO | WO 99-30652 A1 | 6/1999 |
| WO | WO 99-30761 A1 | 6/1999 |
| WO | WO 99-42155 A2 | 8/1999 |
| WO | WO 99-59656 A1 | 11/1999 |
| WO | WO 00-16843 A1 | 3/2000 |
| WO | WO 00-30575 A1 | 6/2000 |
| WO | WO 00-47494 A1 | 8/2000 |
| WO | WO 01-43807 A1 | 6/2001 |
| WO | WO 01-49345 A1 | 7/2001 |
| WO | WO 01-60255 A1 | 8/2001 |
| WO | WO 02-07668 A1 | 1/2002 |
| WO | WO 02-13887 A1 | 2/2002 |
| WO | WO 02-060361 A2 | 8/2002 |
| WO | WO 02-074363 A2 | 9/2002 |
| WO | WO 02-080843 A2 | 10/2002 |
| WO | WO 03-001994 A1 | 1/2003 |
| WO | WO 03-008028 A2 | 1/2003 |
| WO | WO 03-008029 A2 | 1/2003 |
| WO | WO 03-022561 A1 | 3/2003 |
| WO | WO 03-030967 A1 | 4/2003 |
| WO | WO 03-030968 A1 | 4/2003 |
| WO | WO 03-030969 A1 | 4/2003 |
| WO | WO 03-045487 A2 | 6/2003 |
| WO | WO 03-061732 A2 | 7/2003 |
| WO | WO 03-063668 A1 | 8/2003 |
| WO | WO 03/092779 A1 | 11/2003 |
| WO | WO 03-097237 A2 | 11/2003 |
| WO | WO 2004-006993 A1 | 1/2004 |
| WO | WO 2004-021890 A1 | 3/2004 |
| WO | WO 2004-032750 A1 | 4/2004 |
| WO | WO 2004-035123 A1 | 4/2004 |
| WO | WO 2004-050155 A1 | 6/2004 |
| WO | WO 2004-054446 A1 | 7/2004 |
| WO | WO 2004-060259 A2 | 7/2004 |
| WO | WO 2004-103153 A2 | 12/2004 |
| WO | WO 2004-112712 A2 | 12/2004 |
| WO | WO 2005-003725 A2 | 1/2005 |
| WO | WO 2005-004964 A1 | 1/2005 |
| WO | WO 2005-004970 A1 | 1/2005 |
| WO | WO 2005-014055 A2 | 2/2005 |
| WO | WO 2005-032617 A2 | 4/2005 |
| WO | WO 2006-005349 A2 | 1/2006 |
| WO | WO 2006-010556 A1 | 2/2006 |
| WO | WO 2006-015223 A2 | 2/2006 |
| WO | WO 2006/017439 A2 | 2/2006 |
| WO | WO 2006-024205 A1 | 3/2006 |
| WO | WO 2006/044249 A2 | 4/2006 |
| WO | WO 2006/044621 A2 | 4/2006 |
| WO | WO 2006/045809 A1 | 5/2006 |
| WO | WO 2006/121183 A1 | 11/2006 |
| WO | WO 2006-135934 A2 | 12/2006 |
| WO | WO 2007/005851 A2 | 1/2007 |
| WO | WO 2007/022223 A2 | 2/2007 |
| WO | WO 2007/038988 A1 | 4/2007 |
| WO | WO 2007/050685 A2 | 5/2007 |
| WO | WO 2007/081264 A1 | 7/2007 |
| WO | WO 2007/082540 A2 | 7/2007 |
| WO | WO 2007-103995 A2 | 9/2007 |
| WO | WO 2007/106356 A2 | 9/2007 |
| WO | WO 2007/106431 A2 | 9/2007 |
| WO | WO 2007/111891 A2 | 10/2007 |
| WO | WO 2007/121137 A2 | 10/2007 |
| WO | WO 2008/024136 A1 | 2/2008 |
| WO | WO 2008/030999 | 3/2008 |
| WO | WO 2008/039910 A2 | 4/2008 |
| WO | WO 2008-048856 A2 | 4/2008 |
| WO | WO 2008-058160 A2 | 5/2008 |
| WO | WO 2008-087220 A1 | 7/2008 |
| WO | WO 2008-087221 A2 | 7/2008 |
| WO | WO 2008/089081 A1 | 7/2008 |
| WO | WO 2008/090551 A1 | 7/2008 |
| WO | WO 2008/137353 A1 | 11/2008 |
| WO | WO 2009/010975 A1 | 1/2009 |
| WO | WO 2009-015152 A1 | 1/2009 |
| WO | WO 2009/017541 A1 | 2/2009 |
| WO | WO 2009-056906 A1 | 5/2009 |
| WO | WO 2009/066163 | 5/2009 |
| WO | WO 2009/066163 A1 | 5/2009 |
| WO | WO 2011-023196 A1 | 8/2009 |
| WO | WO 2009-128109 A1 | 10/2009 |
| WO | WO 2009/139878 A1 | 11/2009 |
| WO | WO 2009-144028 A1 | 12/2009 |
| WO | WO 2009-153973 A1 | 12/2009 |
| WO | WO 2010/006620 A1 | 1/2010 |
| WO | WO 2010-047501 A2 | 4/2010 |
| WO | WO 2010-057208 A1 | 5/2010 |
| WO | WO 2010-077980 A1 | 7/2010 |
| WO | WO 2010-115430 A1 | 10/2010 |
| WO | WO 2010-115431 A2 | 10/2010 |
| WO | WO 2010-126586 A1 | 11/2010 |
| WO | WO 2010/130261 A1 | 11/2010 |
| WO | WO 2011/011023 | 1/2011 |
| WO | WO 2011-012323 A1 | 2/2011 |
| WO | WO 2011/019359 A1 | 2/2011 |
| WO | WO 2011/026929 A1 | 3/2011 |
| WO | WO 2011/034911 A1 | 3/2011 |
| WO | WO 2011-075581 A1 | 6/2011 |
| WO | WO 2011/079129 A1 | 6/2011 |
| WO | WO 2011-105644 A1 | 9/2011 |
| WO | WO 2011/109393 A1 | 9/2011 |
| WO | WO 2011/139498 A1 | 11/2011 |
| WO | WO 2011/147803 A1 | 12/2011 |

(56) References Cited

FOREIGN PATENT DOCUMENTS

| | | |
|---|---|---|
| WO | WO 2012/006629 A2 | 1/2012 |
| WO | WO 2012/013662 A1 | 2/2012 |
| WO | WO 2012/016179 A1 | 2/2012 |
| WO | WO 2012/016570 A2 | 2/2012 |
| WO | WO 2012/016571 A2 | 2/2012 |
| WO | WO 2012/079590 A1 | 6/2012 |
| WO | WO 2012/085107 A2 | 6/2012 |
| WO | WO 2012/110755 A2 | 8/2012 |
| WO | WO 2012-120456 A2 | 9/2012 |
| WO | WO 2012/134804 A1 | 10/2012 |
| WO | WO 2012/154946 A1 | 11/2012 |
| WO | WO 2012/156478 A1 | 11/2012 |
| WO | WO 2012-164559 A1 | 12/2012 |
| WO | WO 2012/166045 A1 | 12/2012 |
| WO | WO 2012/166967 A1 | 12/2012 |
| WO | WO 2013-026564 A1 | 2/2013 |
| WO | WO 2013-026565 A1 | 2/2013 |
| WO | WO 2013/029620 A1 | 3/2013 |
| WO | WO 2013/029621 A1 | 3/2013 |
| WO | WO 2013/029622 A1 | 3/2013 |
| WO | WO 2013/075725 A1 | 5/2013 |
| WO | WO 2013-076446 A1 | 5/2013 |
| WO | WO 2013/083137 A1 | 6/2013 |
| WO | WO 2013/090778 A1 | 6/2013 |
| WO | WO 2013/098190 A1 | 7/2013 |
| WO | WO 2013/105091 A1 | 7/2013 |
| WO | WO 2013-163364 A1 | 10/2013 |
| WO | WO 2013-182593 A1 | 12/2013 |
| WO | WO 2013/184158 A1 | 12/2013 |
| WO | WO 2014-001292 A1 | 1/2014 |
| WO | WO 2014-001313 A1 | 1/2014 |
| WO | WO 2014-001322 A1 | 1/2014 |
| WO | WO 2014/062225 A1 | 4/2014 |
| WO | WO 2014/063711 A1 | 5/2014 |
| WO | WO 2014-064414 A1 | 5/2014 |
| WO | WO 2014/074142 A1 | 5/2014 |
| WO | WO 2014/074147 A1 | 5/2014 |
| WO | WO 2014/081859 A1 | 5/2014 |
| WO | WO 2014/085597 A1 | 6/2014 |
| WO | WO 2014-089278 A1 | 6/2014 |
| WO | WO 2014/093056 A1 | 6/2014 |
| WO | WO 2014/139767 | 9/2014 |
| WO | WO 2014/140328 A1 | 9/2014 |
| WO | WO 2014/142895 A1 | 9/2014 |
| WO | WO 2014/142917 A1 | 9/2014 |
| WO | WO 2014/142923 A1 | 9/2014 |
| WO | WO 2014/142930 A1 | 9/2014 |
| WO | WO 2014/144714 | 9/2014 |
| WO | WO 2014/145211 A2 | 9/2014 |
| WO | WO 2014/147620 A1 | 9/2014 |
| WO | WO 2014/149276 A1 | 9/2014 |
| WO | WO 2014/159869 A2 | 10/2014 |
| WO | WO 2014/165046 A1 | 10/2014 |
| WO | WO 2014/176486 A1 | 10/2014 |
| WO | WO 2014/76867 A1 | 11/2014 |
| WO | WO 2015/184365 | 12/2015 |

OTHER PUBLICATIONS

Urinary Incontinence Applicance, Aids and Equipment, R.N.P. Carroll, retrieved on Apr. 3, 2014 from http://link.springer.com/chapter/10.1007/978-1-4471-1461-1_6# dated Dec. 31, 1992.
International Search Report dated Feb. 24, 2015, for International Application No. PCT/US2014/053573.

* cited by examiner

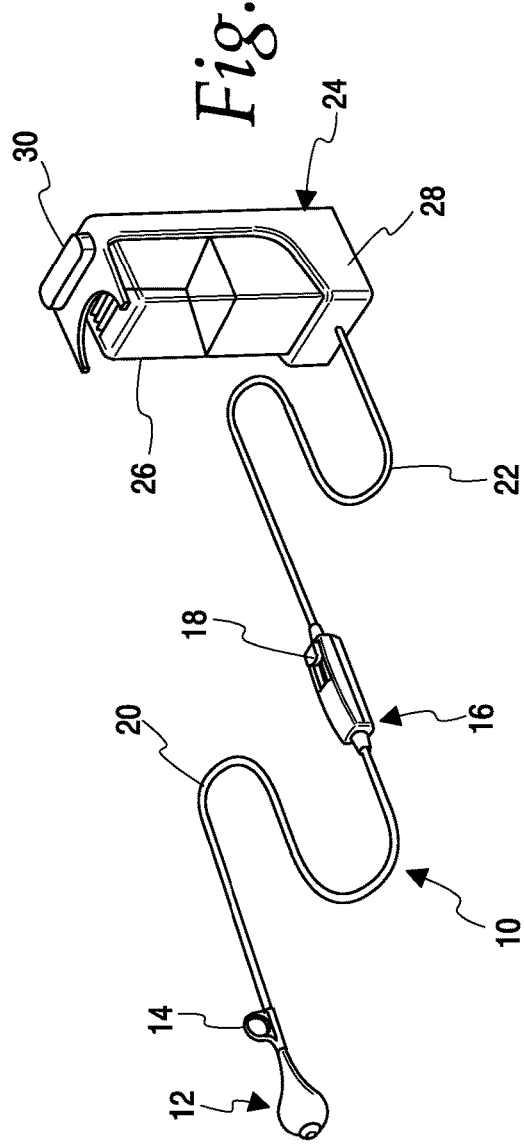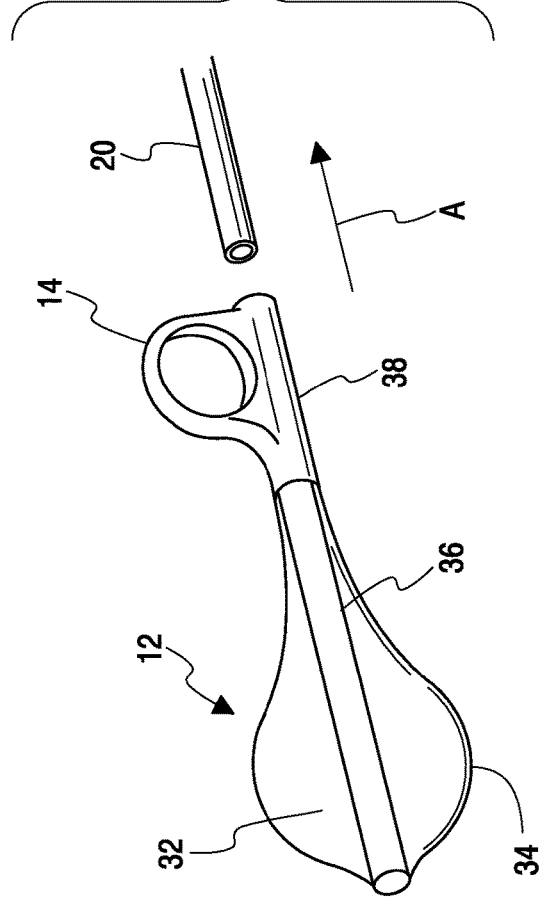

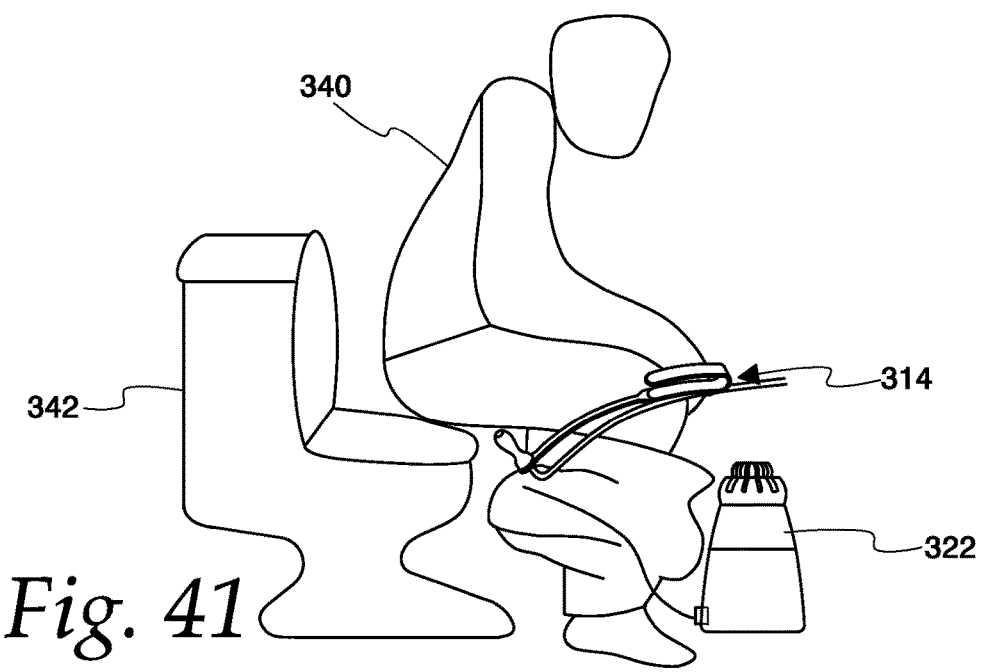
Fig. 41
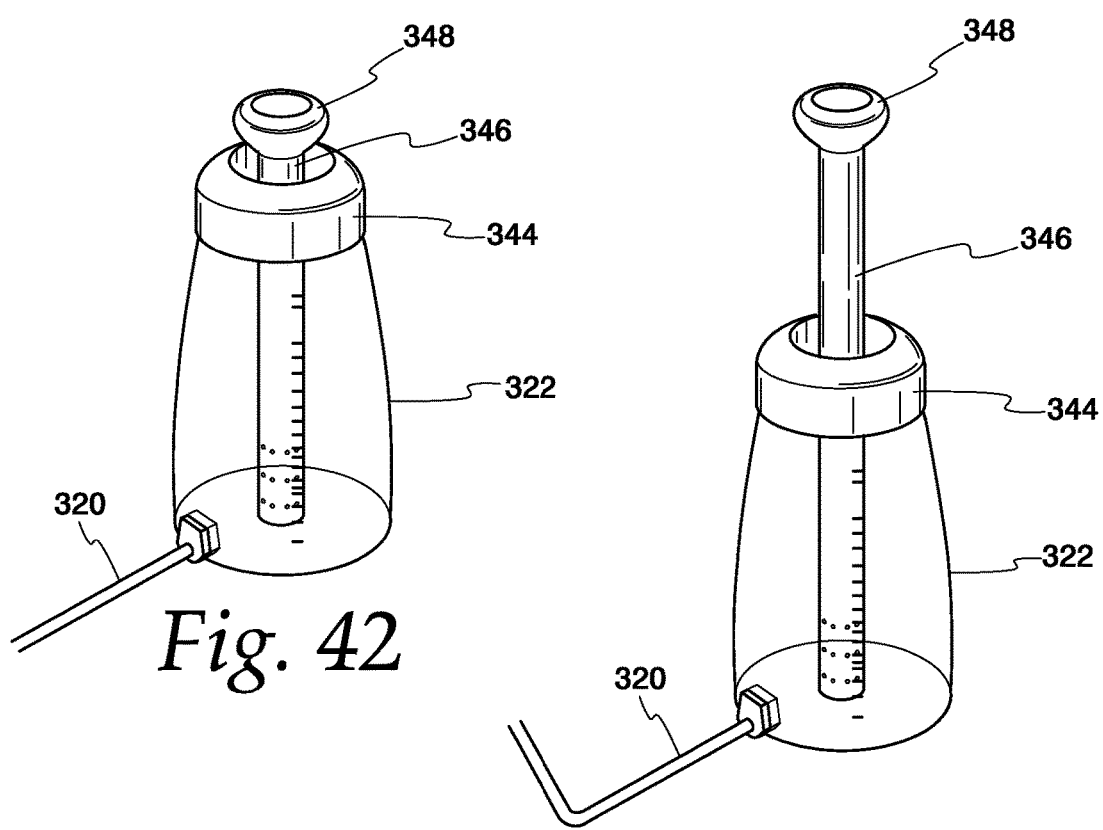
Fig. 42
Fig. 43

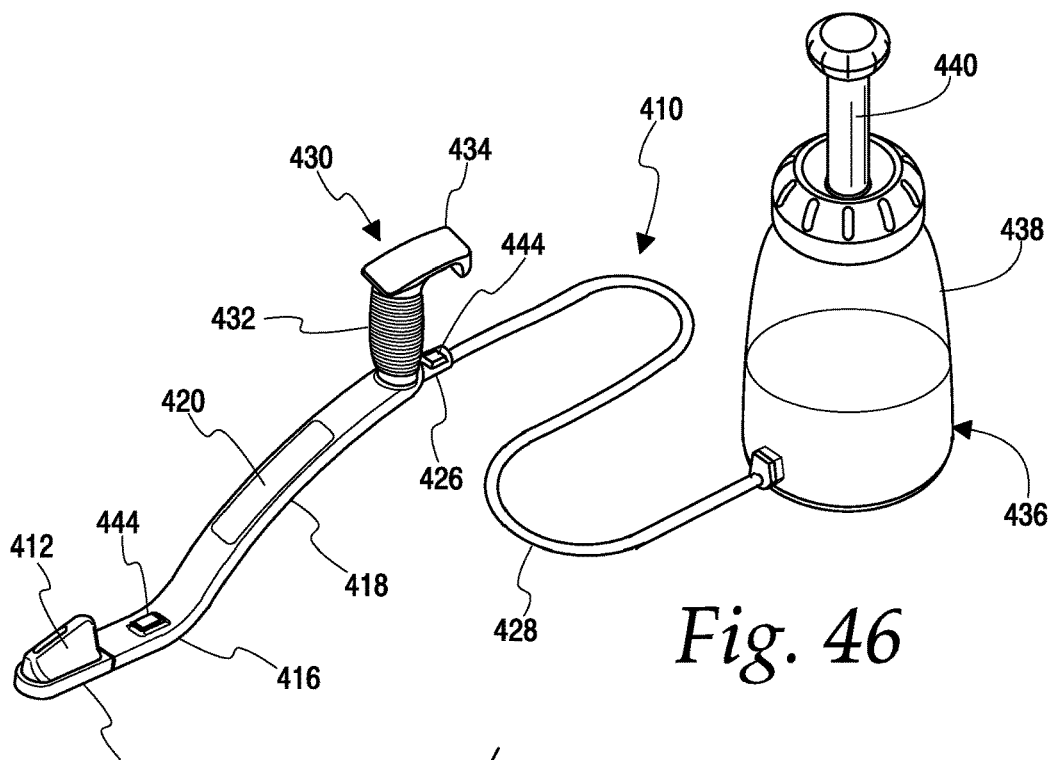
Fig. 46
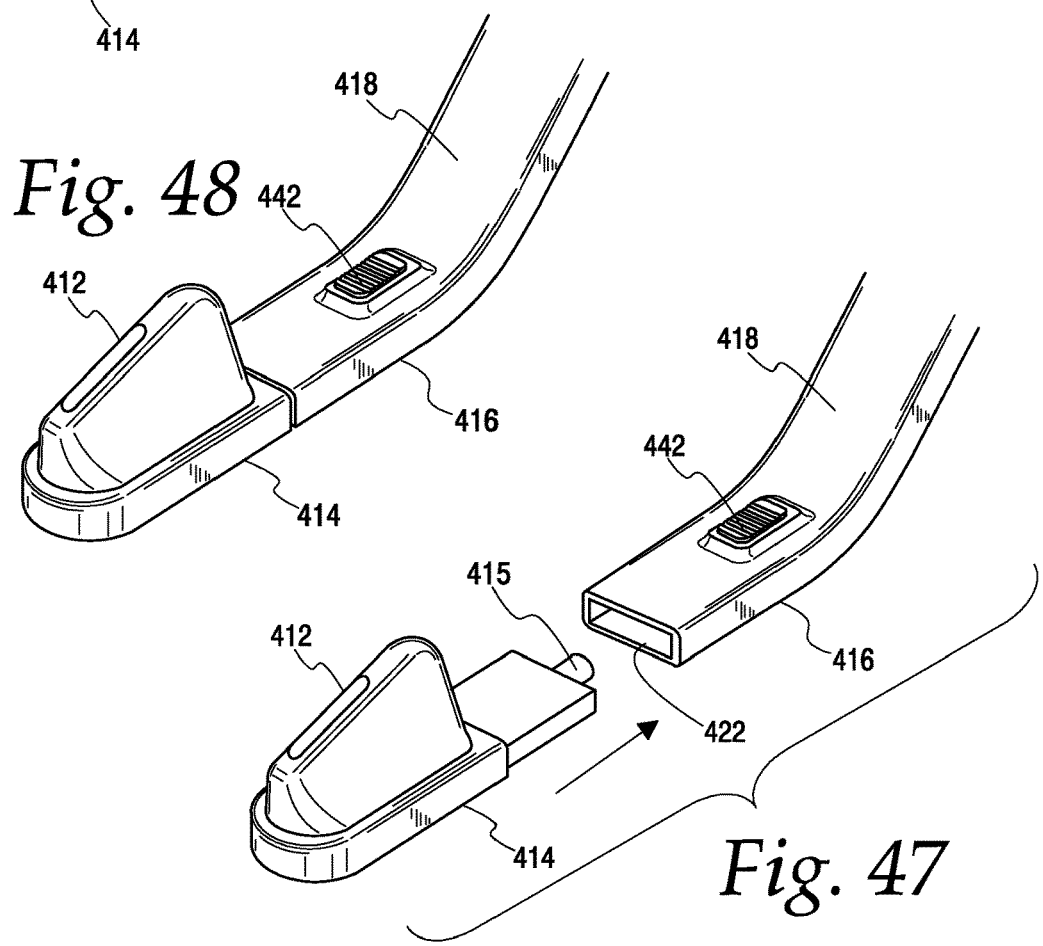
Fig. 48
Fig. 47

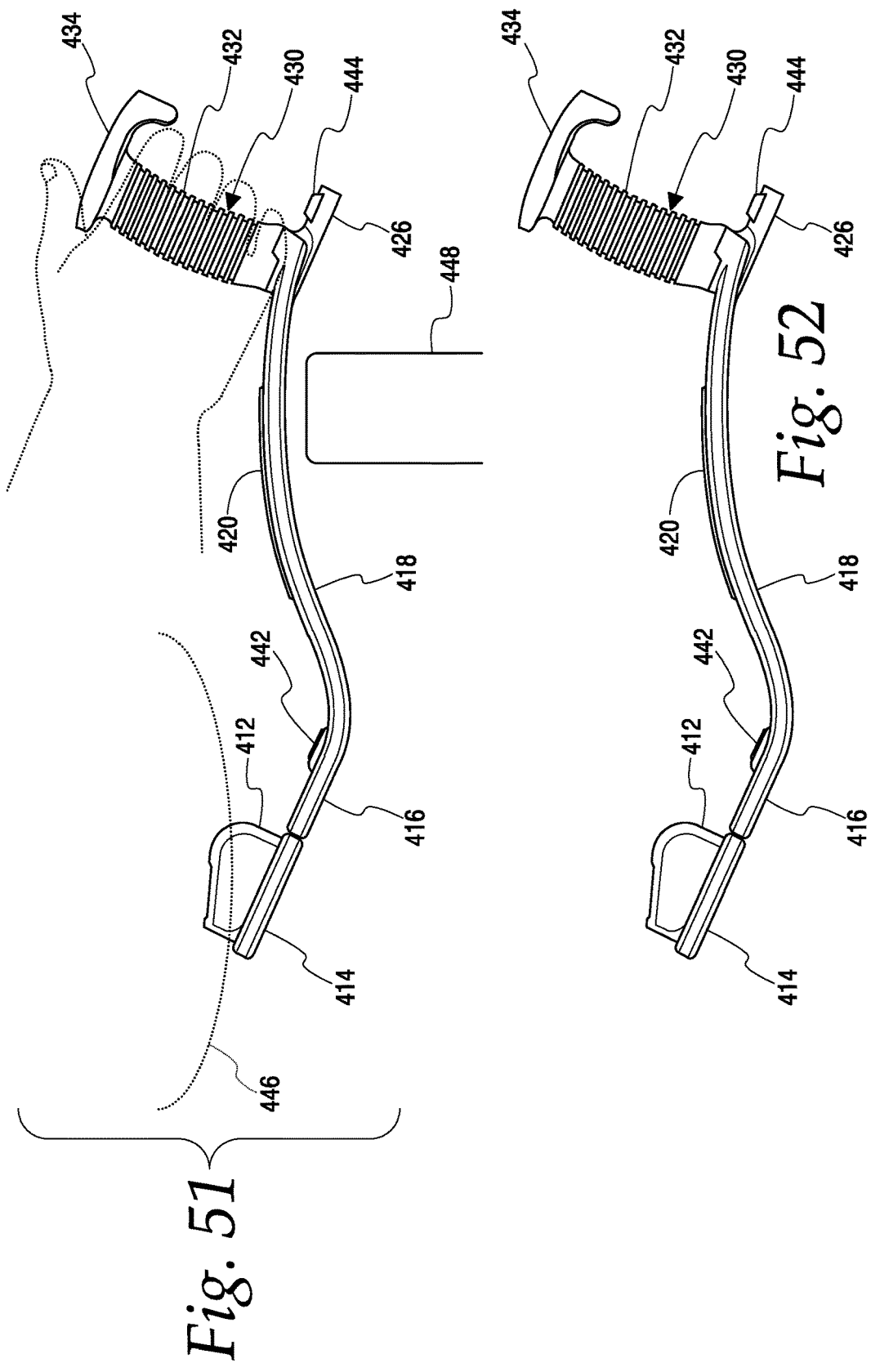

DEVICE FOR TRANS ANAL IRRIGATION

CROSS-REFERENCE TO RELATED APPLICATIONS

This application claims the benefit and priority of U.S. Patent Application Ser. No. 61/872,155, filed Aug. 30, 2013 and U.S. Patent Application Ser. No. 62/022,051, filed Jul. 8, 2014, the disclosures of which are incorporated herein by reference.

FIELD OF THE DISCLOSURE

The present disclosure is directed to trans-anal irrigation (TAI) devices, methods and systems.

BACKGROUND

Many individuals suffering spinal cord injury (SCI) and other medical conditions (e.g., cauda equina syndrome, multiple sclerosis, stoma patients who have undergone stoma surgery, spina bifida, and chronic constipation) may need to avail themselves of bowel management treatments, in many cases along with a bladder management program. For SCI users, the issues of independence, dexterity, and ease of use are important needs that must be addressed by a bowel management program. Users can avail themselves of various solutions such as pharmacological (laxatives/suppository), digital stimulation, diet control and others, with the aim of having a regular bowel management routine without constipation or fecal incontinence.

SUMMARY

In one aspect, the present disclosure is directed to trans-anal irrigation (TAI) which is a solution for use in bowel care. TAI is the delivery of irrigating liquid into the colon to flush the system of stool and create pseudo-continence for the end user. Systems currently on the market allow the user to utilize a product over the toilet or in a commode/shower chair to introduce water into the bowel through a rectal catheter (in the form of rectal balloons or cones). The user will introduce an amount of water into the bowel (typically 500-700 mls) in order to flush out stool located in the bowel passage. The user will typically introduce the water, wait for a period of time (30+ minutes) and allow gravity to flush the water and stool out of the body. The user can then have peace of mind through use of the product. This disclosure sets forth a solution for use by an SCI user which he/she can easily set up and utilize independently.

Unlike currently available TAI solutions the TAI platform of the present disclosure delivers a bowel irrigation solution that can benefit patients with neurogenic bowel dysfunction of all dexterity levels. End-users will prefer the ease of use of the controls and body interface compared to other options while finding the product of the present disclosure intuitive, comfortable and safe. Easy to slide controls guide the automated dispensing of the water without difficult seals or hard-to-manipulate controls.

The TAI platform of the present disclosure addresses users such as those having neurogenic bowel dysfunction including MS, SB, SCI, partial paraplegics, full paraplegics, partial tetraplegics, (usually patients that can self-catheterize). Such users typically have the following needs:

To be able to easily and confidently perform anal irrigation (i.e., insert and keep the bowel catheter in place, know how to use it correctly, etc.). The present disclosure addresses this need by providing balloon loading and inflation which can be performed with ease by users with reduced hand function. The powered system is easy and intuitive to learn and operate.

To be able to empty a user's bowels without requiring digital stimulation or manual evacuation. The present disclosure addresses this need by providing TAI that can reduce the need for digital interventions.

To be able to complete a bowel management routine easily and efficiently. The present disclosure addresses this need by providing a powered pumping system that will speed up the routine and will demand less physical effort.

To be able to stimulate a bowel movement (especially when constipated) and always get a good result (i.e., stool not too hard or soft). The present disclosure addresses this need by providing TAI that is effective in dealing with constipation and high blockages.

An improved and simplified irrigation option compared to current products. The present disclosure addresses this need by providing an intuitive, easy-to-understand and train, hands-free pumping system for the TAI user.

The TAI platform of the present disclosure requires limited physical effort to pressurize the system. The system may be battery powered. It is hands-free and intuitive. This makes it easier to maintain a routine bowel management program. The system is easier to use than prior art products. Patients with limited dexterity will have less difficulty with the controls. The system of the present disclosure is the most intuitive TAI product. Patients will experience a less confusing set-up and use of the product resulting in fewer accidents. When combined with a bed module, the product may be used with patients of any dexterity level. The system is less bulk for easy transport and storage.

In one aspect the system of the present disclosure may include an oil-filled displacement irrigation head with a finger loading section, a simple slider pressure on/off controller device, and a loading device including a rigid irrigating liquid reservoir and press pump.

The system may include a disposable and ergonomically-shaped irrigation head for insertion into the rectum. A small scale motorized pump may be turned on to pump or draw irrigating liquid from a source into the bowel utilizing a set amount of pressure. The overall design and function of this system provides the user with an easy-to-use, automatic operation and process to conduct TAI activities.

In another aspect, the system of the present disclosure may include a disposable (i.e., non-reusable), ergonomically-shaped irrigation head for insertion into the rectum. A small scale, motorized pump may be turned on to pump or draw liquid from an irrigating liquid supply into the bowel, utilizing a set amount of pressure and irrigating liquid volume, a sufficiently-sized irrigating liquid reservoir and irrigation tubing. The overall design and function of this system provides an automatic/motorized operation that makes it easy for a user to insert and carry out a TAI procedure.

In still another aspect the system of the present disclosure may include a modular style system which features a simplified gravity feed system utilizing a hanging bag, large in-line open valve ports and modular irrigation heads for use by different users such as limited dexterity users, stoma patients, and clinicians.

In yet another aspect of the system of the present disclosure, the system may include a soft, silicone and ergonomically-shaped insertion head which is easier to insert into the rectum and less intimidating to the user. The system may also include a reusable guide member to which a user can attach the irrigation head to extend the user's reach and hold the irrigation head while sitting on a toilet. Attached to the head and guide member may be a large easy-to-fill irrigating liquid supply which includes a typically rigid reservoir that may be pressurized to allow the system to introduce irrigating liquid into the body. The system will be easy to manipulate due to the user-friendly features included in the design.

In an alternate form of the guide member, a disposable, ergonomically shaped irrigation head cone for insertion into the rectum may be provided; this head may be loaded into the front section of a guide member or handle device which features a number of assistive features such as a loading orientation mirror, quick release/ejection port release buttons and a sufficiently-sized handle which is also ergonomically-shaped and designed to comfortably accommodate a user's hand during use.

In a further alternate form of a guide member a large ergonomically designed handle with a built-in manual pump may be included. The device will typically be utilized by a user seated on the toilet and will be used between the user's legs and be held in the manner of a joystick to allow for more control. The device allows the reach of the irrigation head to be extended for insertion into the rectum and further allows for the manual pumping of irrigating liquid from the fluid source into the bowel. Pumping may be achieved using the large handle attached to the handle gripper pump.

BRIEF DESCRIPTION OF THE DRAWINGS

FIG. 1 is a perspective view of one embodiment of a TAI system.

FIG. 2 is an enlarged view of the irrigation head of the embodiment of FIG. 1.

FIG. 41 is a diagrammatic view of a user seated on a toilet and preparing to use the guide member system of FIG. 33.

FIG. 42 is a perspective view of the irrigating liquid supply and pump.

FIG. 43 is a perspective view of the irrigating liquid supply and pump.

FIG. 46 is a perspective view of another embodiment of the systems disclosed herein, showing a TAI guide member handle system.

FIG. 47 is an exploded perspective view of the guide member handle of FIG. 46 with the irrigation head removed.

FIG. 48 is a view similar to FIG. 47 but with the irrigation head installed on the guide member handle.

FIG. 51 is a diagrammatic side view of the guide member handle of FIG. 47 in use FIG. 52 is a side elevation view of the guide member handle of FIG. 47 resting on a flat surface.

DETAILED DESCRIPTION OF THE EMBODIMENTS

Figure 3A:
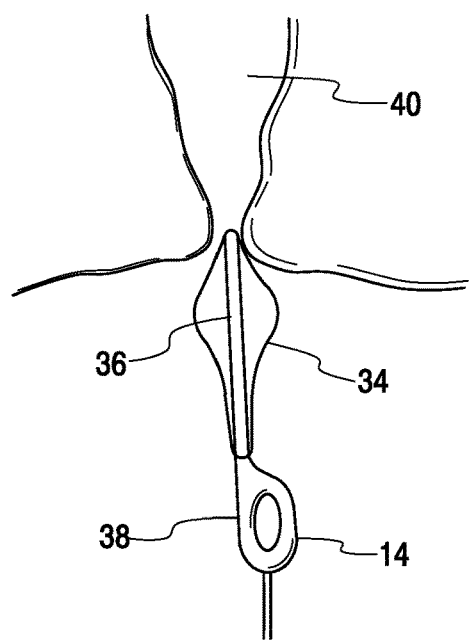
FIGS. 3A, 3B, 3C and 3D are diagrammatic sections illustrating insertion and removal of the irrigation head.
Figure 3B:
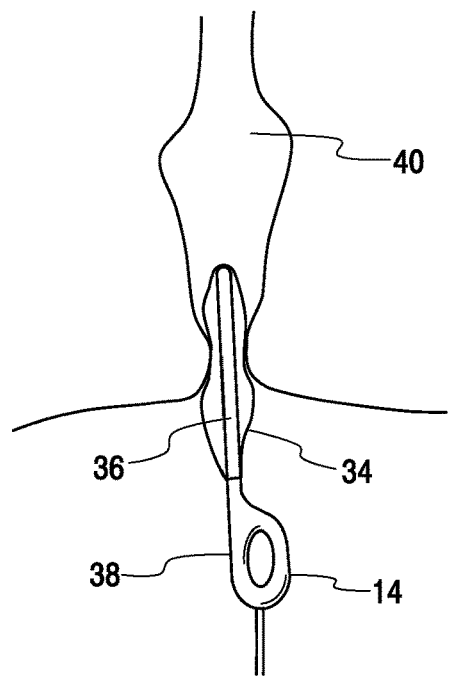
Figure 3C:
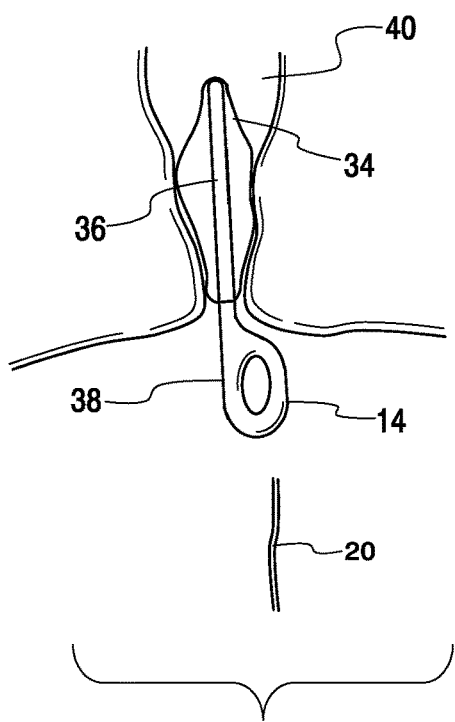
Figure 3D:
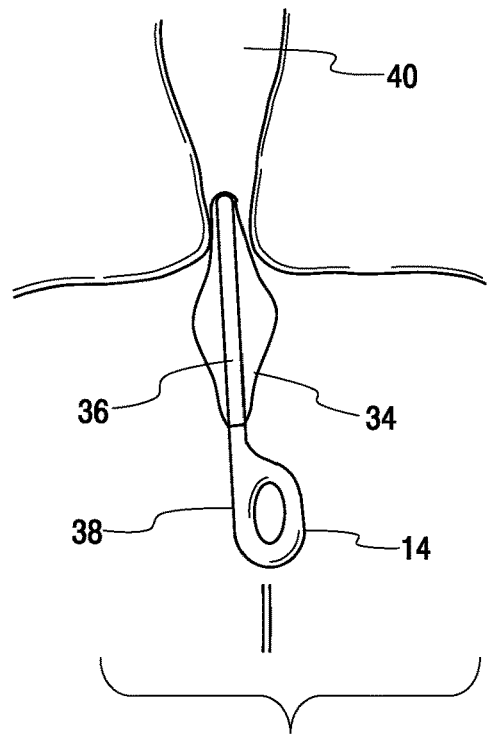

FIG. 1 shows an overview of a first embodiment of a trans-anal irrigation system 10 in accordance with the present disclosure. As shown in FIG. 1, system 10 may include a disposable, fillable or expandable irrigation head 12 which is easy to insert and remove from the body. Attached to the head 12 may be a guide member such as a gripping ring 14. A slide controller 16 for the pressure irrigation system may include an on/off release switch 18. A first irrigation tube 20 may be adapted to fluidly connect the head 12 to the controller 16. A second irrigation tube 22 fluidly may be adapted to connect the slide controller 16 to a large scale, rigid fluid supply 24. A fluid supply 24 may include a reservoir 26 which is removably mounted in a base 28. The base may include an easy to pump pressurizing feature having a pump button 30 that allows the user to pump and pressurize fluid for irrigation and pumping into the bowel. Fluid reservoir 26 can be easily removed from the base 28 for easy filling of the reservoir. The fluid reservoir 26 contains a suitable irrigating liquid. Typically the irrigating liquid may be water, possibly with additives mixed with the water. It will be understood that other fluids may be used as an irrigating liquid and references herein to water as the irrigating liquid do not limit the irrigating liquid to water alone.

The system 10 preferably includes easy-to-use and operate features to help with the insertion of the irrigation head into the body. For example, an easy filling design, a simple pressure pre-pumping and a simple on/off controller design may be provided. Guide member 14 is easy to grasp and hold during use. The styling and construction of the system allows the user to simply set up and utilize the system for TAI needs. Also the system can discreetly be kept next to the toilet as it will blend into the environment of the home bathroom.

FIG. 2 details a view of the liquid fillable, disposable irrigation head 12 for insertion into the body. Irrigation head may be shaped similar to current balloon designs to comfortably enter, hold, and be retained in the initial opening of the bowel. Disposable irrigation head 12 may have a liquid filled chamber 32 defined by a flexible bulb 34. The bulb should be sufficiently flexible that the liquid contained inside the chamber 32 can be easily displaced during insertion and removal from the body. Bulb 34 may surround a relatively rigid conduit 36. At its distal end the conduit 36 may be sealed to the bulb 34, thereby preventing fluid communication between chamber 32 and the conduit 36. At its proximal end the conduit 36 may be in fluid communication with a passageway (not shown) through the interior of a rigid fitting 38. The first irrigation tube 20 may be removably connected to the opposite end of the fitting, in fluid communication with the passageway, as indicated by arrow A. The exterior of the fitting 38 may carry a guide member 14.

FIGS. 3A, 3B, 3C and 3D detail a view of the irrigation head insertion/removal sequence. Liquid (e.g., oil) may displace within the chamber 32 during insertion and allow the bulb 34 to be easily inserted and conform to the shape of the bowel 40. This removes the need for separate inflation and deflation mechanisms as the liquid may be used to hold the product during use or permit its removal upon completion of irrigation. Different head shapes may be used.

Figure 4:
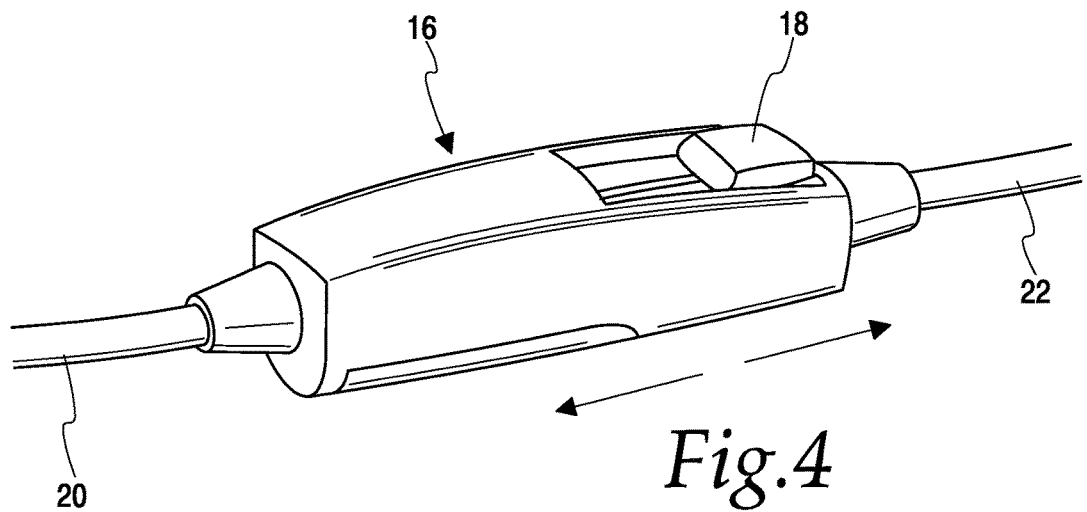
FIG. 4 is an enlarged view of the slide controller of the embodiment of FIG. 1.

FIG. 4 illustrates the easy to operate in-line slide controller 16 for use with the TAI system 10. This in-line controller allows the user to easily grasp and slide the large release switch 18 in the direction of the arrows to turn the flow from the irrigation liquid supply 24 to the irrigation head 12 on and off. The in-line slide controller 16 promotes a more intuitive device for use. The controller can be easily wiped down/cleaned for use on multiple occasions.

Figure 5:
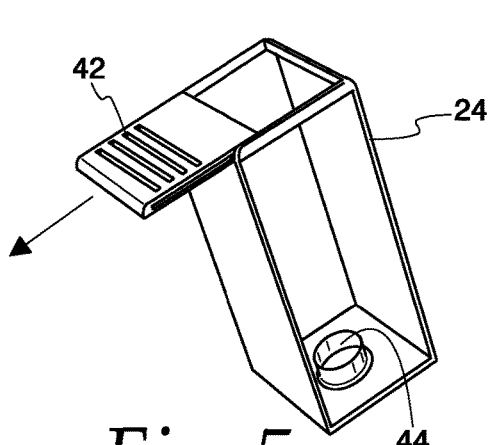
FIG. 5 is a perspective view of the reservoir removed from the base and with its top cap open.
Figure 6:
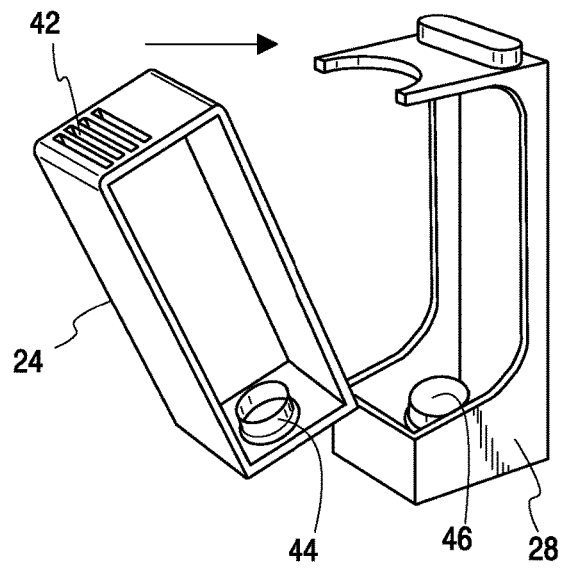
FIG. 6 is a perspective view of the fluid supply, illustrating the replacement of the reservoir into the base.

FIGS. 5 and 6 illustrate the reservoir filling sequence and the set-up of the irrigation liquid supply for pressure usage. The reservoir 26 may include a large easy to open slider top cap 42 which will allow the user to readily open and fill the reservoir with the designated amount of irrigation liquid for the TAI process to be conducted. The bottom of the reservoir 26 may include a shut-off valve 44 which is closed when the reservoir is out of its base 28. Once filled, the reservoir may be replaced in the base 28. The base may include a projection 46 which fits into the shut-off valve 44 when the reservoir is installed in the base to open the valve and permit irrigation liquid to flow from the reservoir to a short hose (not shown) in the bottom of the base. This hose may be connected to the second irrigation tube 22.

Once the reservoir is filled and replaced on the base 28, the user will typically press down a number of times on the pump button 30 to prime and pressurize the system for use. This will pump the irrigation liquid (e.g., water) into the hose and second irrigation tube 22 and prime the system for use. The user now has the system ready for use and can easily transfer to the toilet and insert the irrigation head 12 into the rectum comfortably. With the system primed and the irrigation head inserted into the rectum, the user may slide the release switch 18 on the controller 16 to permit water to flow into the inserted irrigation head 12 through the use of pressure pumping. The user may have the water supply 24 positioned in front of them while seated on the toilet and turn off the controller 16 when the designated amount of flow is reached.

With the water introduced into the body the user may simply engage the guide member (e.g. gripping ring) 14 on the irrigation head and slowly retract the irrigation head 12. Retraction will displace the oil in the bulb 34 and remove the irrigation head from the body. The bulb 34 and fitting 38 may be disposed of. The first and second tubes 20, 22, the controller 16 and water supply 24 may be stored, ready for multiple subsequent uses.

TAI systems disclosed herein address usability and ease of use concerns for the SCI user while using a TAI bowel care program. Many individuals may find insertion of the irrigation head, product set-up, product holding, controller interaction and water pumping into the body difficult and, at times, intimidating. The present systems address all of these concerns in an easy-to-use product solution. Pressure irrigation, simple operation controllers and auto retain/removal heads simplify the TAI process and allow the user to utilize a more intuitive, ready-to-use system for their TAI needs.

Particular advantages of the systems disclosed herein include, but are not limited to, the oil-filled displacement head which allows for reduced intimidation and easy insertion/removal of the irrigation head into and out of the rectum during and after use. The user-friendly design and clean aesthetic allow for a more intuitive device and easier training and use of the product by the SCI user. The water conduit can be easily removed/loaded and pumped allowing the set-up procedure to be more efficient and easier to undertake. Components made of rigid, polymeric materials can easily be wiped down and cleaned for retention after use and storage for multiple uses. The simple controller will allow the user more control over the system and simplifies the overall system design.

Figure 7:
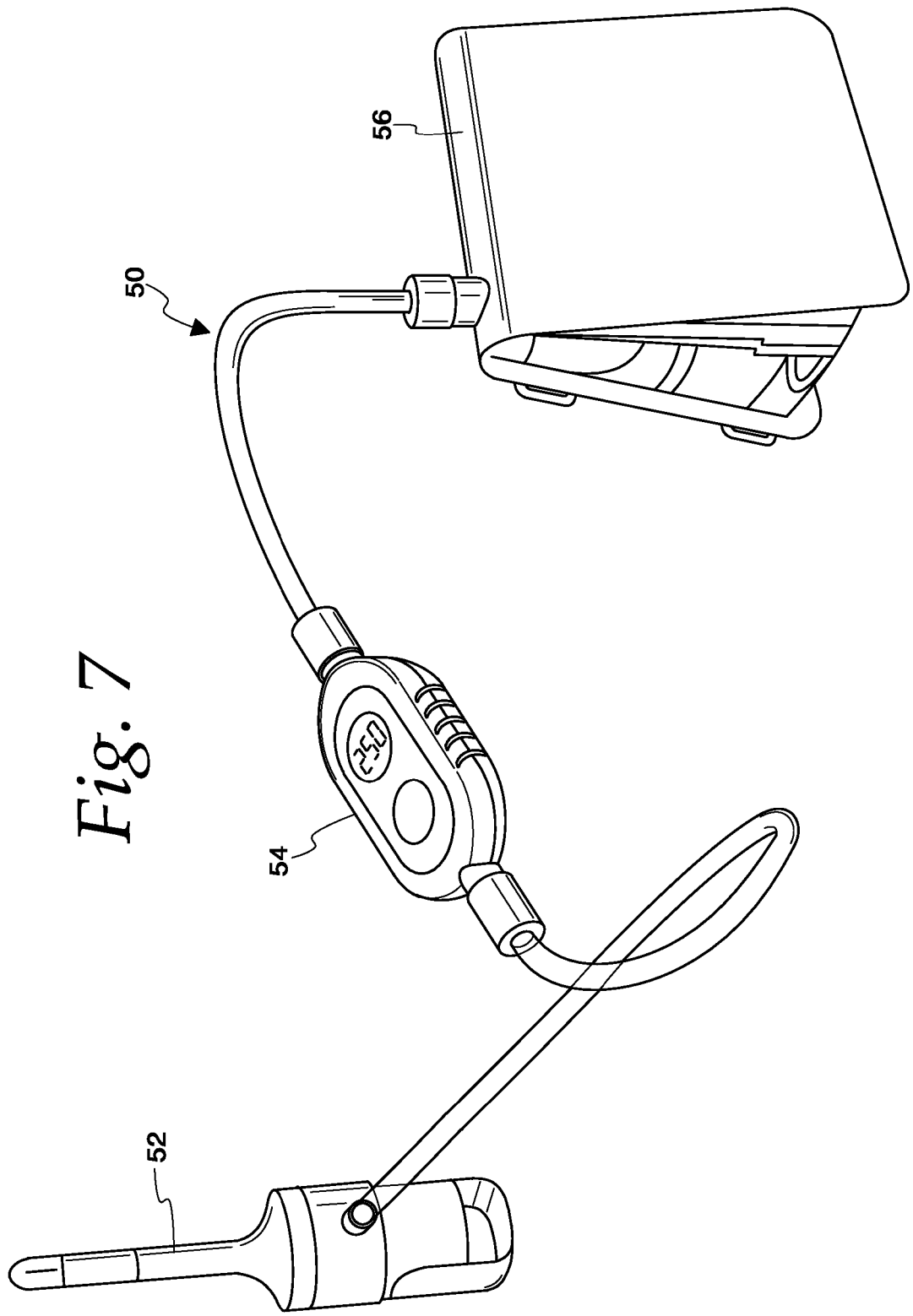
FIG. 7 is a perspective view of a second embodiment of a TAI pressure system of the present disclosure.

FIG. 7 shows an overview of the TAI platform solution 50 of the present disclosure. Body interface 52 features a pre-filled inflation balloon for secure retention and is Intuitive, provides one handed-insertion and removal of the device in a single use option. The user interface/controller 54 features a battery-powered pump with a large ON/OFF switch controller, Simple, intuitive controls and an easy-to-read volume display indicate to the user the amount of flow in mls of water loaded into the bowel. The water management device 56 details a water bag with a robust design and a siphon pump that doesn't need to be elevated, and has easy-to-open connections. This enables an easy-to-use and train design, an ergonomic and less bulky design for storage and a device that is intuitive and logical to understand with the simple ON/OFF switch for hands free pumping.

The embodiment of FIG. 7 provides an intuitive, battery-powered irrigation system. The body-interface is inserted and inflated in a simple motion and the easy to read digital interface allow the user to easily control the flow rate and volume regardless of hand function. The disposable balloon catheter is removed from packaging, connected to the system and inserted into the anus. The rectal IC is preloaded with air or gel similar to that of a syringe device.

An in-line digital controller allows the user to customize the flow rate. The rectal balloon is retracted and deflated and the catheter is removed from the anus, thus facilitating evacuation of faecal matter. The motorized system enables hands-free, controlled pumping of water into the body in a simple easy to use system. The rectal catheter is disposed of and the controller and pump are retained for future use.

Figure 8:
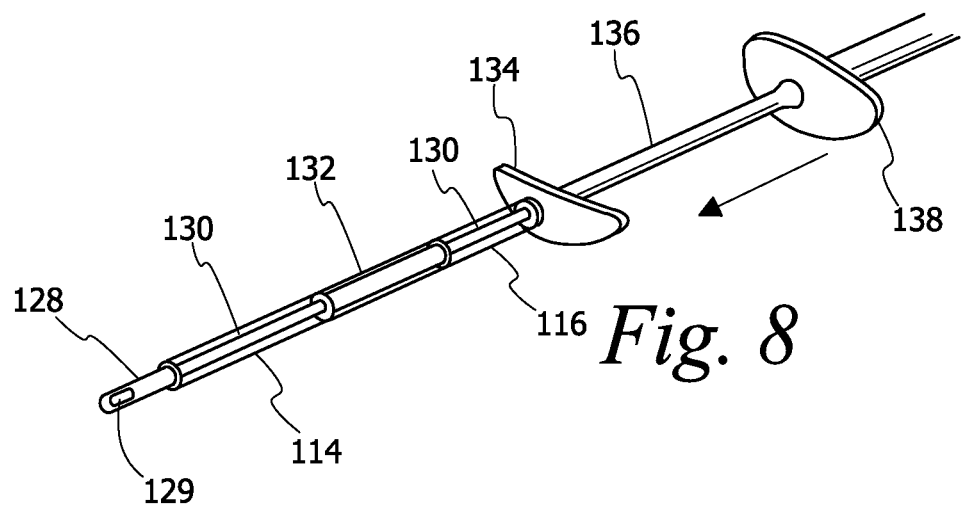
FIG. 8 is an enlarged perspective view of an alternate irrigation head suitable for use in connection with various TAI systems, such as either FIG. 1 or FIG. 7, with the irrigation head in its non-deployed or retracted condition.
Figure 9:
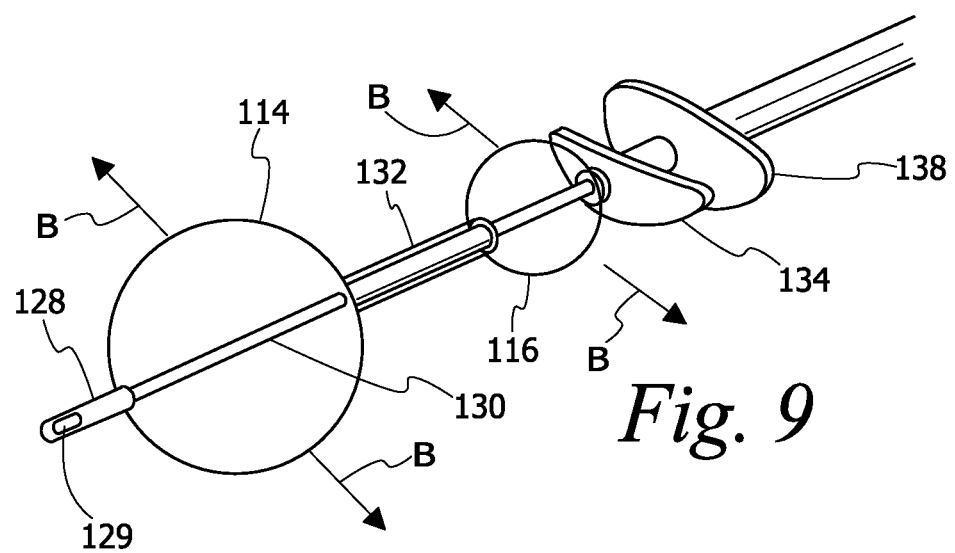
FIG. 9 is an enlarged perspective view of the irrigation head of FIG. 8 with the irrigation head in its deployed or extended condition.
Figure 10:
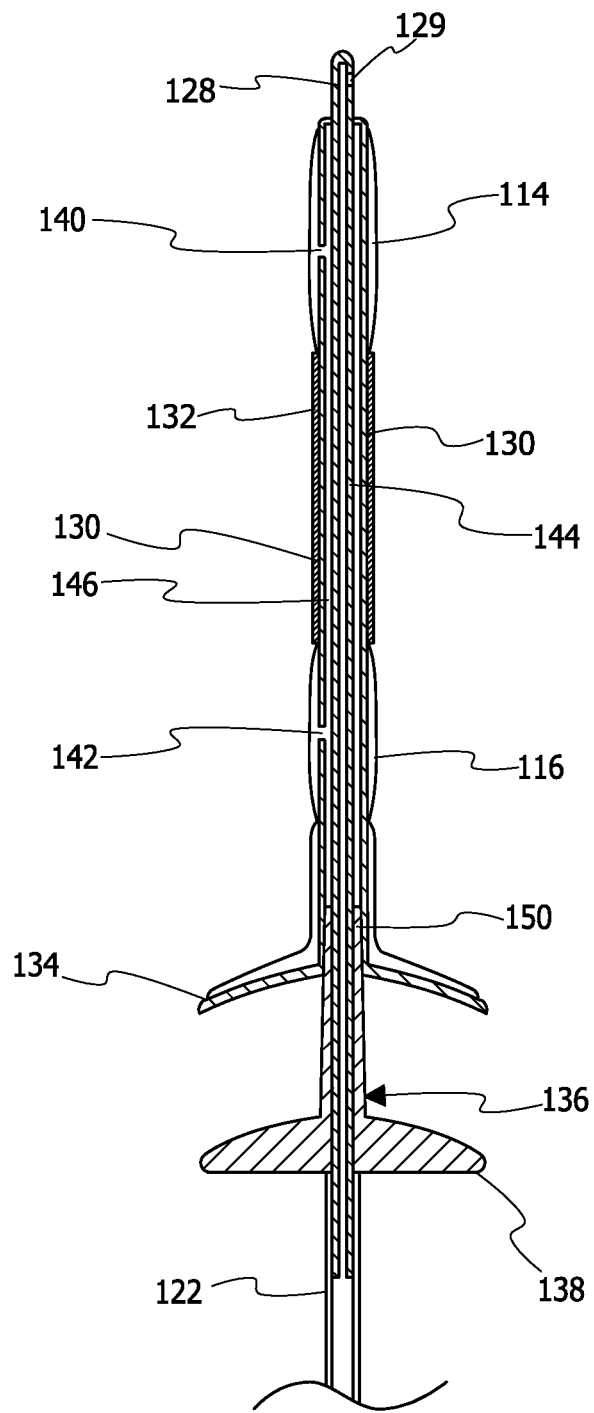
FIG. 10 is a diagrammatic section view of the barrel and plunger of the irrigation head of FIG. 8.

FIGS. 8-10 illustrate details of an alternate auto retention irrigation head 112 for use with the system 50 in place of the body interface 52. The head 112 may be provided on a syringe-like device with a fluidly-isolated central conduit or tube extending therethrough. With reference to FIGS. 8 and 9, exterior portions of the head 112 can be seen. Starting at the proximal end (i.e., the end that enters the rectum), there is visible on the exterior a hollow tip 128, a barrel 130 (visible through the translucent outer balloon 114), a spacer sleeve 132 which surrounds the barrel, the barrel 130 again (visible this time through the translucent inner balloon 116), a flange 134, a plunger 136 and a press pad 138 affixed to the plunger. The outer balloon 114 may be sealed at its proximal end to one or both of the tip 128 and barrel 130, while the distal end of the outer balloon may be sealed to one or both of the barrel 130 and sleeve 132. Similarly, the inner balloon 116 may be sealed at its proximal end to one or both of the sleeve 132 and barrel 130, while the distal end of the inner balloon 116 may be sealed to one or both of the barrel and flange 134. The hollow interior of the tip 128 may communicate with the exterior via one or more radial ports, one of which can be seen at 129.

Looking now at FIG. 10, the internal construction of the irrigation head 112 can be seen. Note that for clarity the tip 128 and sleeve 132 are not shown in FIG. 10. The barrel 130 may be a hollow conduit with radial ports 140 and 142 through its outer wall. The ports 140, 142 may be axially located such that they are aligned with the inner and outer balloons 116 and 114, respectively. The flange 134, which may be integrally formed on the exterior of the barrel, may be mounted to the distal end of the barrel 130. The proximal end of the barrel 130 may include in its interior a central conduit or tube 144. Conduit 144 may provide a flow path through the barrel 130. The proximal end of the barrel 130 may be sealed so fluid cannot escape from an annulus 146 surrounding the conduit 144 within the barrel 130. The proximal end of the conduit 144 may also be sealed to the barrel 130 so that water cannot flow from the conduit 144 into the annulus 146 and the interior of the conduit 144. However, the interior of the conduit 144 may open to the exterior of the barrel 130. Water or other irrigating liquid can flow through the conduit 144 to the hollow tip 128. The central conduit 144 may be removably connectable at its distal end to the first irrigation tube 122.

The plunger 136 may have a hollow shaft 150 which preferably fits snugly into the annulus 146 between the barrel 130 inside wall and the outside wall of the conduit 144. The annulus 146 may be filled with a fluid, such as air, water or oil. This fluid may be used to inflate the balloons 114, 116. The distal end of the shaft 150 may carry the press pad 138. Due to the tight fit between the shaft 150 and the barrel 130, when a user draws the press pad 138 and shaft 150 into the barrel, fluid is forced out of the annulus 146, through the ports 140, 142 and into the balloons 114, 116, thereby inflating the balloons as noted by the arrows B in FIG. 9. This will remove the need for pumping and inflation of the balloons and the user may load/deploy the balloons after inserting the end of the device into the body before use.

Figure 11B:
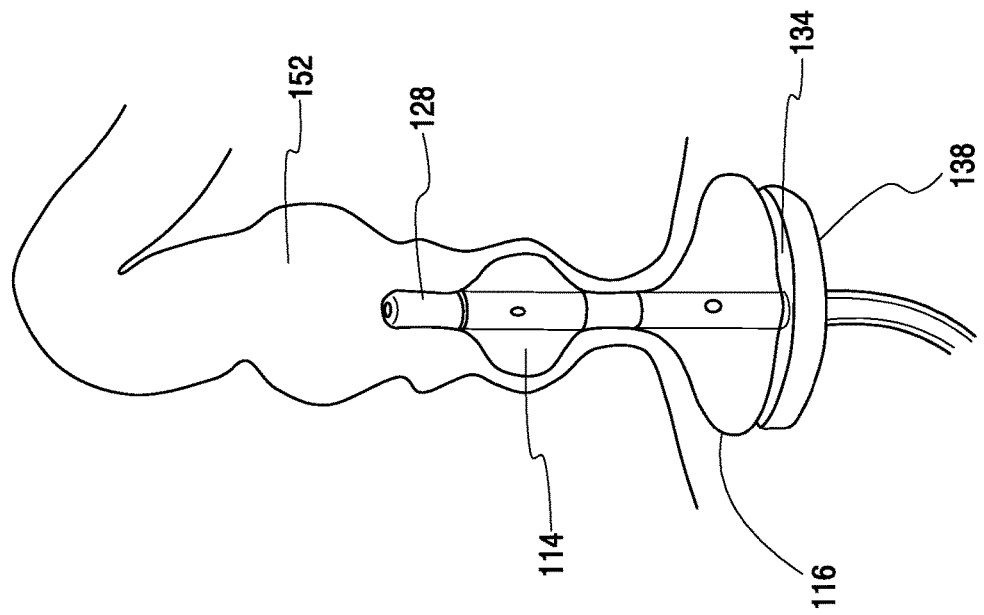
FIGS. 11A and 11B are diagrammatic sections illustrating insertion of the irrigation head of FIGS. 8 and 9.
Figure 11A:
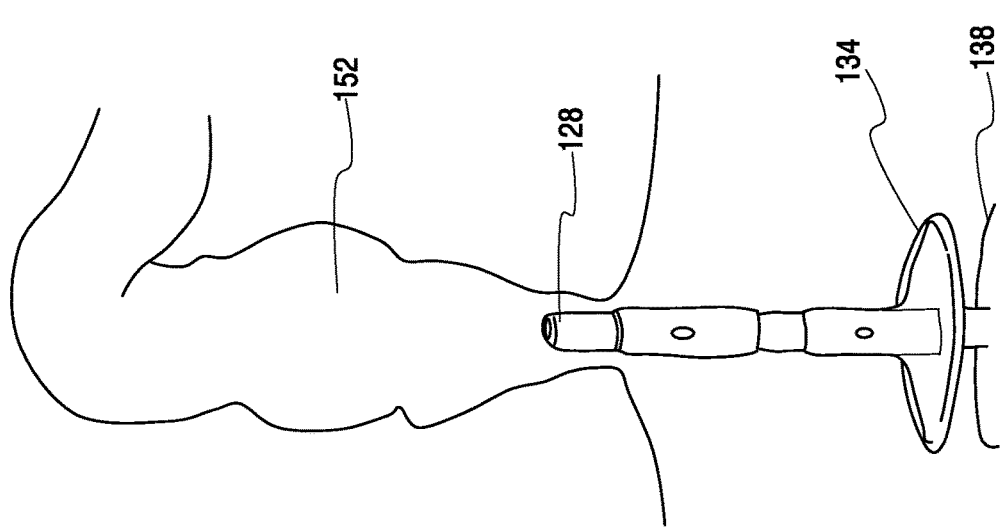

FIGS. 11A and 11B detail the loading and inflation of the irrigation head 112 during insertion. First, the user inserts the tip 128 of the irrigation head into the bowel. The bowel is shown by the outline 152. Once the balloon 114 is fully inserted, the user may draw on the press pad 138 to load and draw the preloaded material (oil, gel etc.) into the dual silicone balloons 114, 116 to deploy the device. With the press pad 138 deployed as shown in FIG. 11B, fluid will inflate the balloons and the inflated inner balloon 114 will be deployed inside the user. Inflated balloons 114, 116 will seal the rectum and close off the bowel to enable TAI and water induction into the bowel.

The outer balloon 116 may include retaining features such as an adhesive coating to aid in the holding of device on the outside of the body. Outer balloon 116 will typically be held outside the body and seal the exterior of the bowel in conjunction with the inner balloon 114 to dual seal the bowel and prevent excess leakage of material during TAI use. Similar to a syringe, the plunger may be advanced to inflate the inner and outer balloons 114, 116. The inflation method may use air, water or oil to fill the balloons. Inasmuch as the plunger may be preloaded with a set amount of fluid, upon plunger insertion the balloons 114, 116 will inflate to a set inflation limit.

Figure 12:
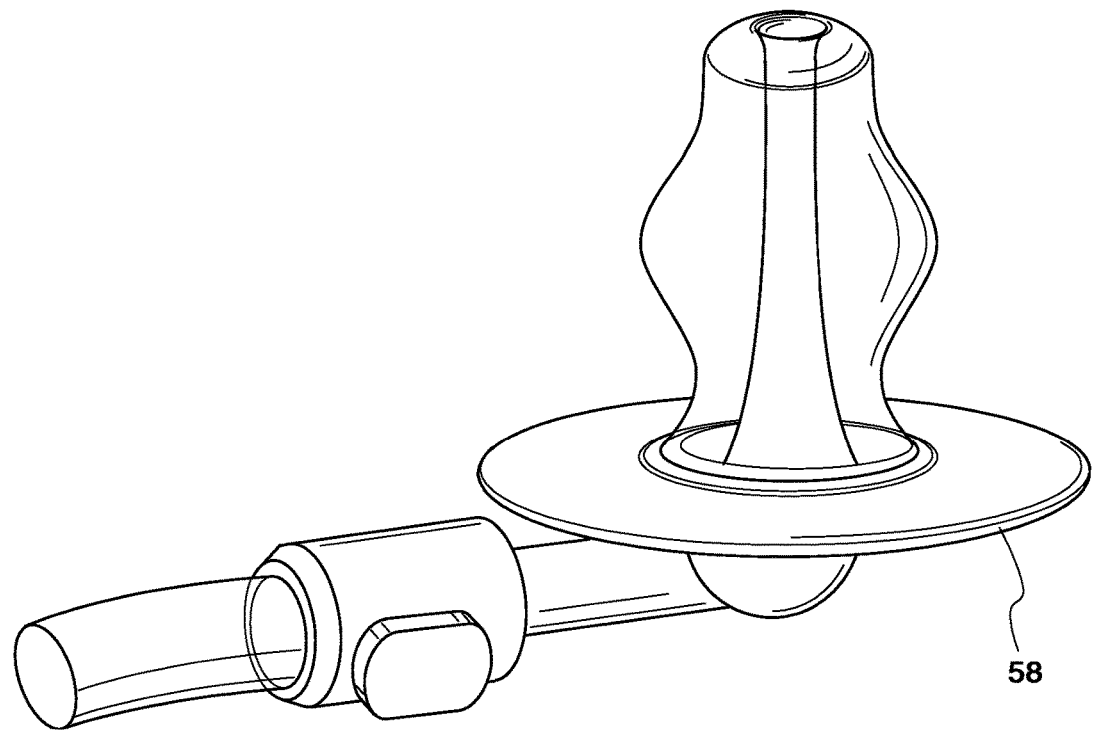
FIG. 12 is a perspective view of an alternate irrigation head.

FIG. 12 illustrates yet another alternate embodiment for use as the body interface in TAI platform solution 50. A cone head 58 could be used. This is a shaped cone head section with a soft silicon head formation to which a retention feature may be added.

In the embodiment of FIGS. 7-12, the motorized pump may allow the user of limited dexterity to insert the head, turn on the irrigation system to pump and draw a set amount of water into the body, without the need for manual pumping and effort to conduct their TAI needs. The use of this system will decrease product set-up time and simplify the overall TAI process. The oil-filled plunger may alleviate concerns and apprehension stemming from insertion/removal of the irrigation head into and out of the rectum during and after use. The user will simply insert the head and after insertion the balloons will be deployed to hold the irrigation head in the opening of the bowel. The simple design and clean aesthetic allow for a more intuitive device, allowing for easier training and use of the product by the SCI user. The water conduit can be easily removed/loaded and pumped allowing the set-up procedure to be more efficient and easier to accomplish. Alternately, a simplified manual pump device may replace the motored in-line pump to allow the user to utilize manual pumping of the water into the body if needed (e.g. batteries for the motor may run out or the system may not operate).

Furthermore, the pump device and irrigation liquid storage component may feature insulation materials to retain and regulate the set degree of irrigation liquid temperature (e.g., water needs to be at body temp. to conduct TAI efficiently). The in-line pump may feature a small heater element to allow regulation of water temperature. Water from the source (cold water) may be drawn to the pump and heated to the set temperature and pumped into the body during the automatic TAI process.

As in the previous embodiment, the present device can be used in the user's bathroom as the design will blend into the bathroom environment due to the simple design aesthetic and natural color schemes. Components made of rigid polymeric materials can easily be wiped down and cleaned for retention after use and storage for multiple uses. The simple controller will allow the user more control over the system and simplifies the overall system design. Use of the simple in-line motor allows for a controlled amount of water to be introduced to the bowel which can be easily operated by the user during TAI. Also, the entire system can be retained and reused and only the purchase of single-use, disposable irrigation heads need be undertaken by the user.

Figure 13:
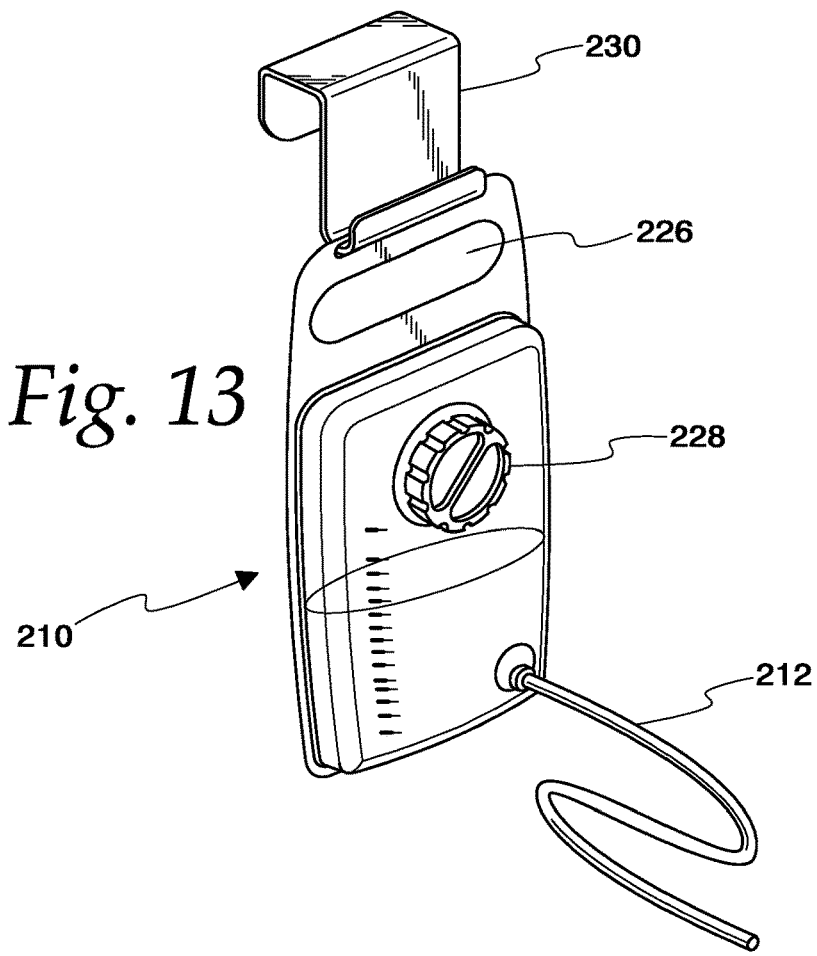
FIG. 13 is a perspective view of a gravity feed water source in an additional embodiment having a modular head system.
Figures 14, 15:
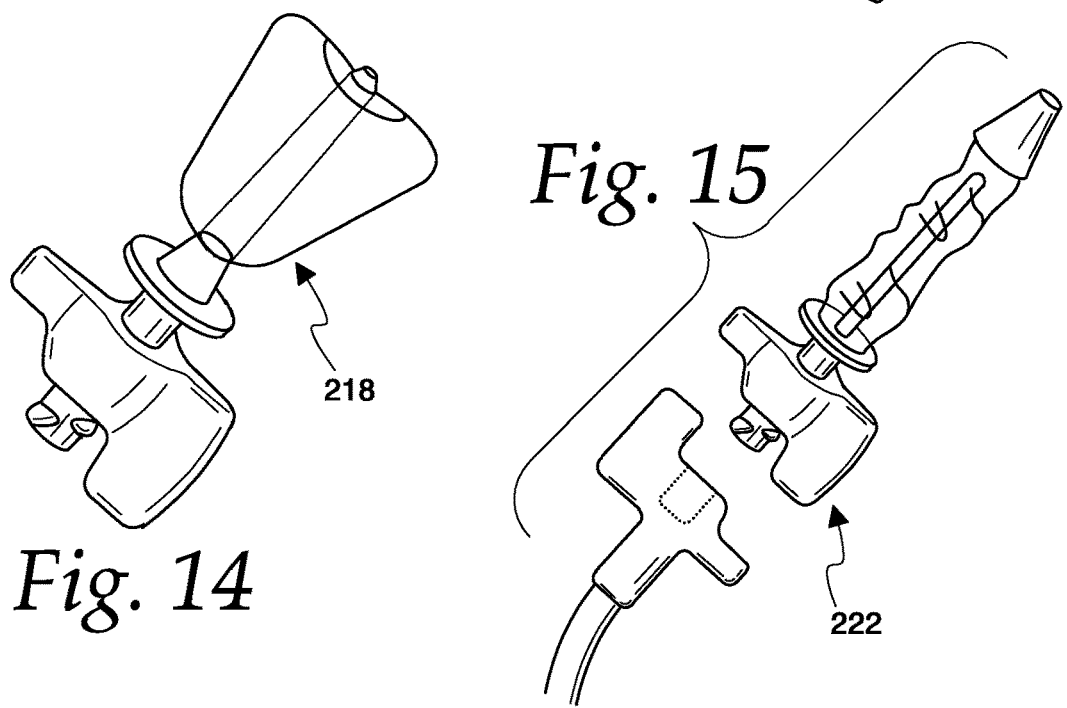
FIG. 14 is a perspective view of a water filled balloon irrigation head for use in a modular head system.
FIG. 15 is a perspective view of an insertion inflation irrigation head for use in a modular head system.
Figure 16:
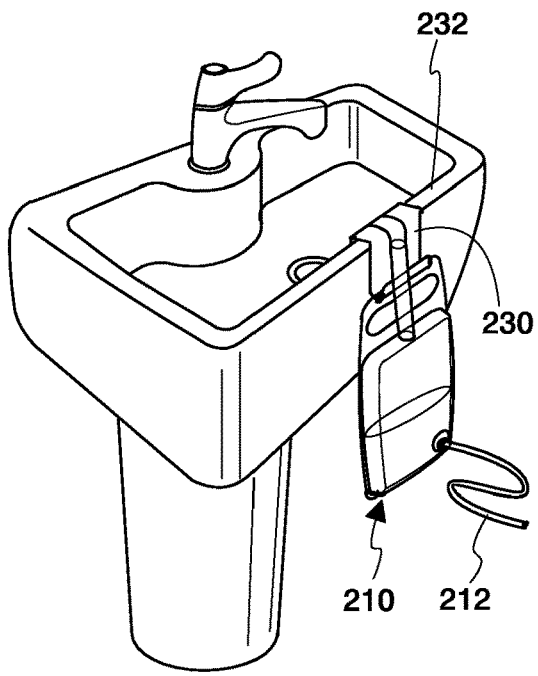
FIG. 16 is a perspective view of the hanging bag of FIG. 13 mounted on a sink.
Figure 17:
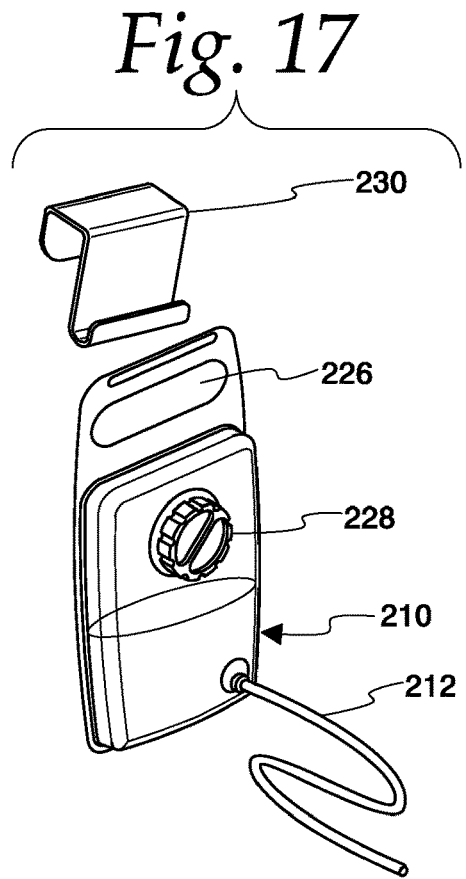
FIG. 17 is a perspective view of the hanging bag of FIG. 13 and a hanger for mounting the bag on a sink.
Figure 18:
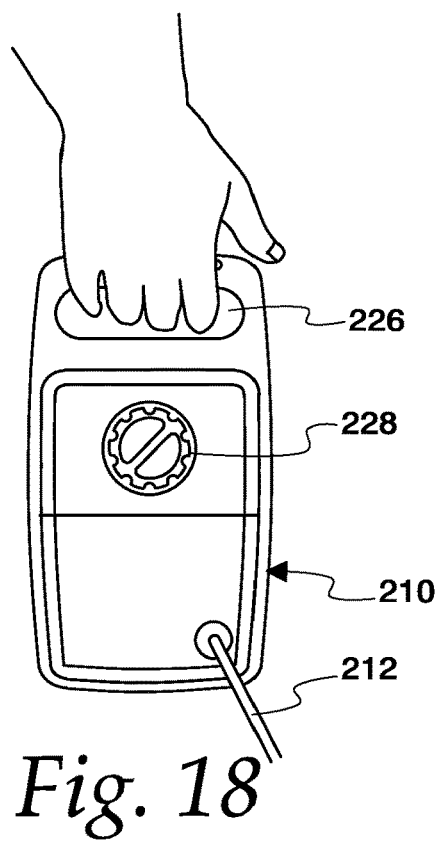
FIG. 18 is a front elevation view of the hanging bag of FIG. 13, showing the carrying handle.
Figure 19:
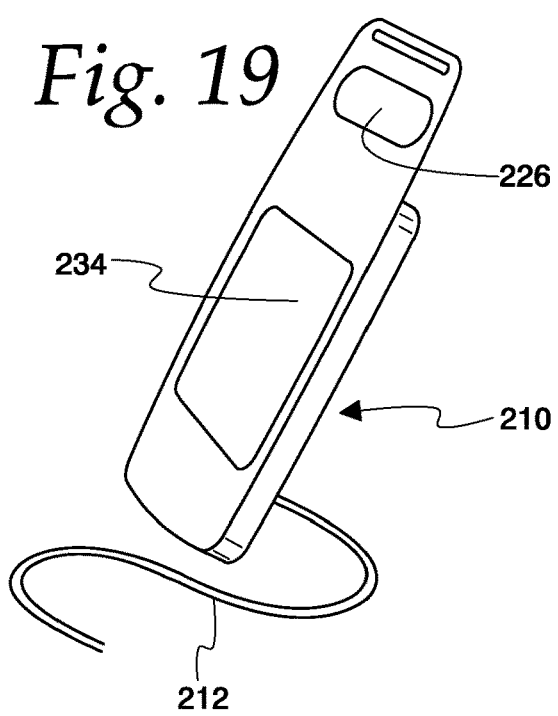
FIG. 19 is a perspective view of the back or rear side of the hanging bag of FIG. 13 showing the adhesive backing.
Figure 20:
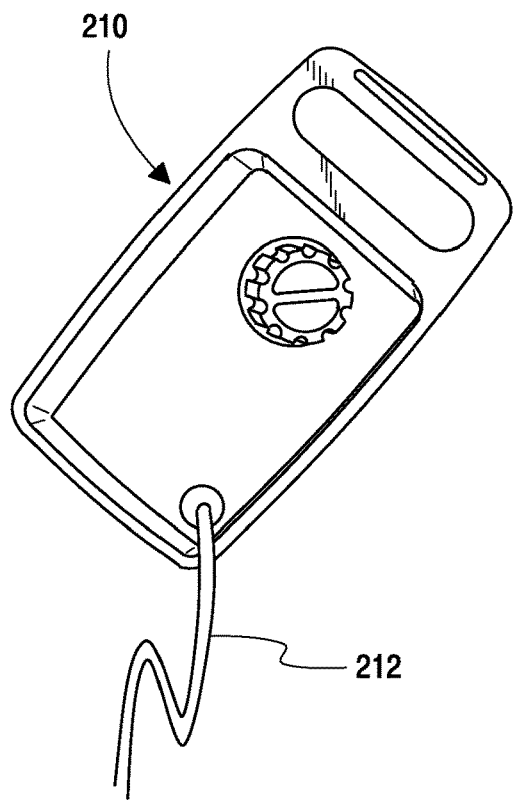
FIG. 20 is a perspective view of the hanging bag of FIG. 13 mounted on a wall by the adhesive backing.
Figure 21:
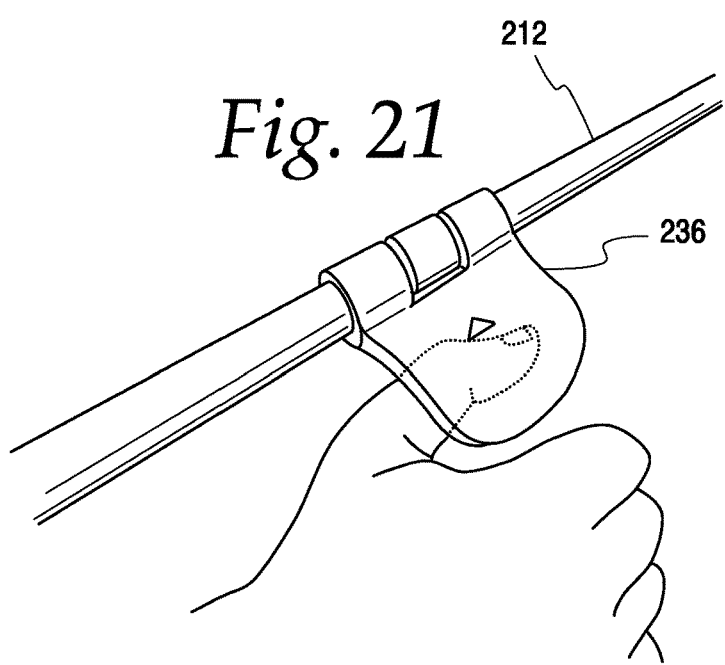
FIG. 21 is a perspective view on an enlarged scale of a clip valve on the irrigation tube.

FIGS. 13-15 illustrate yet another embodiment of the TAI systems of the present disclosure, namely, a modular TAI system and the components for use. The modular system may include a gravity feed water supply utilizing a hanging bag 210 and an irrigation tube 212 connecting the bag to one of a plurality of modular Irrigation heads. This makes the modular system suitable for use by different users such as limited dexterity users, stoma patients, and clinicians. Irrigation heads include a water filled balloon 218 (FIG. 14) and an insertion inflation head 222 (FIG. 15).

FIGS. 16-21 illustrate the features of the hanging, gravity-feed water supply bag 210. The hanging bag 210 may include a large holding handle 226, a large easy to open top cap 228 and adhesive fixture options. A sink hanger 230 can be hooked to the bag 210 and secured to the lip of a sink 232 to hold the filled bag during TAI usage with the modular head system. Adhesive backing 234 present on the irrigation bag allows the filled bag to be filled and secured for gravity irrigation usage of the device at a height. Large clip valves 236 may be used in-line to control gravity flow of water. Flow may be sent from the bag, through the irrigation tube 212, and to one of the chosen elemental modular irrigation heads 214-224.

Figure 22:
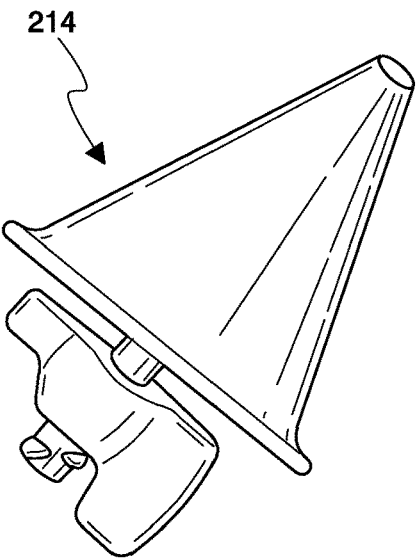
FIG. 22 is a perspective view of a stoma irrigation head for use in a modular head system.
Figure 23:
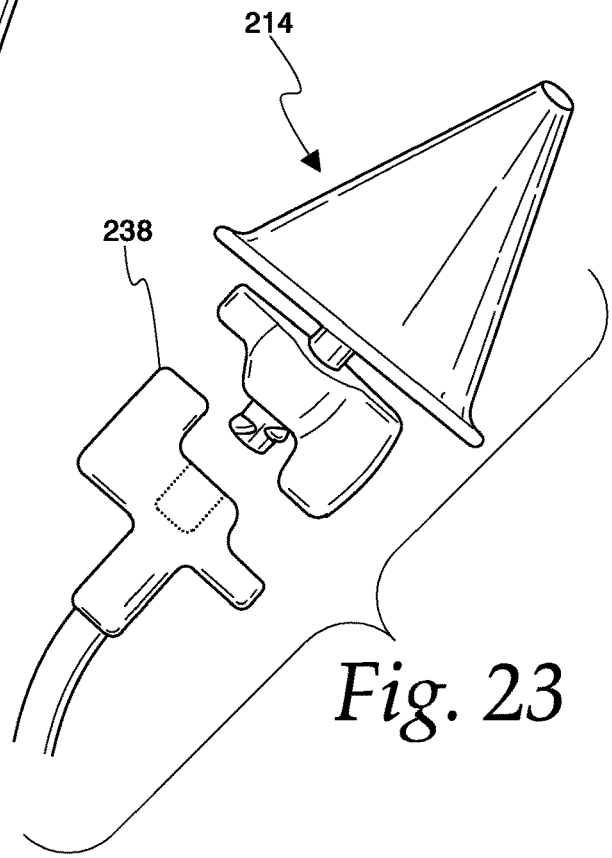
FIG. 23 is a perspective view of a stoma irrigation head and a connector on an irrigation tube about to be attached to the head.
Figure 24:
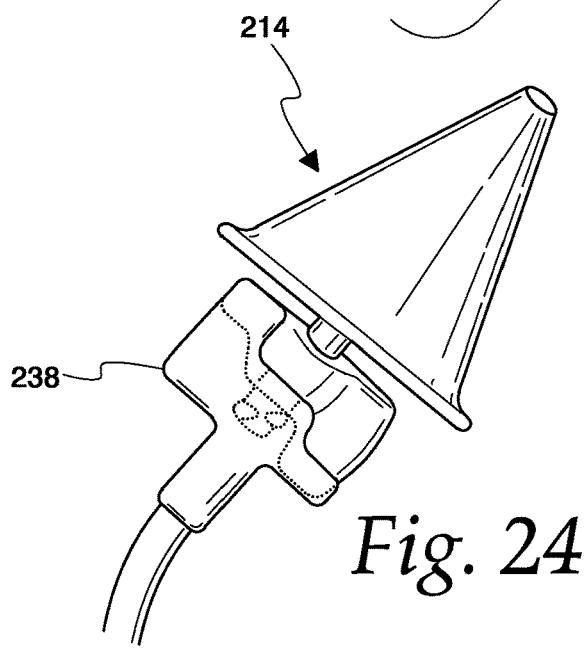
FIG. 24 is a perspective view of a stoma irrigation head after attachment of a connector on an irrigation tube.

For use by users with stomas or MACE procedures, the user may purchase a system with stoma irrigation heads, such as those available from Hollister Incorporated, of Libertyville, Ill., for use with the gravity filled irrigation bag 212. The user may purchase multiple heads but just a single water source and irrigation tube. The multiple heads may be utilized with the standard bag and valve systems. As seen in FIGS. 22-24, the system may include large, threaded Luer-lock style colored connectors 238 to allow for secure and easy insertion/removal of the heads.

Figure 25:
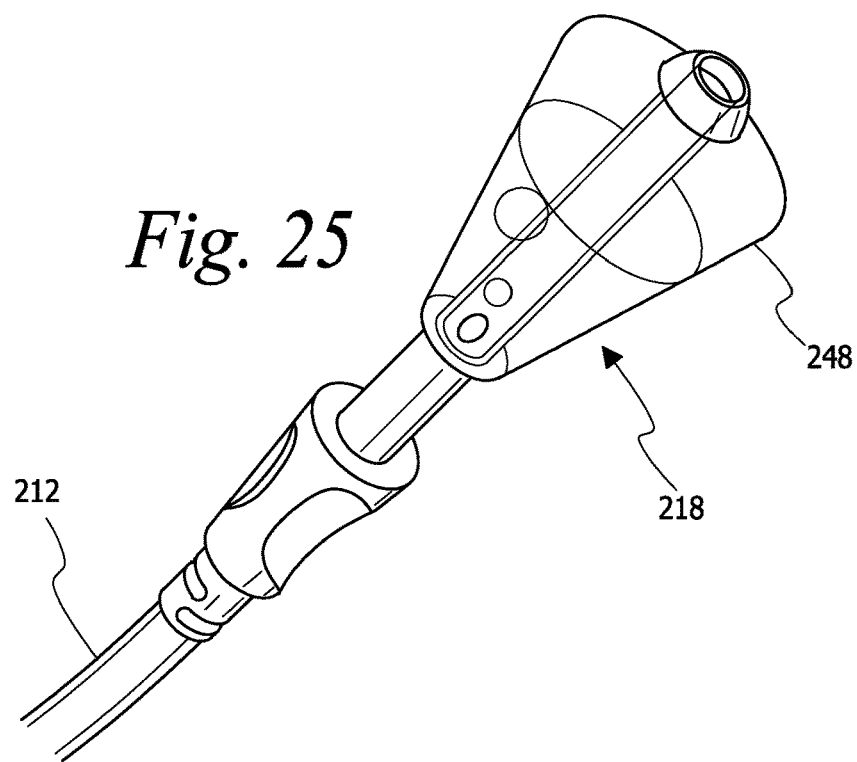
FIG. 25 is a perspective view of a water filled balloon irrigation head.
Figure 26:
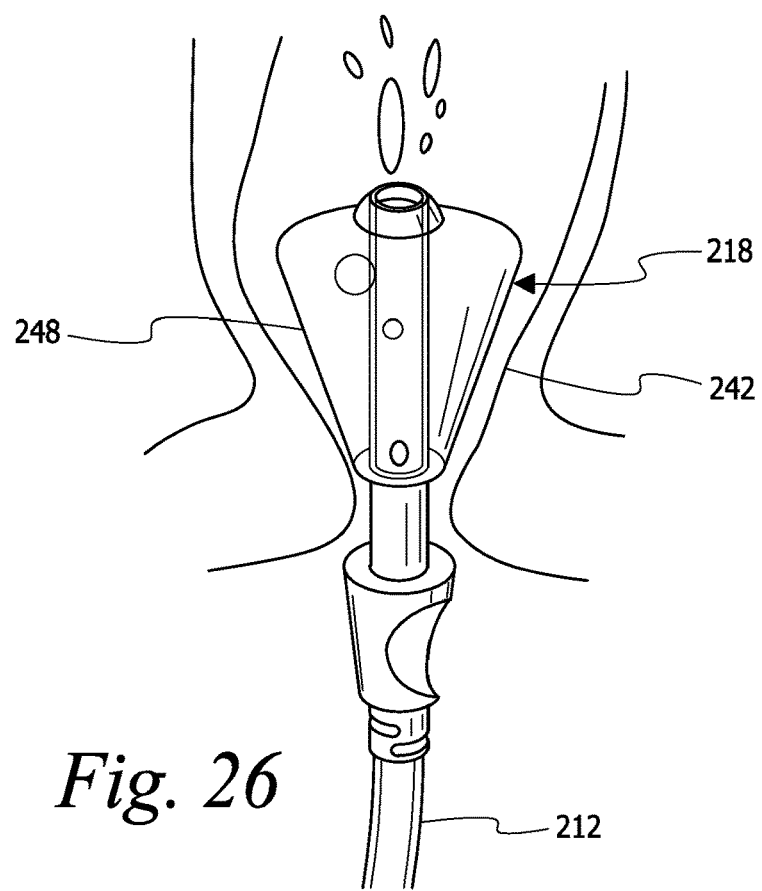
FIG. 26 is a diagrammatic section showing the water filled balloon irrigation head of FIG. 25 in use.
Figure 27:
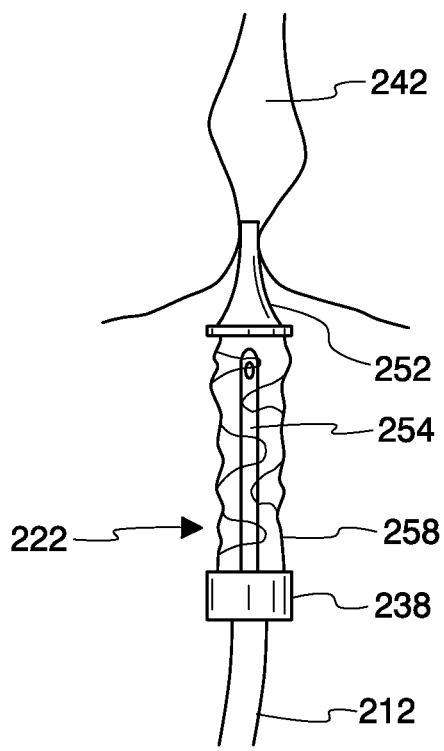
FIG. 27 is a diagrammatic section showing the insertion inflation head of FIG. 15 in an initial stage of insertion.
Figure 28:
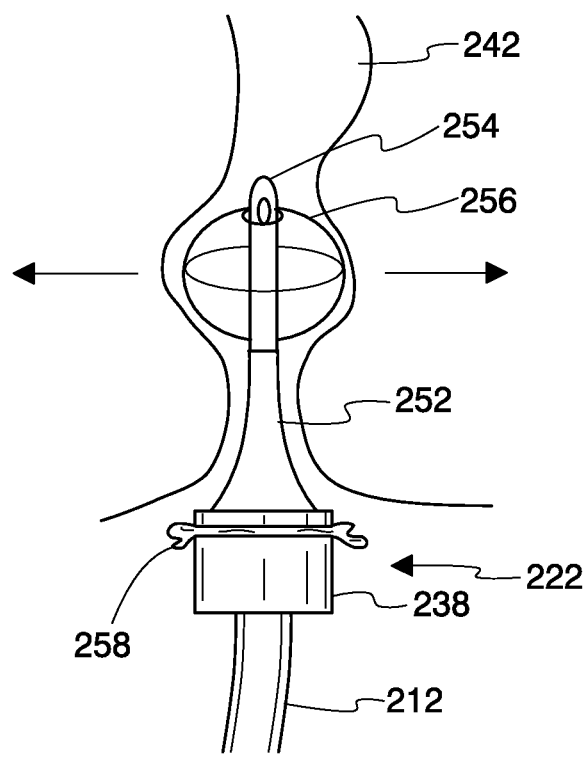
FIG. 28 is a diagrammatic section showing the insertion inflation head of FIG. 15 in use.
Figure 29:
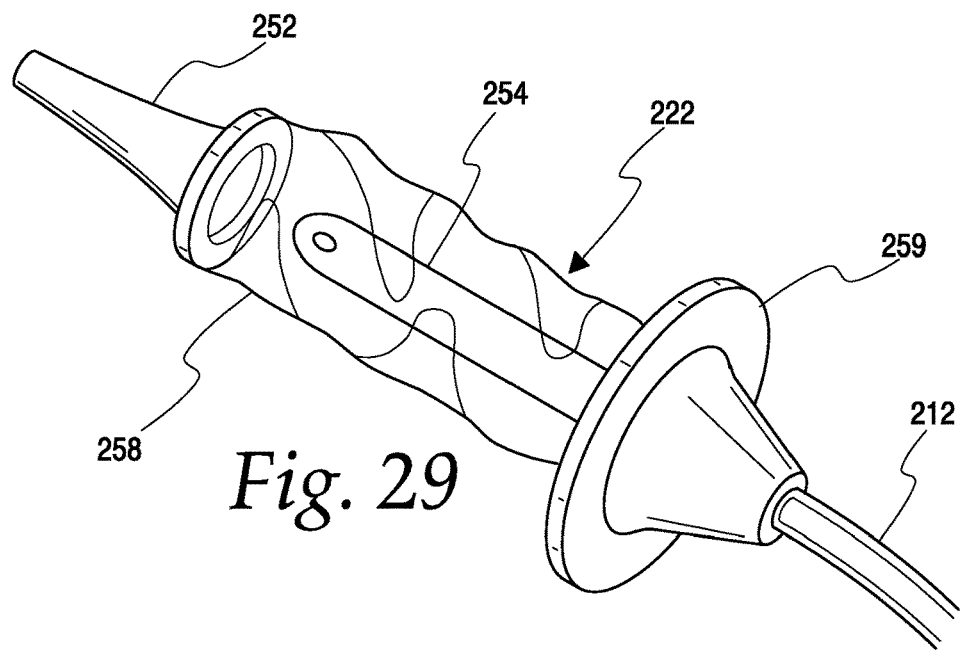
FIG. 29 is a perspective view of the insertion inflation head of FIG. 27.
Figure 30:
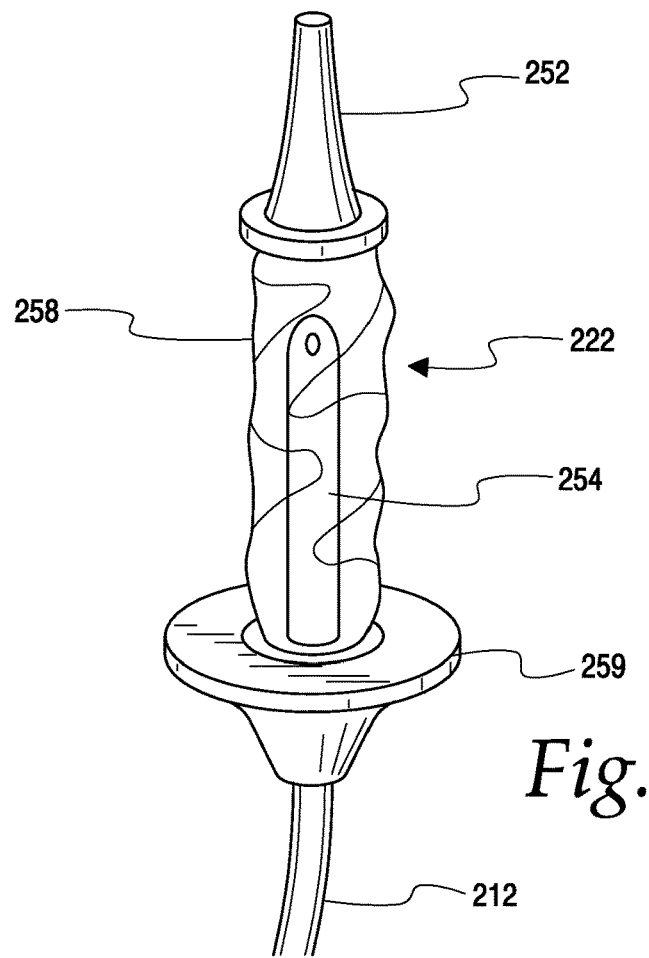
FIG. 30 is a perspective view of the insertion inflation head of FIG. 27.
Figure 31:
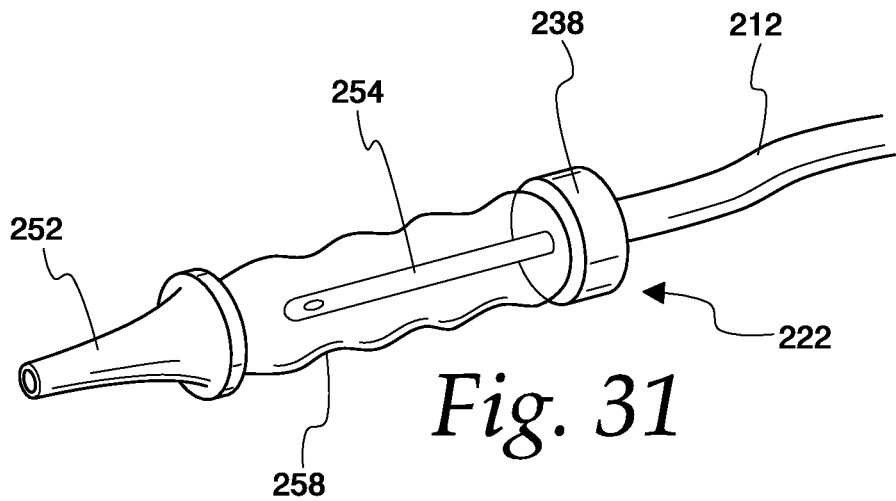
FIG. 31 is a perspective view of the insertion inflation head of FIG. 27.
Figure 32:
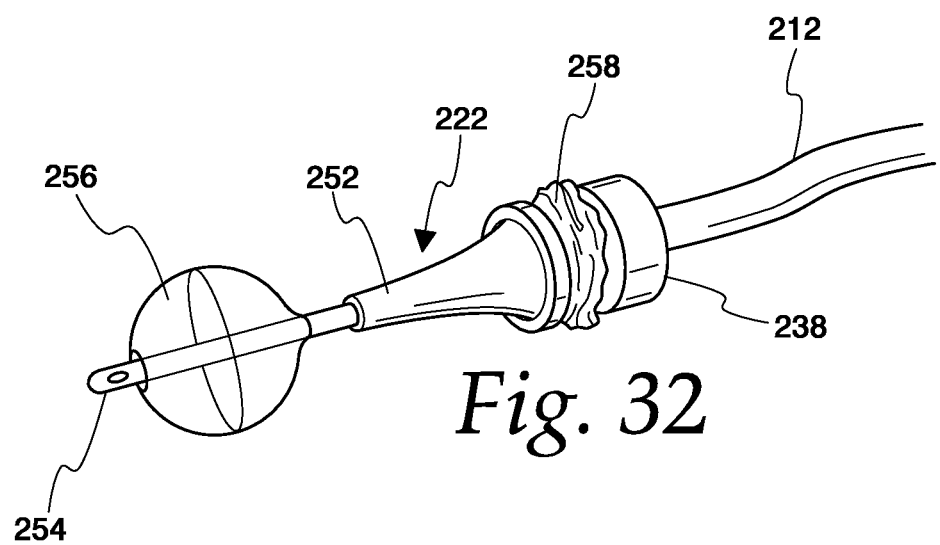
FIG. 32 is a perspective view of the insertion inflation head of FIG. 31 with the sleeve collapsed.

The liquid filled irrigation head 218 is shown in FIGS. 25 and 26. This balloon style irrigation head has an inflatable balloon 248 which expands during the irrigation process. As the user pumps liquid into the balloon 248, it fills with liquid until deployed. The user then diverts irrigation to the irrigation head into the body. The liquid filled balloon alleviates feelings of intimidation and fear of air filled balloons and more particularly, concern for over-pressurizing the balloons with air (such that bursting of the balloon may occur). The balloon may be shaped to act as a lug to conform the device to the inner channel of the bowel. Also, during the removal of water from the system the balloon will simply flush out of place.

An insertion inflation irrigation head 222 is illustrated in FIGS. 15 and 27-32. This cone/balloon hybrid may include a small scale insertion cone 252. Upon insertion a rectal catheter 254 will enter and expand the pre-loaded balloon device 256 inside the body. This affords a reduced intimidation factor compared to current designs as inflation occurs during the insertion process of the catheter into the body. An external sleeve 258 acts as a protective sheath over the catheter 254. The sleeve is attached to a flange 259 (FIGS. 29 and 30), which in turn is connected to a Luer-lock connector 238. The sleeve 258 will make insertion clean. With the TAI process complete the device will be pulled and the balloon 256 of the insertion inflation head will deflate and retract. Upon removal the balloon will be retracted over the unclean catheter 254 and into the external sleeve 258 for clean disposal after use.

In this embodiment the various styles of irrigation heads described above can be mixed and matched to each specific user to provide the user with options and a range of irrigation features to choose from when utilizing the irrigation bag device to perform TAI procedure. This helps address the problems of prior TAI systems in terms of usability and ease of use for the SCI user while using the TAI bowel care program. As discussed above, for many individuals insertion of the irrigation head, product set-up, product holding, controller interaction and water pumping into the body may be difficult and/or intimidating. The features of the systems described herein address all of these concerns in an easy-to-use and/or user-friendly product solution. Irrigation heads can be mixed and matched to each specific user to give the users option and range of irrigation features to choose from when utilizing the simple gravity irrigation bag device to perform the TAI procedure.

A gravity feed system with large handles, hanging features, easy to open top caps and easy to open valves can be easily utilized by the SCI user to perform TAI and induce water into the bowel. The modular irrigation heads can be interchanged with the standard bag/tubing design to provide irrigation for a larger range of customer markets e.g. stoma users, TAI users, constipation, limited dexterity and clinician care giver.

The modular head system features assistive aids such as adhesive holding tabs, inflation insertion and closed collection, replacing current rectal balloons/cone systems and allowing the user variation in the choice of TAI product they wish to use. Easy to open and close valves allow for limited dexterity users to easily start and stop flow from the irrigation bag source. Easy to twist Luer-lock connectors allow the limited dexterity user to twist/release the product components during and after use. The gravity hanging bag can be utilized in different locations through the adhesive hanger or sink hanging feature. This allows the user to set up the TAI system for gravity irrigation of water into the bowel. Note—for gravity systems to work to the full extent, the bag must typically be placed two feet above the user's rectum. Finally, the cost of a gravity feed system will be cheaper compared to alternative irrigation systems such as pressure pumps and electric pumps.

Figure 33:
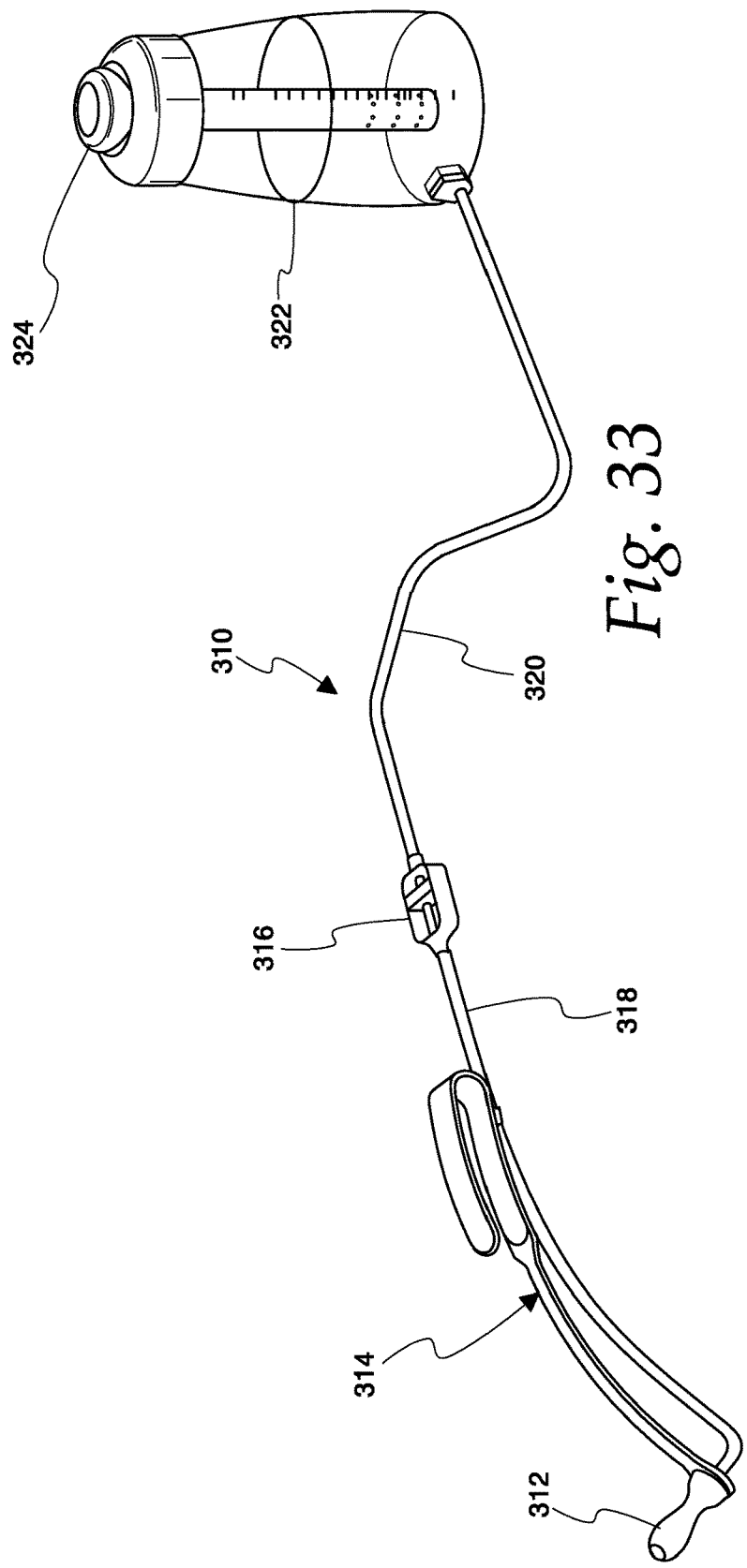
FIG. 33 is a perspective view of another embodiment of the systems disclosed herein, showing a TAI guide member system.
Figure 34:
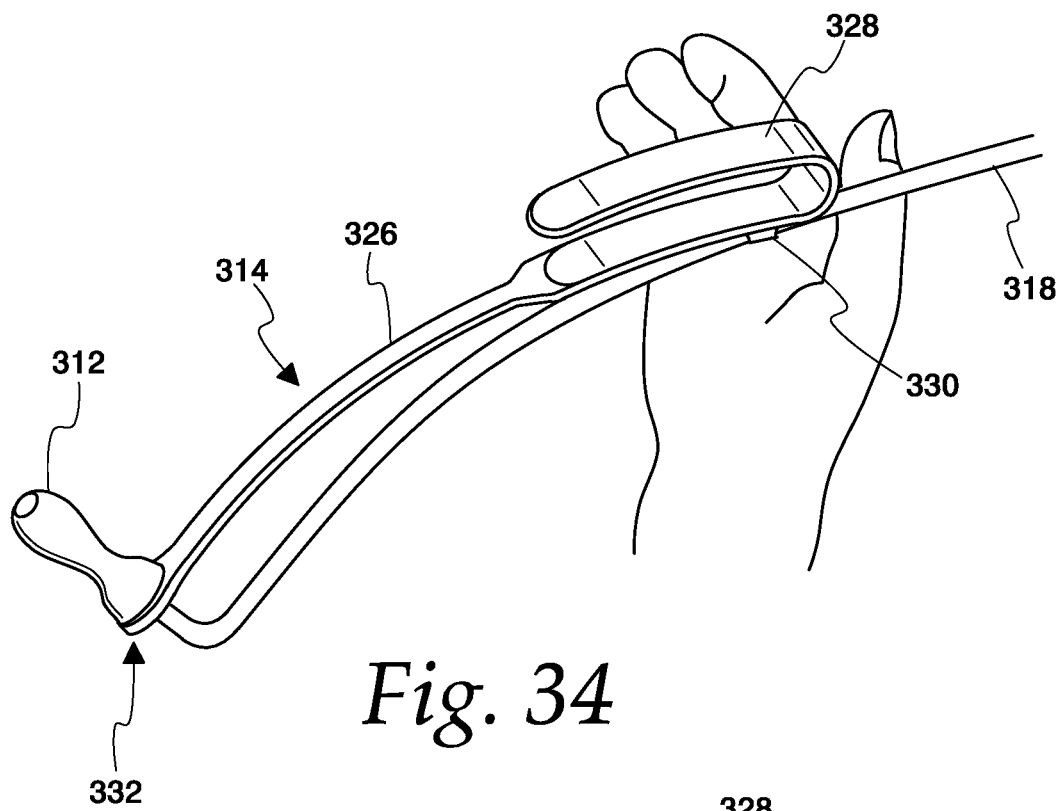
FIG. 34 is an enlarged perspective view of the guide member holding device of FIG. 33.
Figure 35:
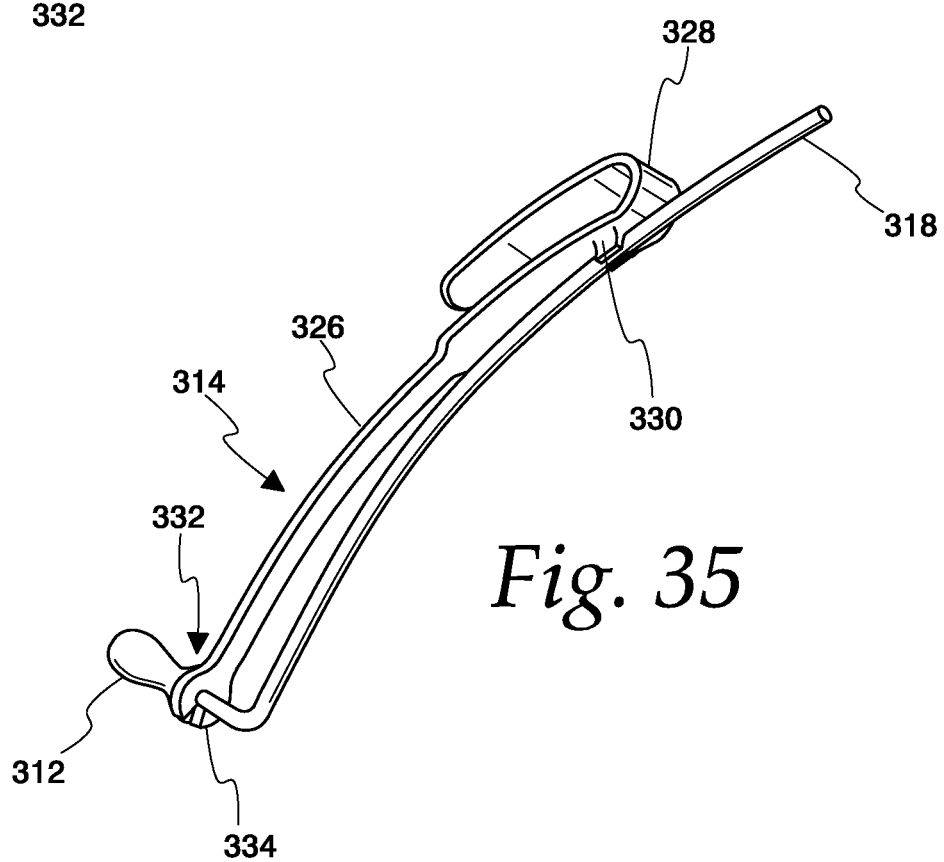
FIG. 35 is an enlarged perspective view of the underside of the guide member holding device of FIG. 34.

FIG. 33 illustrates an overview and image of another embodiment of an entire TAI irrigation system 310 according to the present disclosure. The components of the system 310 preferably include: a disposable, shaped irrigation head 312 for insertion into the rectum and holding of the device during use; a reusable guide member 314 for use by a user with limited dexterity to hold the head 312 during TAI; a pressure control switch 316 for turning water flow on and off; first and second irrigation tubes 318, 320; and an irrigating liquid supply including a large, water reservoir 322 to which is fitted a pump or pressurizing feature 324 to pump and pressurize liquid for irrigation and pumping into the bowel.

FIGS. 34-35 and 38-40 show the easy-to-clean guide member 314 that a user can retain and reuse over multiple TAI irrigation uses. The guide member 314 may include an elongated shank 326 which terminates at one end at a handle section 328. There may be a clip 330 on the underside of the handle for releasably engaging the first irrigation tube 318. The clip 330 allows user to clip the first irrigation tube 318 into place on the underneath of the guide member thus helping to organize and secure the tubing during TAI usage. At the end of the shank 326 opposite the handle 328 there may be an attachment element 332. The attachment element 332 may include an engagement member such as a fork 334 (FIGS. 35 and 38) which releasably engages the proximal end of the first irrigation tube 318. The attachment element 332 also may include an upstanding post 336 (FIGS. 38 and 39) on which the irrigation head 312 may be removably mounted. All of these features secure the insertion head and connected tubing and organize the irrigation tube during TAI use.

The guide member will enable the user to easily grasp and hold the irrigation head 312 between their legs while sitting on the toilet. The head 312 may be a soft shaped disposable irrigation head that may be easily held and secured to the end of the guide member 314 for the duration of irrigation use. The user with limited dexterity may place his or her hand into the handle section 328 to secure and extend the irrigation head 312 during irrigation. The reusable device may be made of a shaped polymeric material and can be easily cleaned and wiped down after use to enable the guide member to be retained for multiple uses.

Figure 36:
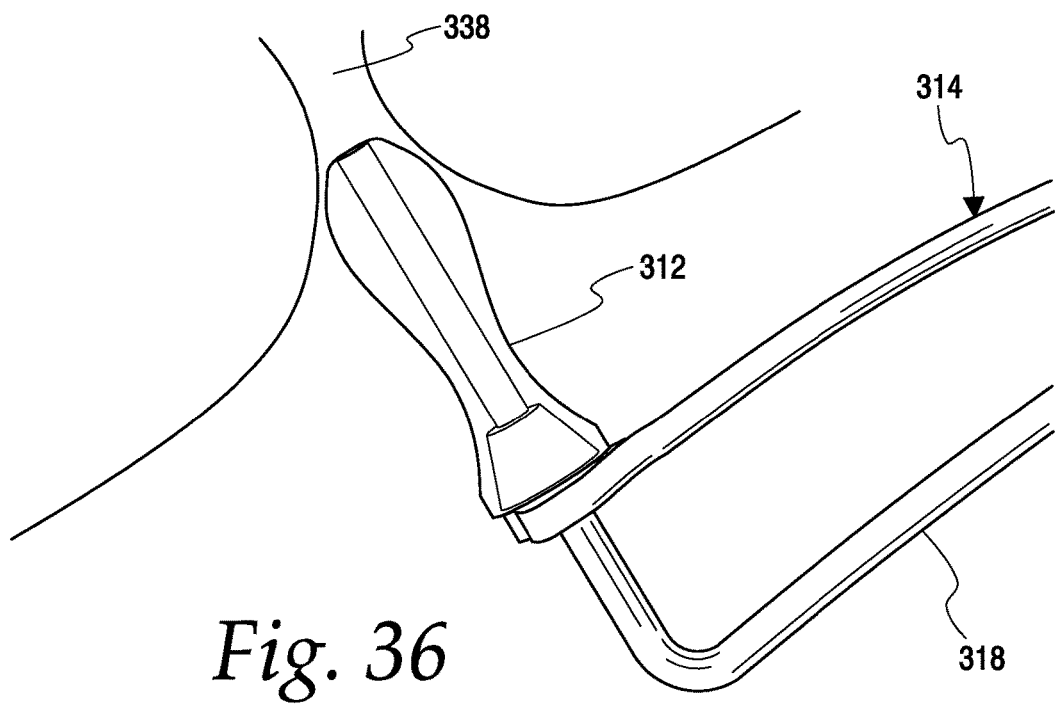
FIG. 36 is diagrammatic section showing initial insertion of the guide member system of FIG. 33.
Figure 37:
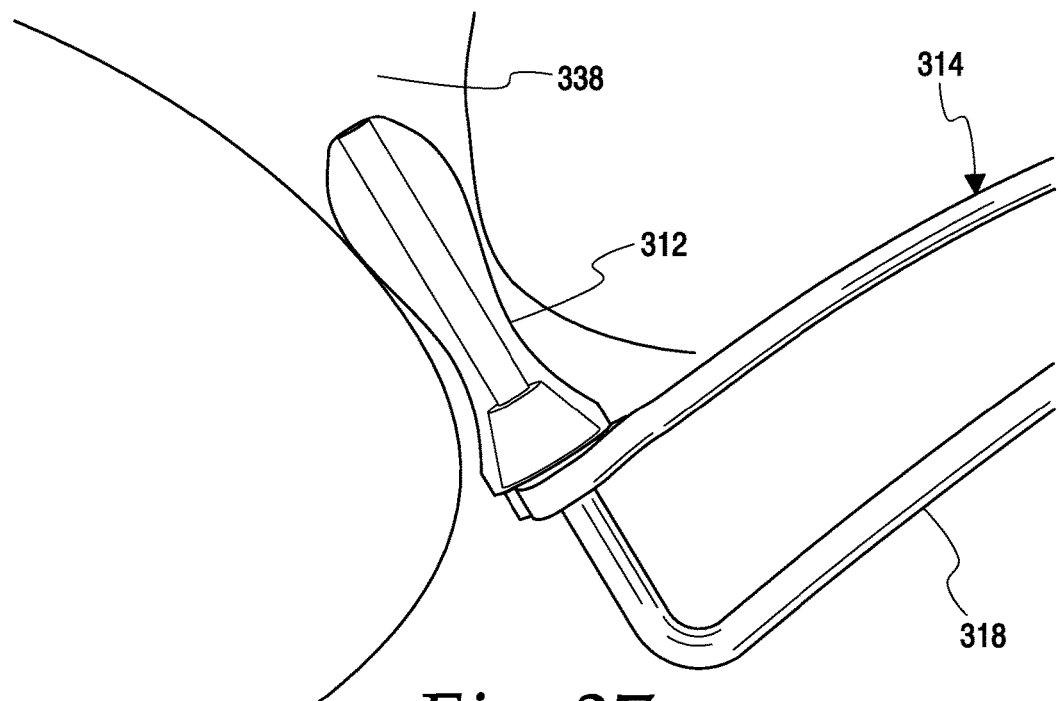
FIG. 37 is a diagrammatic section of the guide member system of FIG. 33 in use.
Figure 38:
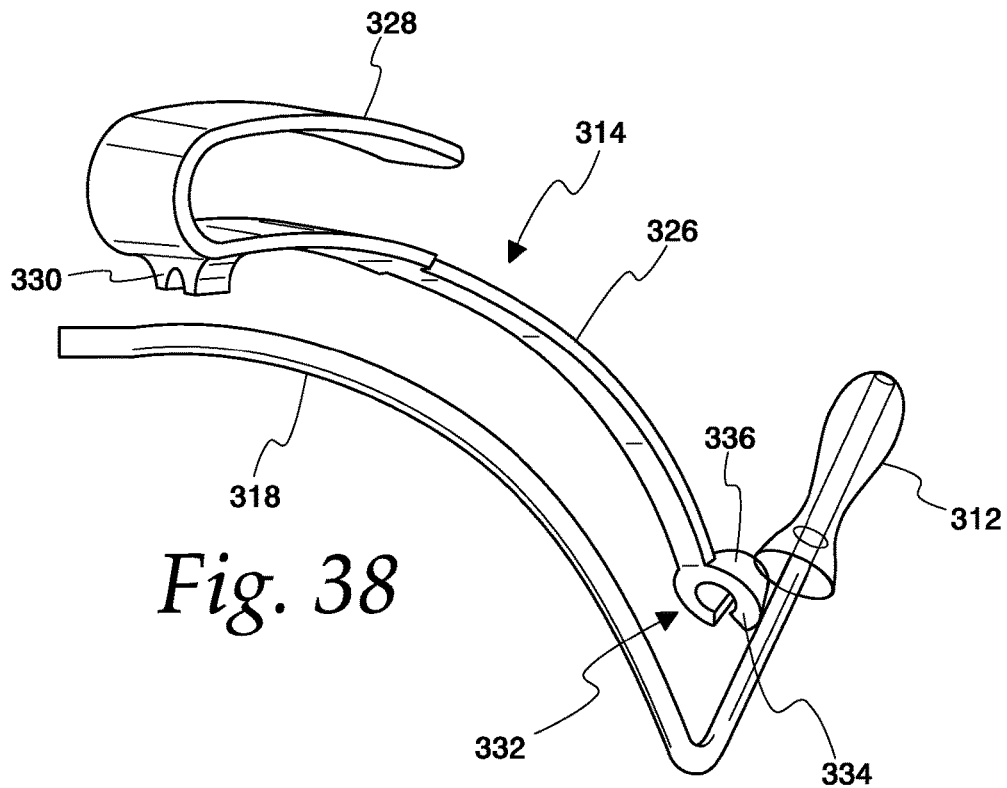
FIG. 38 is a perspective view showing the irrigation tube separated from the guide member holding device of FIG. 33.
Figure 39:
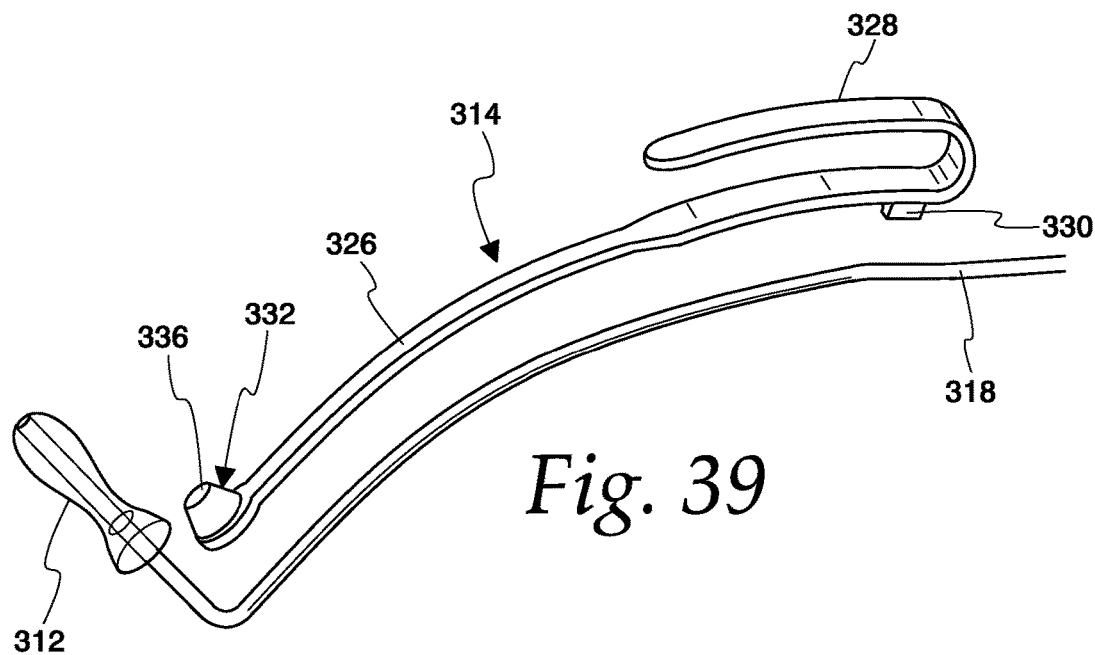
FIG. 39 is a perspective view showing the irrigation tube separated from the guide member holding device of FIG. 33.
Figure 40:
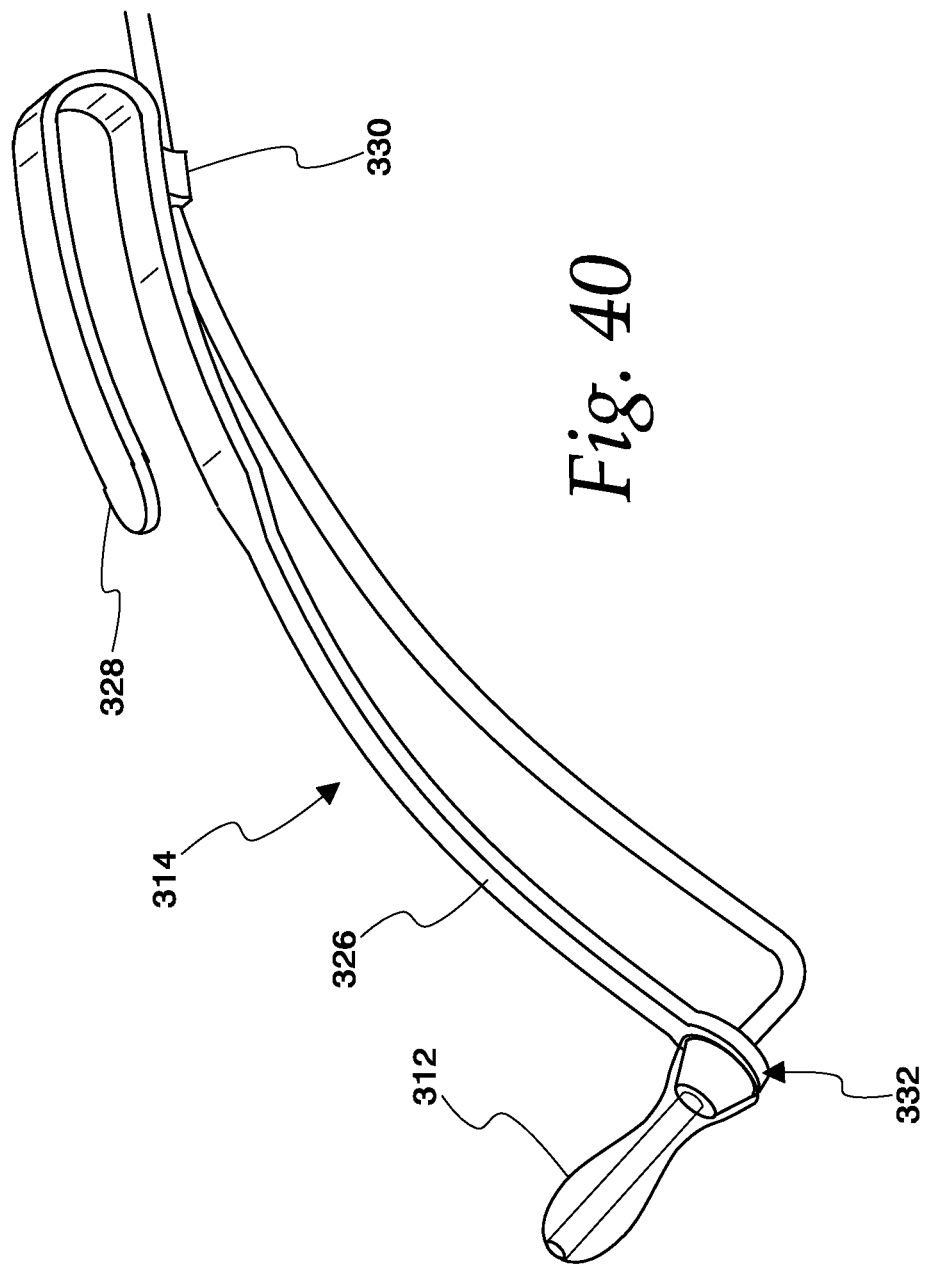
FIG. 40 is a perspective view showing the irrigation tube connected to the guide member holding device of FIG. 33 and ready for use.
Figure 44:
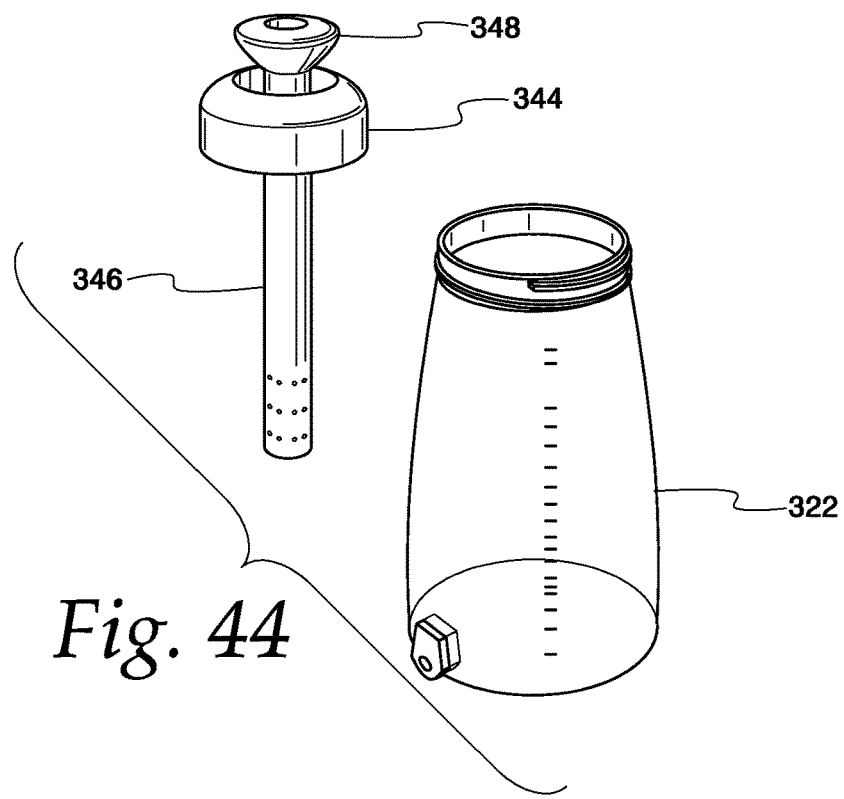
FIG. 44 is an exploded view of the irrigating liquid supply and pump.
Figure 45:
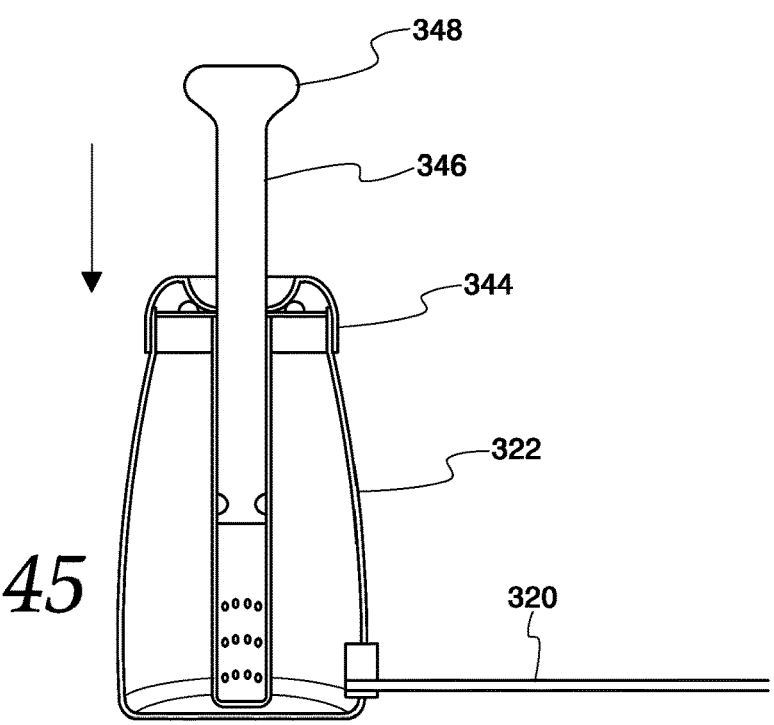
FIG. 45 is a section through the pump.

FIGS. 36 and 37 illustrate the use of the soft irrigation head 312 which is inserted and held in the opening of the rectum 338. The soft material and shape of the head 312 enables the device to be less intimidating to users and may be shaped to allow for comfortable insertion into the body. The soft silicone, ergonomically-shaped insertion head and the connected irrigation tube are shaped to be easily inserted and held in the rectum. The soft head alleviates the intimidation that often stems from current rectal cones and catheters and easily conforms when inserted into the rectum. The shaped design will be held by the rectum for initial insertion and the device and tubing will be held in place during TAI use by the attached guide member 314.

During device set-up, the user will utilize the reusable guide member 314 and load the irrigation head 312 onto the post 336 and load the first irrigation tube 318 into the fork 334 and clip 330. Alternately, magnetic components could be used to attach the head and/or tube to the guide member.

With the device set-up and the irrigation head and tubes in place, the user will hold the device between the legs and insert the irrigation head into the rectum. The user can then comfortably grasp the handle and hold the device in place during use. FIG. 41 shows the user 340 sitting on the toilet 342 with the guide member held in position between the legs. The user may then position the pressurized irrigation liquid supply 322 in front of them for easy access and pressurizing.

FIGS. 42-45 illustrate the irrigation liquid supply, including its reservoir 322 and pump 324. The reservoir may preferably be made of rigid polymeric material. By way of example and not limitation, a volume of about 1500 mls is typical and usually satisfactory. The pump has a threaded cap 344 through which a plunger 346 extends. The large cap 344 makes it easy to remove and replace and also makes the reservoir easy to fill. Volume gradations or markings on the reservoir allow the user to monitor the amount of water contained and the amount transferred. The plunger 346 has an enlarged knob 348 which enable the user to move the plunger up and down. Doing so will pressurize the water in the reservoir.

With the system set and the reservoir pressurized, the user can open the control switch 316 (FIG. 33) and start the flow of water through the irrigation tubing and out of the irrigation head into the bowel. When the desired amount of water has been transferred, the user may switch the controller to the off position to stop the water flow. With water induced into the bowel, the insertion head may be removed from the rectum and the user will await a bowel movement.

Among the advantages of the system 310 is that the guide member enables the user to easily remove and hold the connected irrigation head after water has been introduced. The connected tubing can be organized and held by the features on the guide member. A user can utilize the guide member from the side or back if needed for multiple product orientation usage. The rigid container and large screw cap enable the user to easily fill or empty container during and after use. The disposable irrigation head may be a single use element and the rest of the system may be stored and retained for multiple uses with changing frequencies on the order of 1-6 months.

FIG. 46 shows an overview of a TAI handle guide member system 410 according to an alternate embodiment of the present disclosure. The system 410 includes a single-use, shaped, irrigation cone 412 for insertion into the rectum. The cone 412 may be mounted on a quick-release irrigation head 414 which is removably connected to the front loading section 416 of a guide member handle shaft 418. The shaft 418 may carry an insertion mirror 420 which assists a user in positioning the cone 412. The large, easy to grip reusable guide member handle shaft 418 may include quick release connection ports 422 (FIG. 47) and 424 (FIG. 49) on the front loading section 416 and a rear loading section 426, respectively. The rear port 424 may releasably connect to an irrigation tube 428. The rear loading section also permanently mounts a horn 430. The horn 430 may include an upstanding post 432 and a shroud plate 434 extending from the top of the post. The post may be covered with a suitable cushioned material to aid in providing a secure grasp of the horn. The system 410 may also include a water supply 436 similar to that of FIG. 33. The water supply including a large, rigid water reservoir 438 to which is fitted a pump or pressurizing feature 440 to pump and pressurize water for irrigation and pumping into the bowel.

Among the user-friendly features of the system are the mirror 420 which permits the user to visualize and target the rectum when inserting the irrigation cone 412. The large horn portion 430 may include an ergonomic, textured post so a user with limited dexterity can easily grip and hold the device during insertion and use. The large manual pump container which, as indicated above, may preferably be made from a rigid polymeric material, and a large top-mounted pump system allow the user to accurately read and pump the designated amount of water into the bowel during the TAI process. The reusable, handle shaft 418 may be made from rigid, easy to clean polymeric material and may be retained for multiple TAI uses. The large horn will enable the user to easily manipulate the device during use and the curved shape allows the user sitting on the toilet or a commode chair to gain access to the perianal area and to hold the product during use. The disposable irrigation head 414 may be installed in the front loading section 416 to prepare the device for use and align the irrigation tubes for water passage/pumping during TAI.

FIGS. 47 and 48 show the irrigation head insert. The irrigation cone 412 may be similar to the cone systems currently available but utilizing a relatively soft material, such as a soft silicone material. The cone may include a curved profile or shape to aid insertion and entry into the body. It will be understood that the cone 412 may take a different shape from the one shown. The user may load the disposable irrigation head 414 into the front loading section 416 of the handle shaft 418 and click the device into place allowing for easy alignment and securing of the irrigation tubes. With the irrigation head 414 loaded, an irrigation tube on the head (a portion of which is seen at 415 in FIG. 47) and a mating irrigation tube (not shown) in the handle shaft 418 are aligned and ready for use. The shaped cone 412 may be tapered so that the user can hold the component in by holding, gripping, or applying force to the handle shaft 418. The irrigation head section 414 can be quickly released by pressing the release button 442 which will eject the head from the handle shaft 418 after use.

Figure 49:
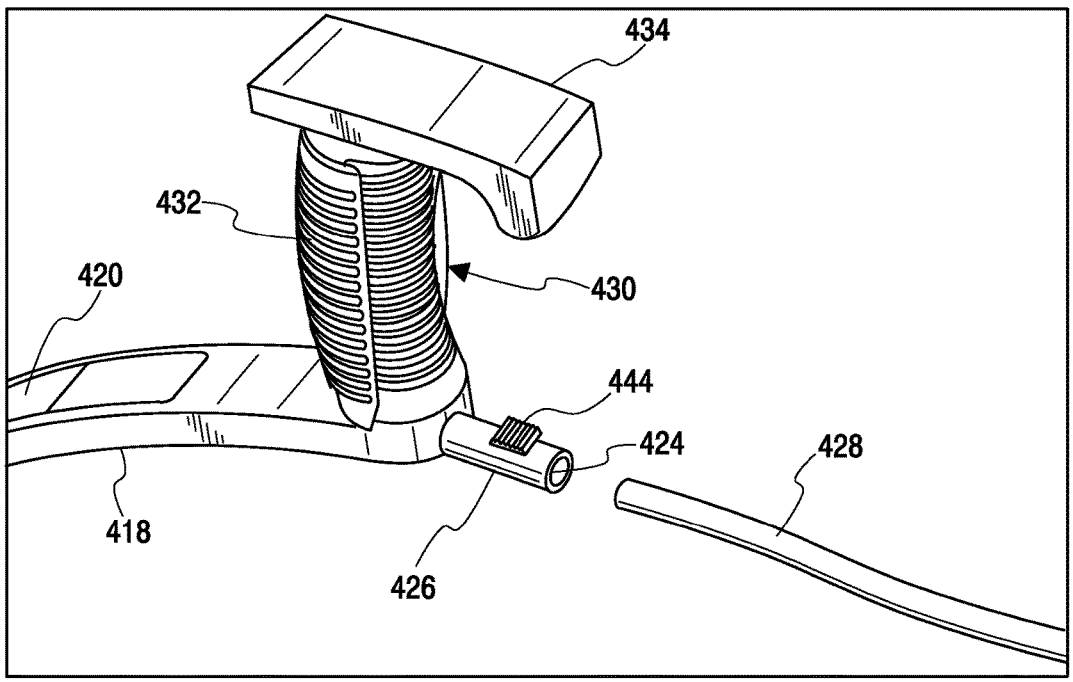
FIG. 49 is a perspective view of a detail of the guide member handle, showing the irrigation tube connection for the system of FIG. 46.
Figure 50:
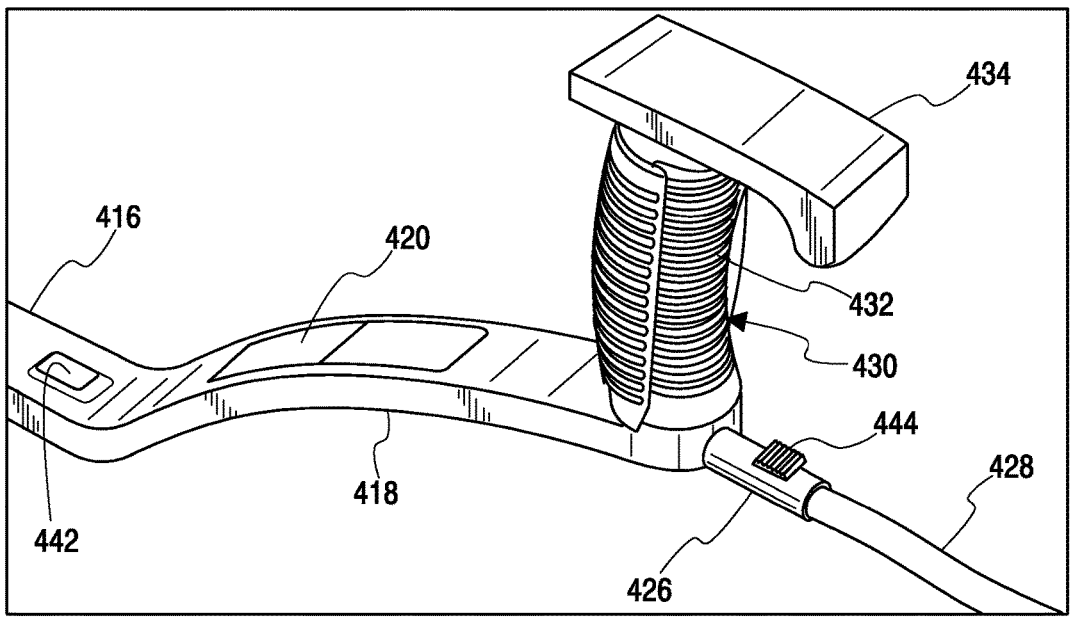
FIG. 50 is a view similar to FIG. 49 but with the irrigation tube installed on the guide member handle.

FIGS. 49 and 50 show further details of the irrigation loading and system set-up. Located on the rear loading section 426 of the handle shaft 418 on the underside is the irrigation tube port 424 which connects the handle section to the water source. The user may simply snap fit and secure the irrigation tube 428 into place, allowing for quick and secure connection of the product for use. As with the disposable head, the guide member handle may feature an irrigation tube quick release, ejection button 444 which the user may press to disconnect the tube 428 after use to remove the product and allow for easier storage.

FIG. 51 shows the graphic of the insertion of the irrigation head into the rectum. The graphic illustrates the user (diagrammatically indicated generally at 446) seated on the toilet with the device set-up and ready for use. The user may grasp the large horn portion 430 and place device between the legs and target the rectum through the use of the assistive mirror 420. The user may then utilize the side 448 of the toilet and the shaped handle to rotate the irrigation head 412 into place and apply force by gripping the handle to hold the cone 412 in place during the TAI process. With the head of the device in place the user's reach is extended through the grasping and holding of the arm device. The user can then comfortably apply force to hold the head in place in the body or rest the system on the side of the toilet.

The details the water supply reservoir and pump are the same as those described in connection with FIGS. 42-45 and will not be repeated here.

FIG. 52 illustrates the device after the irrigation process is complete and water has been introduced into the bowel. The user can remove the irrigation head and place the device on the floor beside the toilet (as shown in FIG. 52) to wait for a bowel movement. The shape of the shaft 418 will hold the head 412 off the floor or other surface and prevent any contamination issues. The irrigation tubing may also be disconnected by pressing the tube release button 444 and the system, minus the head 412, is cleaned and stored for future TAI use.

This system 410 offers several user-friendly benefits. For example, with current systems users often experience apprehension and physical challenges with insertion of the irrigation head, product set-up, product holding, controller interaction and water pumping into the body. The features of the proposed system address all of these concerns in a simplified product solution and allow users to carry out a TAI procedure in a way that is less intimidating to the end user than other systems currently available on the market. The soft shaped irrigation head is less intimidating than a balloon system and facilitates easy insertion of the device into the rectum. The reusable guide member allows the user to sit on the toilet comfortably and extends the user's reach and allows the user to secure their hand comfortable with the device. The user can sit and hold the device between the legs to hold the head in place during use.

Furthermore, the guide member can be rested on the side of the toilet during TAI use which may allow both hands to be free. The guide member with attached irrigation head can be easily removed from the body. The extended reach of the guide member may also have hygienic benefits as the user will be able to hold the device away from the dirty area. The mirror section on the device allows the user to visualize the insertion of the irrigation head into the rectum. The quick release ports on the device allow the user to snap fit components during device set-up and easily dispose or remove items after use. The design has fewer parts than currently available commercial systems making it more intuitive and simpler to use. The user can easily read the gauge on the container in front of them while sitting on the toilet and turn off the pressure system through the controller to shut off the valves and stop water flow during TAI use. Tube connections and irrigation heads can be easily loaded and/or removed by a user with limited dexterity.

The irrigation head can be quickly released and dropped into the waste without the user directly touching the components. The disposable irrigation head may be the single-use section and the rest of the system will be stored and retain for multiple uses.

Figure 53:
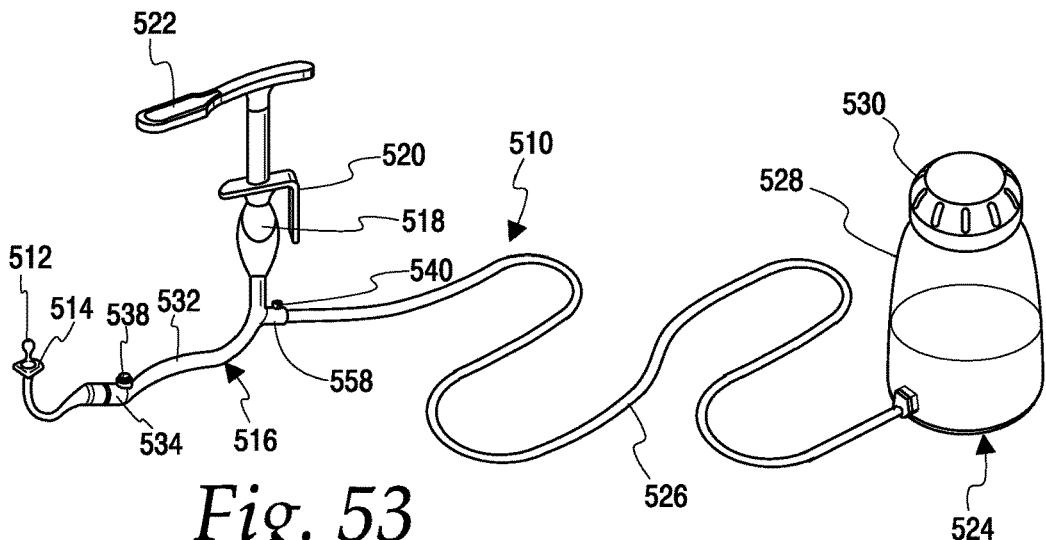
FIG. 53 is a perspective view of a further embodiment of the systems disclosed herein, showing an alternate TAI pump handler system.

FIG. 53 illustrates an overview of a TAI pump handler system 510 according to a further alternate embodiment of the systems disclosed herein. This system has a disposable, ergonomically-shaped insertion head 512 which may conform to and be held by the muscles of the bowel during TAI use. The insertion head 512 may include an absorbent fabric pad 514 to collect and contain any excess liquid lost during the TAI process and absorb excess water to aid in the cleaning process. A large shaped guide member 516 has an ergonomic post 518, a shroud plate 520 and a large pump section with a pump handle 522. This reusable device may be placed between the users leg while sitting on the toilet and insert the attached irrigation head. The pump handle 522 may be pushed up and down to manually pump water from a water supply 524 through irrigation tube 526 and into the body through the irrigation head 512. The water supply may include a reservoir 528 similar to those previously described but having a plain cap 530 that does not include a pump. The reservoir has gradations to permit easy reading of the water level.

Figure 56:
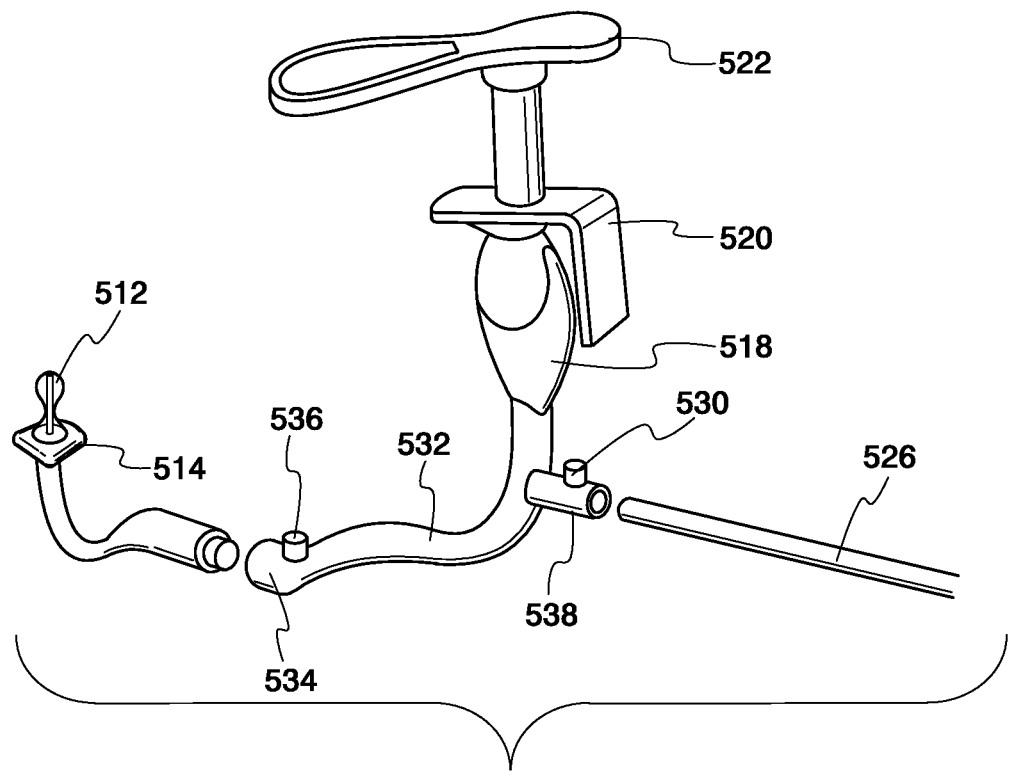
FIG. 56 is a perspective view of the front loading section removed from the handle section for the system of FIG. 53.
Figure 57:
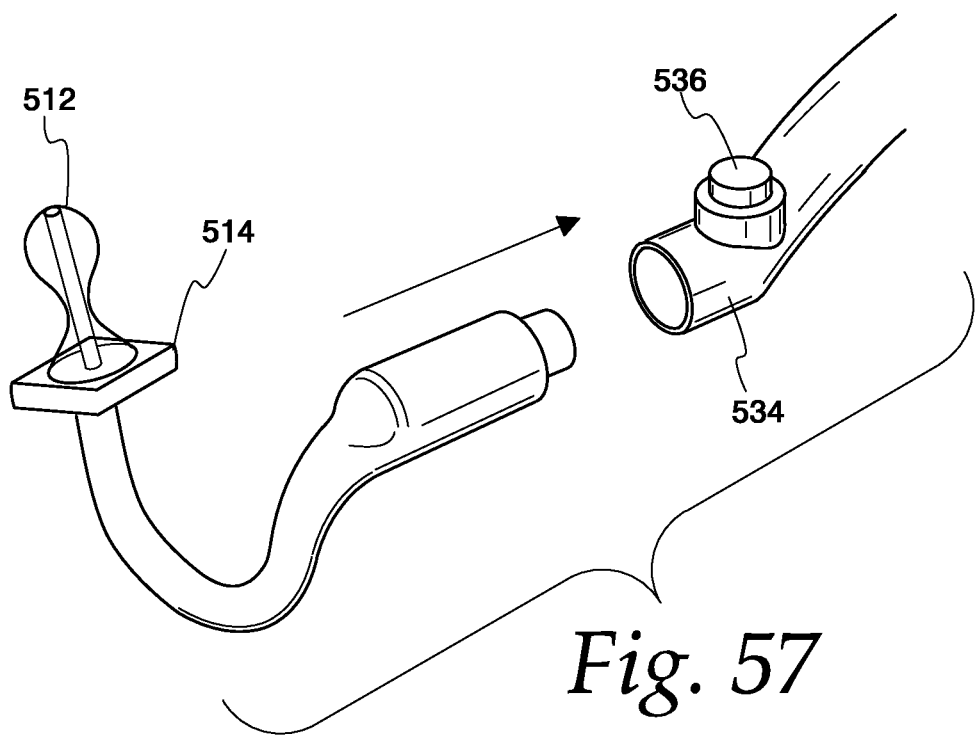
FIG. 57 is another view of the front loading section ready for insertion into the handle section for the system of FIG. 53.
Figure 58:
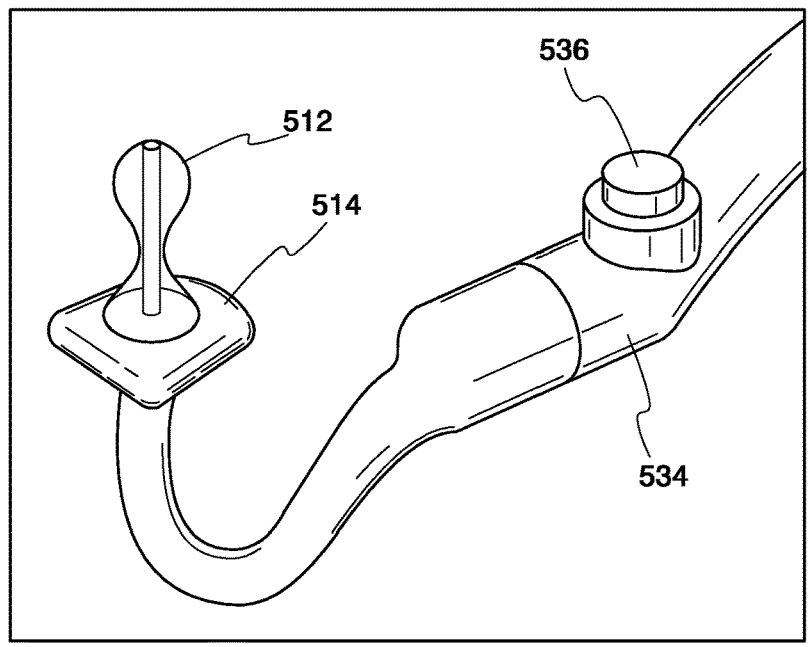
FIG. 58 is similar to FIG. 57 with the front loading section installed on the handle section.

FIGS. 56-58 illustrate certain details of the guide member 516. The guide member has a shank portion 532 that terminates at a front loading section 534. The front loading section includes a quick release button 536. The front loading section 534 joins with the proximal end of the head 512. The user may attach the irrigation head 512 to the front loading section 534 of the guide member 516 to align tubing inside both the head and shank and snap fit the replaceable head into the reusable shank 532 for irrigation usage.

The upper end of the shank portion 532 has a rear loading section 538 with its own quick release button 540. This allows the user to press the irrigation tube 526 into the rear loading section 538 and align the tube 526 with a mating tube (not shown) inside the shank and loading sections of the guide member 516.

The irrigation head 512 may include a small, shaped head to easily insert and fit into the bowel to allow for reduced intimidation and allow for easy removal. As mentioned above, the bottom section of the irrigation head may include an absorbent pad 514 to absorb any excess water expelled during TAI use. This promotes a cleaner product for disposal as excess water will be absorbed and not present on the tubing or guide member.

The large reusable shank portion 532 may be reusable and utilized over multiple TAI usages. The post 518 and pump handle 522 may be held by the user in front of them while sitting on the toilet, thus providing the SCI user control and extended reach in terms of holding and inserting the irrigation head, gripping the head during use, and gripping and pumping the water into the body through an easy to grip pump design.

Figure 54:
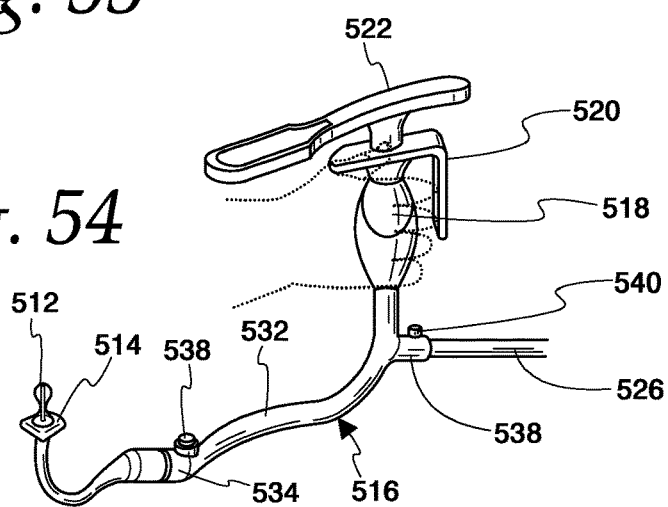
FIG. 54 is a perspective view of a manual pump for the pump handler system of FIG. 53.
Figure 55:
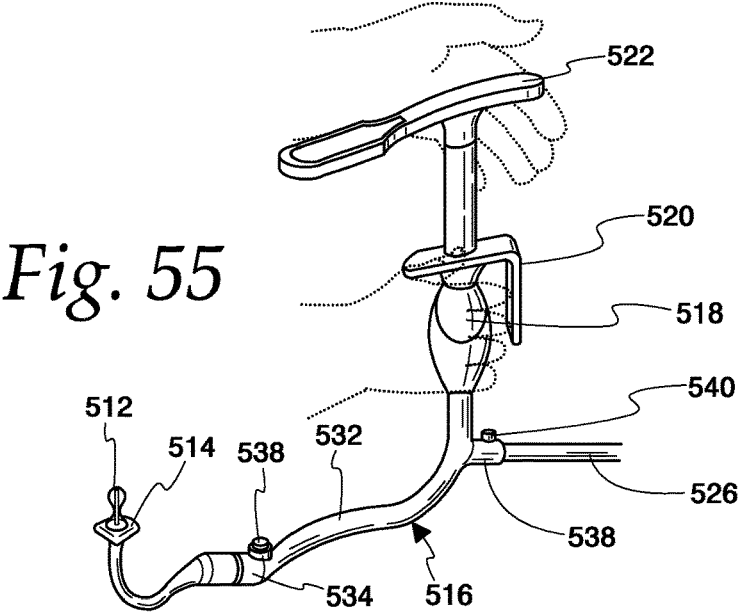
FIG. 55 is a view similar to FIG. 54 showing how the pump is handled and operated.

FIGS. 54 and 55 illustrate aspects of the manual pumping process to induce water into the body. For example, FIG. 54 shows a user grasping the post 518. This post handle may be ergonomically designed to enable the user to easily grip and hold the device comfortably. The shroud plate 520 may wrap around the user's fingers to secure the device to the hand and enable the user to hold the guide member 516 in the manner of a joystick. This will enable the user to apply pressure and control to the attached irrigation head. With the user's hand securely gripped onto the post the top pump handle 522 may be large enough for the user with their opposite hand to move the pump handle up and down. This will activate the pump mechanism inside the post to create a suction that may draw water from the reservoir 528, through the tube 526, through the tubing of the guide member and out of the inserted irrigation head 512 into the bowel.

Figure 59:
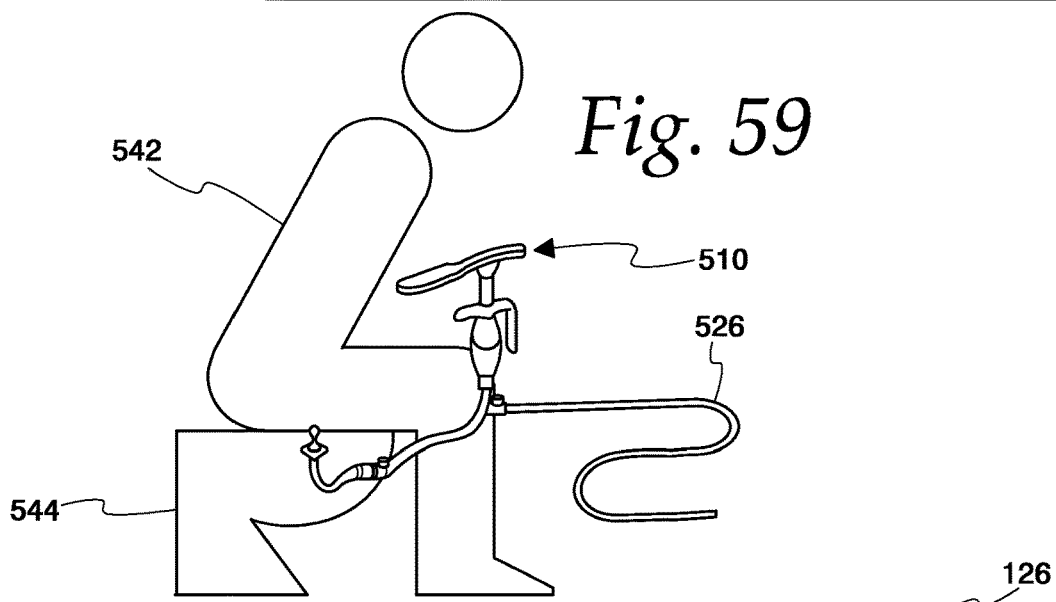
FIG. 59 is a diagrammatic view of a user seated on a toilet and preparing to use the guide member system of FIG. 53.

FIG. 59 illustrates the TAI process and use of the system 510. The user may now have the device set-up and may transfer to a seated position on the toilet to conduct the TAI process. The user 542 may rest the device 510 on the lip of the toilet 544 and extend the user's reach to insert the irrigation head into the bowel for the TAI water pumping. The user may then pump the manual pump handle 522 to induce the designated amount of water into the bowel. The seated user can simply read the water levels pumped on the reservoir 528. The TAI process will be completed as usual and the user may await a bowel movement to flush stool from the bowel. With the process complete the user may press release the disposable head 512 into the waste by pressing the release button 536 on the front loading section 534 of the reusable shank portion 532. The irrigation tube 526 may similarly be disconnected by pressing the quick release button 540. The reservoir 528 and guide member 516 may be wiped down and stored for later TAI uses.

The problems that the TAI system 510 addresses include, among other things, ease of use for the SCI user who is subject to a TAI bowel care program. As previously discussed, for many individuals, insertion of the irrigation head, product set-up, product holding, controller interaction and water pumping into the body may be challenging and intimidating. The systems described herein address all of these concerns in a simplified product solution. For example, the soft shaped irrigation head allows for reduced intimidation and easy insertion of the irrigation head into the rectum. The reusable guide member allows the user to sit on the toilet comfortably and extends the user's reach and allows the user to secure their hands comfortably on the device. The user can sit and hold the device between the legs to hold the head into the rectum during use. The guide member can be rested on the side of the toilet during TAI use which will enable the two hands to be free during TAI use. The guide member with attached irrigation head can enable the user to easily remove the irrigation head after the catheter has been induced into the body. The extended reach of the guide member also has hygienic benefits in that the user will not have to place their hands near the bowel thus increasing hygiene.

Furthermore, the quick release ports on the device allow the user to snap fit components during device set-up and easily remove and dispose of items after use. A pump system and reusable guide member enable the SCI user to easily draw and pump water into the body. The large reservoir can be easily filled with the appropriate amount of water and allows the user to accurately pump a set amount into the body. The user can accurately read the gauge on the reservoir in front of them while sitting on the toilet. The guide member may extend the reach of a SCI user and allows the irrigation head to be held/gripped through interaction. The guide member can be rested on the toilet bowel and the user hands can be placed on the guide member section increasing user's grip. The guide member enables the user to easily remove and hold the connected irrigation head after water has been induced. Tube connections and irrigation heads can be easily loaded/removed by a limited dexterity user before and after use. The guide member can be easily wiped down and retained for multiple uses. A user can utilize the guide member from the side or back if needed for multiple product orientation usage. The rigid reservoir and large screw cap can enable the user to easily fill or empty the reservoir during and after use. The disposable irrigation head may be the only disposable section and the rest of the system may be stored and retain for future use. Quick release of the irrigation head can be press released and dropped into the waste without the user directly touching the components.

The components and features included in the systems disclosed herein improve on current products for use by an SCI user, e.g. large handle, soft shaped irrigation head, mirror insertion, easy to load or remove items. The absorbent section will retain any excess water and promote a cleaner product for use/disposal after use. The large pump section replaces current pumping designs and promotes a more SCI-friendly pumping alternative as more accurate pump can be undertaken by the user.

Figure 60:
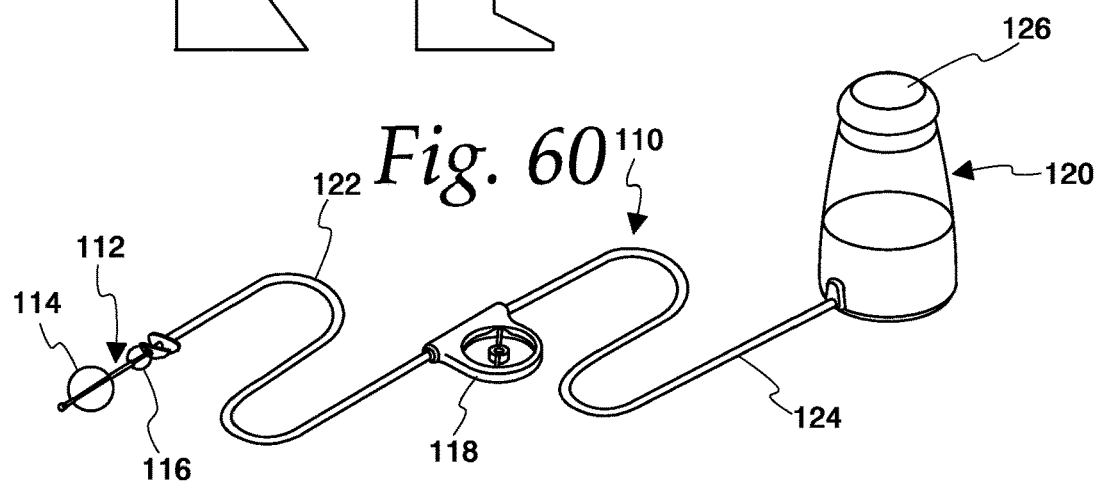
FIG. 60 is a perspective view of a further alternate embodiment of a TAI pressure system with the irrigation head shown in its deployed condition.

FIG. 60 shows an overview of another embodiment of the TAI systems disclosed herein, this one being an auto retention TAI system 110. The device may include a disposable irrigation head 112 fitted with a plurality of pre-loaded liquid filled balloons 114, 116 which can be easily inserted and deployed into the opening of the bowel for TAI use. The liquid in the balloons 114, 116 may be oil, such as, for example mineral oil. A small scale motorized in-line pump 118 may be included and can be turned on to pump or draw irrigating liquid from a supply 120 into the bowel utilizing a set amount of pressure and total flow. A first irrigation tube 122 may be removably connected to the head 112. Tube 122 also may be connected to the pump 118. A second irrigation tube 124 may join the pump to supply 120. The irrigation liquid supply may be a rigid container with an easy to open top cap 126.

Figure 61:
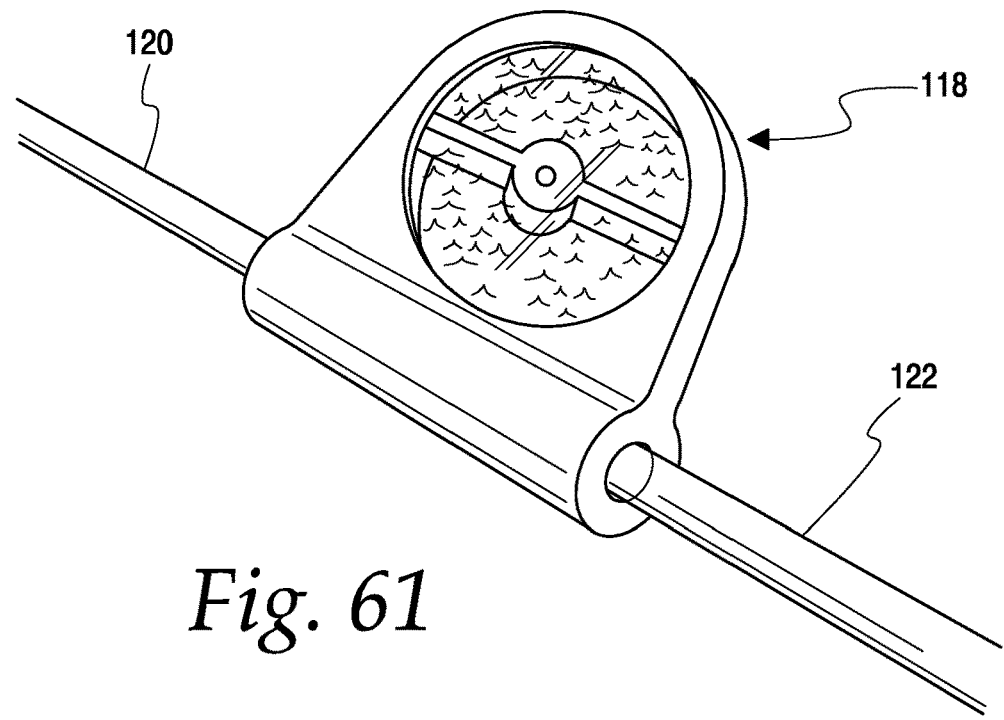
FIGS. 61 and 62 are perspective views of the in-line pump of FIG. 60.

FIG. 61 shows the small, in-line, hands-free motorized pump 118 for use with the embodiment of FIG. 60 or other embodiments of the system disclosed herein. The in-line motorized pumps assist in the irrigation process from the irrigation fluid supply to the body. The hands-free design at least substantially eliminates the need for manual pumping and will effectively pump the designated amount of water into the body. The user will turn on the water pump (which may be a peristaltic pump) to draw water or other liquid from the irrigation fluid supply, allowing a pre-determined amount of liquid to flow through the system, through the irrigation head and into the body.

Figure 62:
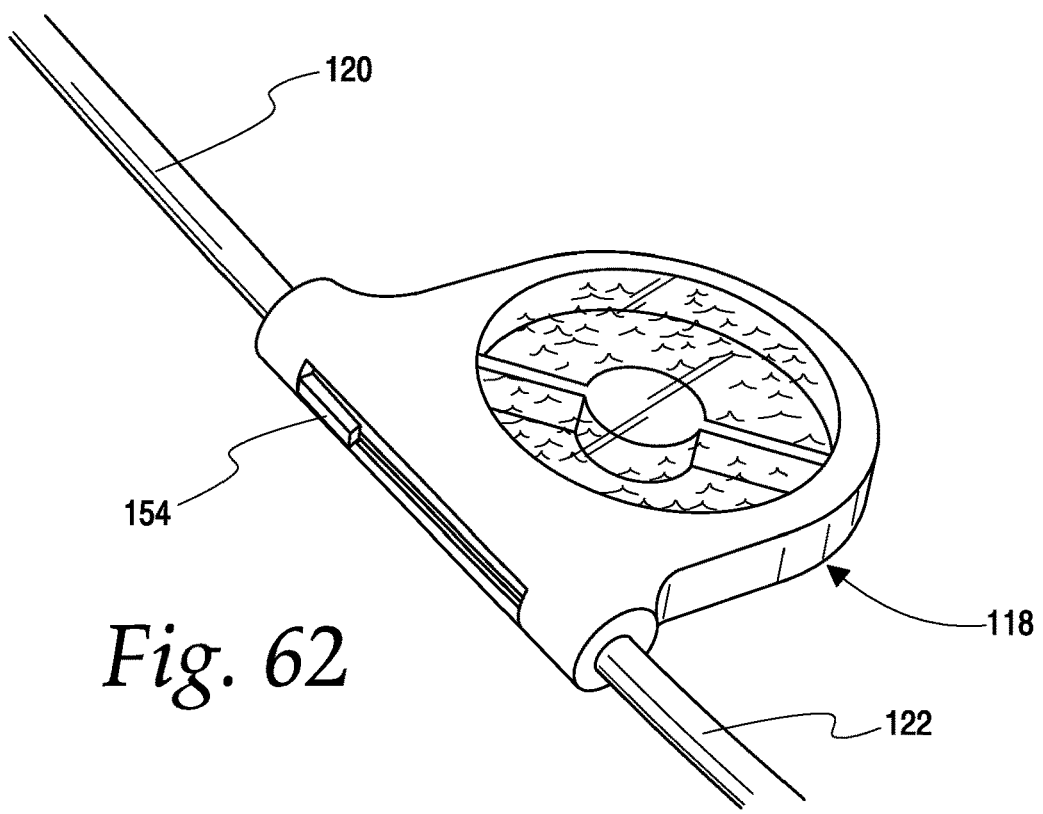
Figure 63:
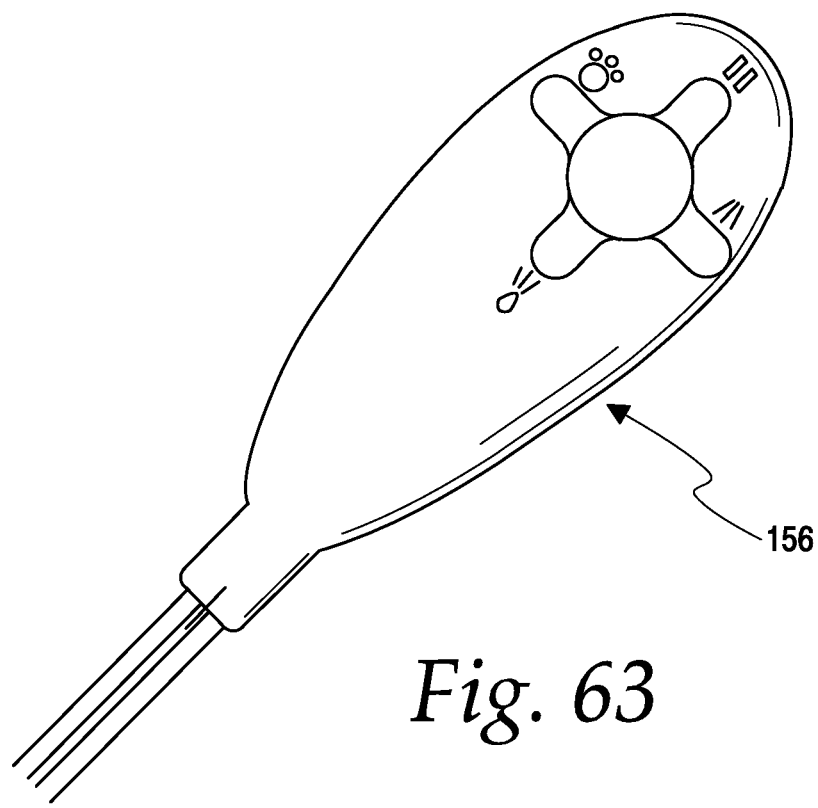
FIG. 63 is a front view of a joy stick controller for the in-line pump.

FIGS. 62 and 63 illustrate the simplified controls and optional controller for use with the system. The motor may feature a simple slider on/off switch 154 to indicate to the user a slide on/off function for the motored irrigation process. Additionally, a secondary style joy stick control 156 may be used in conjunction with the device to enable the user to switch the system on/off during use. In an alternate embodiment, the irrigation pump may be incorporated into the base of the controller which is held by the user to aid in pumping of water.

Once the irrigation head is inserted and the balloons inflated, the user may turn on the pump on to induce a controlled or set amount of irrigating liquid into the deployed irrigation head and from there into the body. This system will allow the user to induce water flow with less effort and provides a simple Stop-Start irrigation process for their irrigation needs. With irrigation complete, the user may simply turn off the system and withdraw the press pad 138. This will deflate the balloons and allow removal of the irrigation head from the body.

Figure 64:
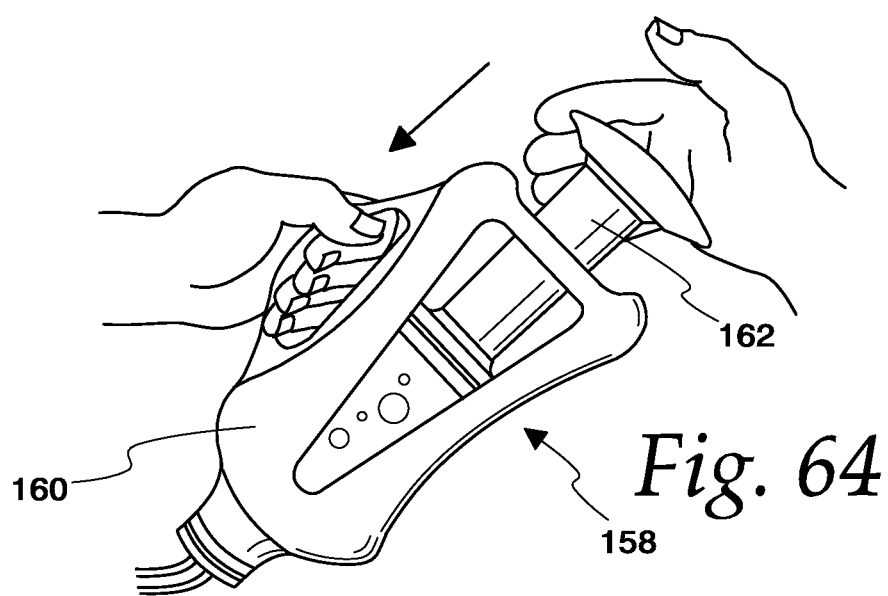
FIG. 64 is an alternate form of pump for use with the system of FIG. 60.
Figure 65:
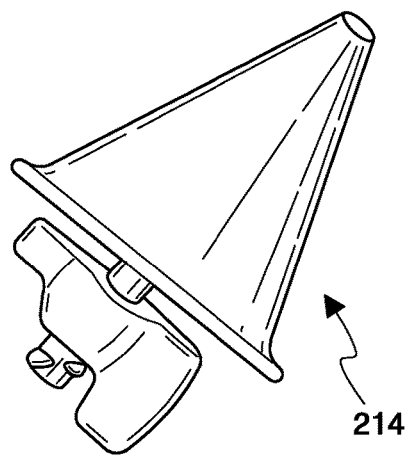
FIG. 65 is a perspective view of a stoma irrigation head for use in a modular head system.
Figure 66:
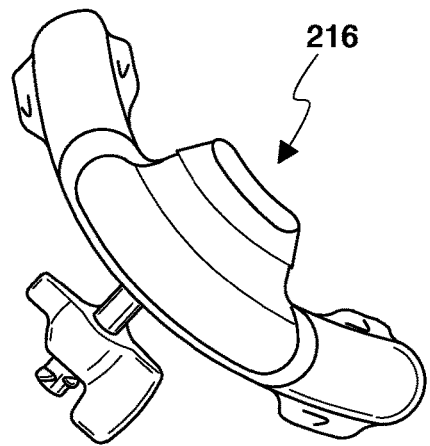
FIG. 66 is a perspective view of an adhesive irrigation head for use in a modular head system.

FIG. 64 also shows an alternative pump 158 to replace the motorized pumping section. In this insulated water pump the housing 160 may include a handle that may be gripped or otherwise manipulated by the user. Water is forced through the system by the user pressing on a piston 162. This simple pump may be utilized with the system to replace a motorized irrigation mechanism to allow the use of a manual pumping of water into the body using the deployable irrigation head 112.

Many individuals may find insertion of the irrigation head, product set-up, product holding, controller interaction and water pumping into the body challenging and/or intimidating. The features of the systems disclosed herein address all of these concerns in a simplified product solution. Pressure irrigation, simple operation controllers and auto retain/removal heads simplify the TAI process and allow the user to utilize a more intuitive, user-friendly system for their TAI needs.

Figure 67:
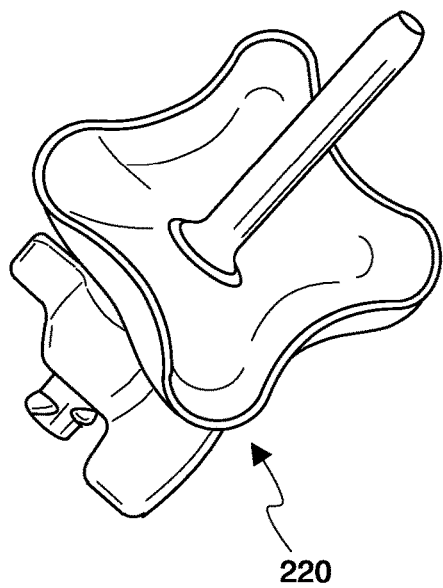
FIG. 67 is a perspective view of a water filled balloon irrigation head for use in a modular head system.
Figure 68:
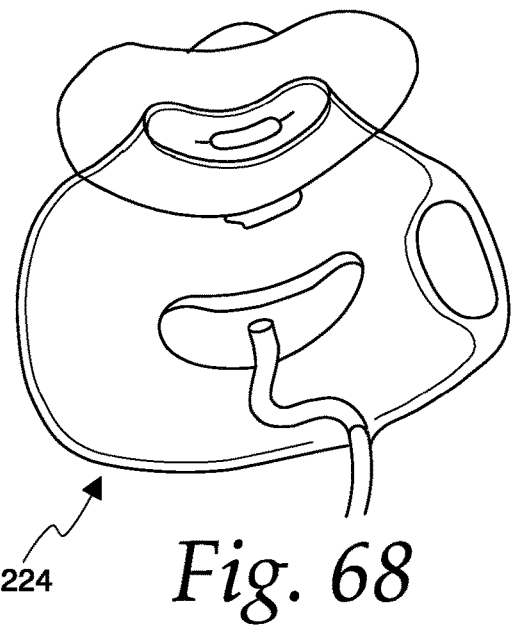
FIG. 68 is a perspective view of a closed collection irrigation head for use in a modular head system.
Figure 69:
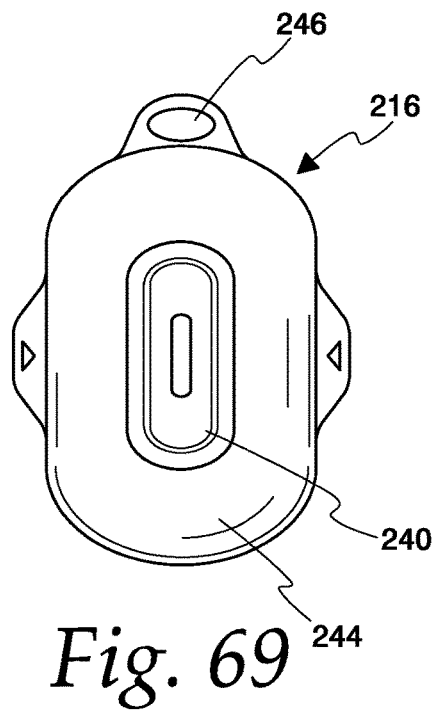
FIG. 69 is a front elevation view of an adhesive irrigation head, showing the adhesive pad and a cone.
Figure 70:
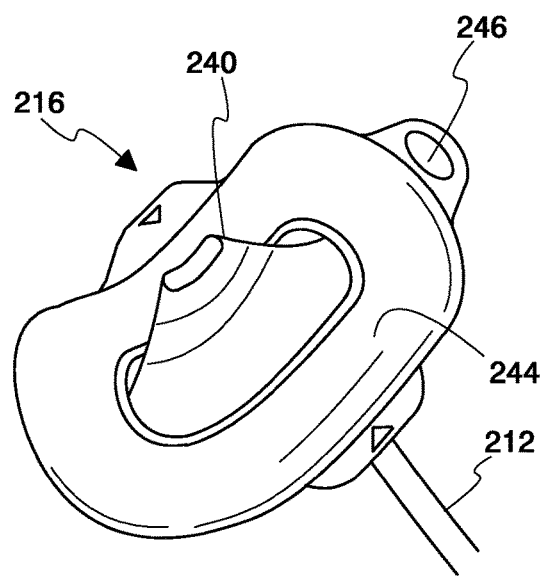
FIG. 70 is a perspective view of an adhesive irrigation head, showing the adhesive pad and a cone.
Figure 71:
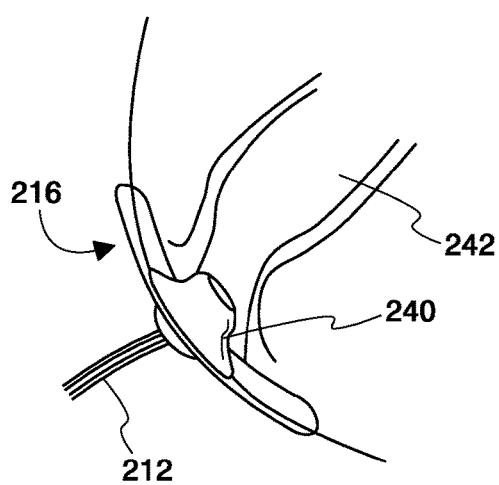
FIG. 71 is a diagrammatic section showing the adhesive irrigation head in use.
Figure 72:
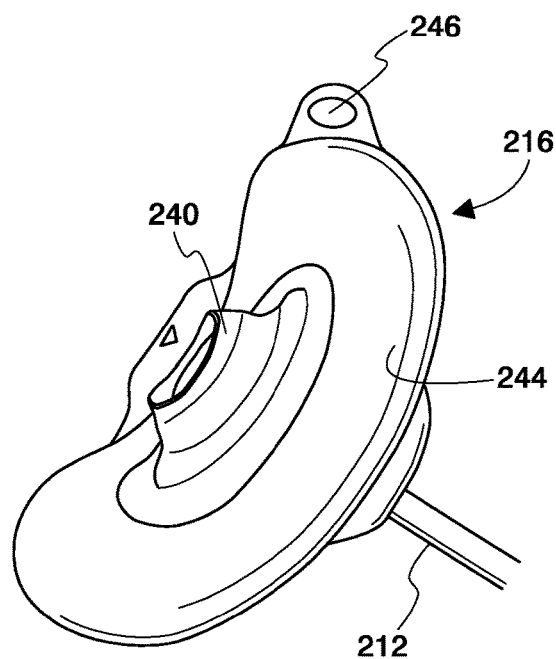
FIG. 72 is an enlarged perspective view of an adhesive irrigation head, showing the adhesive pad and a cone.

Further alternate irrigation heads for use with the gravity feed system of FIG. 13 are shown in FIGS. 65-68. These include a stoma irrigation head 214 (FIG. 65), an adhesive irrigation head 216 (FIG. 66), a suction cup irrigation head 220 (FIG. 67) and a closed collection head 224 (FIG. 68).

The adhesive irrigation head 216 is shown in FIGS. 69-72. The adhesive irrigation head has a softer, ergonomically-shaped cone 240 which is shaped and tailored for holding at the opening of the rectum 242. Head 216 may include a skin-friendly adhesive pad 244 which the user may attach to the buttocks to secure and hold the device in place during the TAI process. The removal tabs 246 may be pulled to easily remove the device after use.

Figure 73:
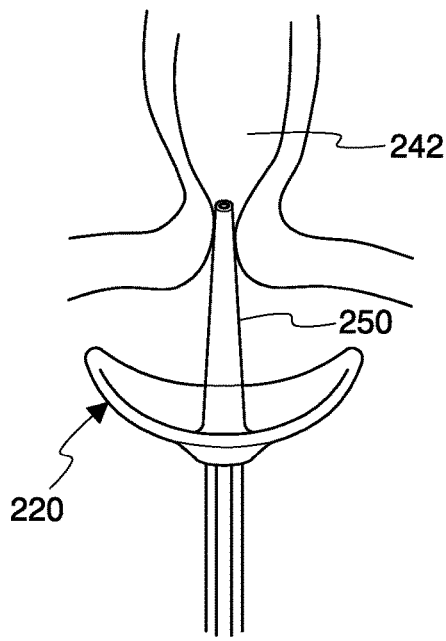
FIG. 73 is a diagrammatic section showing the suction cup irrigation head in an initial stage of insertion.
Figure 74:
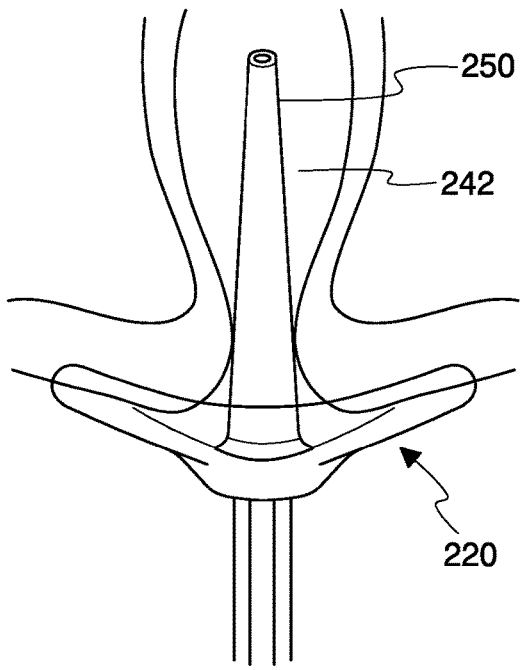
FIG. 74 is a diagrammatic section showing the suction cup irrigation head in use.

In an alternative embodiment of securing the irrigation head, a suction cup holding irrigation head may be provided and is shown in FIGS. 67, 73 and 74. This head 220 with suction retaining features may adhere through a small amount of suction to the buttocks to hold head 220 in place. Suction pressure may be removed when the user pulls the rectal catheter 250 out of place after use. As noted above, the suction method provides an alternative holding mechanism for retention of the catheter during the TAI process. The device will be retained to the outside of the body through the use of minimal suction thus reducing intimidation of the device. A removal feature or a release of suction may be present to aid in the removal of the device.

Figure 75:
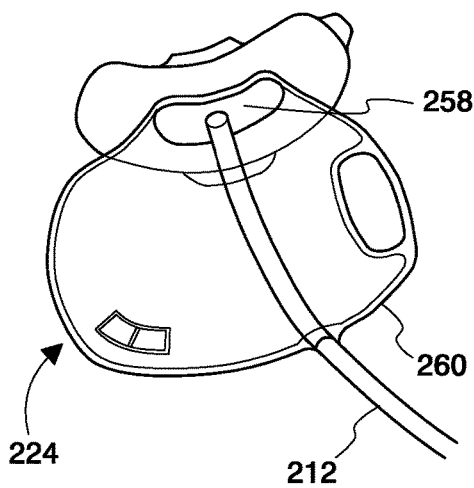
FIG. 75 is a perspective view of the closed collection head.
Figure 76:
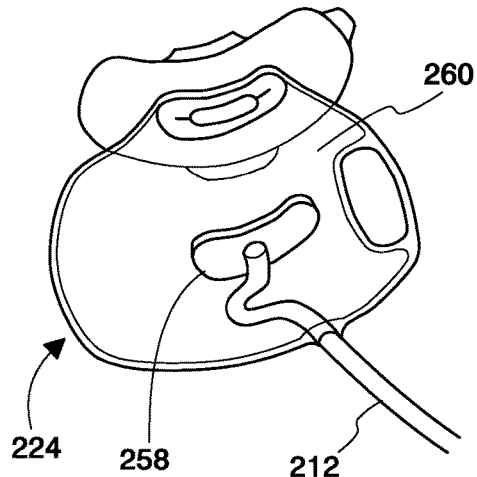
FIG. 76 is a perspective view of the closed collection head collection head in use with the irrigation tube withdrawn and the collection bag ready for use.

The closed collection irrigation head 224 is shown in FIGS. 75 and 76. The closed collection head is a combination device which may include an adhesive holding irrigation head 258 and a closed collection bag 260 for the collection of fecal matter released during the TAI process. The bag 260 will typically be an opaque color to discreetly cover the contents collected inside and may also include a carbon filter to remove any associated odors. The irrigation tube 212 drops down from the head 258 to expose the opening of the rectum. Waste is collected and retained within attached waste bag 260.

It should be understood that various changes and modifications to the presently preferred embodiments described herein will be apparent to those skilled in the art. Such changes and modification can be made without departing from the spirit and scope of the invention disclosed herein.

The invention claimed is:

1. A trans-anal irrigation device, comprising:
an irrigation liquid reservoir;
tubing connected at a first end to the reservoir and in fluid communication therewith;
an irrigation head engageable with the tubing at a second end to provide fluid communication between the tubing and a conduit of the irrigation head,
the irrigation head comprising:
a hollow barrel having a wall and at least one port through the wall and in fluid communication with the interior of the barrel, the conduit being disposed in and extending through the barrel, the conduit and barrel wall defining an annulus between an exterior of the conduit and an interior surface of the wall;
a plunger having a hollow shaft, the shaft being sized to fit in the annulus for reciprocal movement therein; and
a balloon surrounding the barrel and having a distal end sealed on one side of the at least one port and a proximal end sealed on the other side of the at least one port.

2. The trans-anal irrigation device of claim 1 wherein the balloon in an expanded configuration has a lug shape to conform to an inner channel of the bowel.

3. The trans-anal irrigation device of claim 1 further comprising:
a tubing connector attached to the second end of the tubing; and
a head connector attached to the irrigation head, the head connector being selectably engageable with the tubing connector to provide fluid communication between the tubing and the irrigation head.

4. The trans-anal irrigation device of claim 1 wherein the tubing further comprises a valve to control flow of irrigation liquid.

5. The trans-anal irrigation device of claim 1 further comprising a pump for supplying the irrigation fluid to the irrigation head.

6. The trans-anal irrigation device of claim 5 wherein the pump is located in the irrigation liquid reservoir.

7. The trans-anal irrigation device of claim 5 wherein the pump is located in the tubing.

8. The trans-anal irrigation device of claim 1 further comprising a controller for governing irrigation liquid flow from the reservoir to the irrigation head.

9. The trans-anal irrigation device of claim 1 wherein the wall includes a second port through the wall and in fluid communication with the interior of the barrel; and
a second balloon surrounding the barrel and having a distal end sealed on one side of the second port and a proximal end sealed on the other side of the second port.

10. The trans-anal irrigation device of claim 1 wherein the annulus is filled with a fluid, and the fluid inflates the balloon to an expanded configuration when the plunger is moved in a proximal direction relative to the barrel.

11. The trans-anal irrigation device of claim 1 wherein the plunger includes a press pad.

12. The trans-anal irrigation device of claim 1 wherein the conduit include an opening that is exterior of the barrel.

13. A trans-anal irrigation head, comprising:
a conduit configured to be in fluid communication with a reservoir of irrigation liquid;
a hollow barrel having a wall and at least one port through the wall and in fluid communication with the interior of the barrel, the conduit being disposed in and extending through the barrel, the conduit and barrel wall defining an annulus between an exterior of the conduit and an interior surface of the wall;
a plunger having a hollow shaft, the shaft being sized to fit in the annulus for reciprocal movement therein; and
a balloon surrounding the barrel and having a distal end sealed on one side of the at least one port and a proximal end sealed on the other side of the at least one port.

14. The trans-anal irrigation head of claim 13 wherein the wall includes a second port through the wall and in fluid communication with the interior of the barrel; and
a second balloon surrounding the barrel and having a distal end sealed on one side of the second port and a proximal end sealed on the other side of the second port.

15. The trans-anal irrigation head of claim 13 wherein the annulus is filled with a fluid, and the fluid inflates the balloon when the plunger is moved in a proximal direction relative to the barrel.

16. The trans-anal irrigation head of claim 13 wherein the plunger includes a press pad.

17. The trans-anal irrigation head of claim 13 wherein the conduit include an opening that is exterior of the barrel.

18. The trans-anal irrigation head of claim 13 wherein the balloon in an expanded configuration has a lug shape to conform to an inner channel of the bowel.

* * * * *